United States Patent
Sinha et al.

(10) Patent No.: US 11,915,819 B2
(45) Date of Patent: Feb. 27, 2024

(54) METHODS AND SYSTEMS FOR MULTI-OMIC INTERVENTIONS

(71) Applicant: Food Rx and AI, Inc., Mountain View, CA (US)

(72) Inventors: Ranjan Sinha, Los Altos Hills, CA (US); Shreyas V. Kumbhare, Maharashtra (IN); Inti Pedroso, Región del Maule (CL); Daniel E. Almonacid, San Diego, CA (US)

(73) Assignee: Food Rx and AI, Inc., Mountain View, CA (US)

( * ) Notice: Subject to any disclaimer, the term of this patent is extended or adjusted under 35 U.S.C. 154(b) by 0 days.

(21) Appl. No.: 17/817,558

(22) Filed: Aug. 4, 2022

(65) Prior Publication Data

US 2023/0047307 A1 Feb. 16, 2023

Related U.S. Application Data

(60) Provisional application No. 63/274,122, filed on Nov. 1, 2021, provisional application No. 63/246,348, filed on Sep. 21, 2021, provisional application No. 63/230,656, filed on Aug. 6, 2021.

(51) Int. Cl.
| | |
|---|---|
| *G16H 20/60* | (2018.01) |
| *G16B 40/00* | (2019.01) |
| *G16B 20/20* | (2019.01) |
| *G16H 20/00* | (2018.01) |
| *G16B 5/00* | (2019.01) |
| *G16B 20/00* | (2019.01) |

(52) U.S. Cl.
CPC ............... *G16H 20/60* (2018.01); *G16B 5/00* (2019.02); *G16B 20/00* (2019.02); *G16B 20/20* (2019.02); *G16B 40/00* (2019.02); *G16H 20/00* (2018.01)

(58) Field of Classification Search
CPC ........ G16H 20/00; G16H 20/60; G16B 20/20; G16B 40/00
See application file for complete search history.

(56) References Cited

U.S. PATENT DOCUMENTS

| | | |
|---|---|---|
| 6,582,908 B2 | 6/2003 | Fodor et al. |
| 7,109,206 B2 | 9/2006 | Seed et al. |
| 7,157,235 B2 | 1/2007 | Breit et al. |
| 10,734,096 B1 | 8/2020 | Neumann |
| 2012/0220477 A1 | 8/2012 | Steinthorsdottir et al. |
| 2014/0004183 A1 | 1/2014 | Soni et al. |
| 2016/0232280 A1 | 8/2016 | Apte et al. |
| 2017/0199189 A1 | 7/2017 | Wade |
| 2018/0261329 A1 | 9/2018 | Blander et al. |
| 2018/0320233 A1 | 11/2018 | Perkins |
| 2019/0102512 A1 | 4/2019 | Segal et al. |
| 2020/0368322 A1 | 11/2020 | Geiger et al. |
| 2021/0118559 A1 | 4/2021 | Lefkofsky |
| 2021/0158918 A1 | 5/2021 | Neumann |
| 2021/0163929 A1 | 6/2021 | Wan |
| 2021/0275600 A1 | 9/2021 | Tets et al. |

FOREIGN PATENT DOCUMENTS

| | | |
|---|---|---|
| WO | 2011163231 A2 | 12/2011 |
| WO | 2017214068 A1 | 12/2017 |
| WO | 2020165175 A1 | 8/2020 |

OTHER PUBLICATIONS

Agakidis, C., Kotzakioulafi, E., Petridis, D., Apostolidou, K., and Karagiozoglou-Lampoudi, T. (2019). Mediterranean diet adherence is associated with lower prevalence of functional gastrointestinal disorders in children and adolescents. Nutrients 11:1283.

Black, C. J., Drossman, D. A., Talley, N. J., Ruddy, J., and Ford, A. C. (2020). Functional gastrointestinal disorders: advances in understanding and management. Lancet 396, 1664-1674. doi: 10.1016/S0140-6736(20)32115-2.

Carco, C., Young, W., Gearry, R. B., Talley, N. J., McNabb, W. C., and Roy, N. C. (2020). Increasing evidence that irritable bowel syndrome and functional gastrointestinal disorders have a microbial pathogenesis. Front. Cell. Infect. Microbiol. 10:468. doi: 10.3389/fcimb.2020.00468.

Cruz-Aguliar, R. M., Wantia, N., Clavel, T., Vehreschild, M. J. G. T., Buch, T., Bajbouj, M., et al. (2019). An open-labeled study on fecal microbiota transfer in irritable bowel syndrome patients reveals improvement in abdominal pain associated with the relative abundance of akkermansia muciniphila. Digestion 100, 127-138. doi: 10.1159/000494252.

Enroth, S., Johansson, A, Enroth, S. B., and Gyllensten, U. (2014). Strong effects of genetic and lifestyle factors on biomarker variation and use of personalized cutoffs. Nat. Commun. 5:4684. doi: 10.1038/ncomms5684.

Johannesson, E., Ringström, G., Abrahamsson, H., and Sadik, R. (2015). Intervention to increase physical activity in irritable bowel syndrome shows long-term positive effects. World J. Gastroenterol. 21, 600-608. doi: 10.3748/wjg.v21.2.600.

Severin R, Sabbahi A, Mahmoud AM, Arena R, Phillips SA. Precision medicine in weight loss and healthy living. Prog Cardiovasc Dis Jan. 2019;62(1):15-20.

Brennan L. Metabolomics in nutrition research—a powerful window into nutritional metabolism. Essays Biochem 2016;60(5):451-458.

(Continued)

*Primary Examiner* — Jerry Lin

(57) ABSTRACT

A platform providing methods and systems for prevention and/or treatment of a health condition, where a method can include: simultaneously reducing severity symptoms of the health condition and comorbid conditions upon: receiving a set of samples from one or more subjects; receiving a biometric dataset from one or more subjects; receiving a lifestyle dataset from one or more subjects; returning a genomic single nucleotide polymorphism (SNP) profile and a baseline microbiome state upon processing the set of samples, the biometric dataset, and the lifestyle dataset with a set of transformation operations; generating personalized intervention plans for the one or more subjects upon processing the genomic SNP profile and the baseline microbiome state with a multi-omic model; and executing the personalized intervention plans for the one or more subjects.

16 Claims, 15 Drawing Sheets

(56) References Cited

OTHER PUBLICATIONS

Fall T, Ingelsson E. Genome-wide association studies of obesity and metabolic syndrome. Mol Cell Endocrinol Jan. 25, 2014;382(1):740-757.

Wardle J, Carnell S, Haworth C, Farooqi I, O'Rahilly S, Plomin R. Obesity associated genetic variation in FTO is associated with diminished satiety. J Clin Endocrinol Metab Sep. 2008;93(9):3640-3643.

Frost F, Storck LJ, Kacprowski T, Gärtner S, Ruhlemann M, Bang C, et al. A structured weight loss program increases gut microbiota phylogenetic diversity and reduces levels of Collinsella in obese type 2 diabetics: a pilot study. PLoS One Jul. 18, 2019;14(7):e0219489.

Remely M, Tesar I, Hippe B, Gnauer S, Rust P, Haslberger A. Gut microbiota composition correlates with changes in body fat content due to weight loss. Beneficial Microbes Aug. 2015;6(4):431-439.

Sinha et al. Leveraging Genomic Associations in Precision Digital Care for Weight Loss: Cohort Study. Journal of Medical Internet Research. May 19, 2021. vol. 23, No. 5.

International Search Report for PCT/US22/74544, dated Jan. 4, 2023.

METHODS AND SYSTEMS FOR MULTI-OMIC INTERVENTIONS

CROSS-REFERENCE TO RELATED APPLICATIONS

This application claims the benefit of U.S. Provisional Application No. 63/230,656 filed on 6 Aug. 2021, U.S. Provisional Application No. 63/246,348 filed on 21 Sep. 2021, and U.S. Provisional Application No. 63/274,122 filed on 1 Nov. 2021, which are each incorporated in its entirety herein by this reference.

TECHNICAL FIELD

The disclosure generally relates to systems executing methods for sampling, processing, and identifying diagnostic and therapeutic signatures in patients, with actionable outcomes (e.g., in relation to prevention, diagnostic, and/or treatment of conditions), in the field of multi-omics.

BACKGROUND

Healthcare systems domestically and internationally are impacted by large numbers of patients with preventable health conditions. Preventive healthcare approaches are thus being developed and participation is incentivized in order to proactively improve patient health states. Curative healthcare approaches are also useful in minimizing impact on healthcare systems, especially in the context of returning individuals to healthy states such that they no longer burden healthcare systems. While many preventative and curative healthcare approaches for prevention and treatment of chronic diseases center around behavioral and lifestyle changes, such approaches are often applied in a general and non-personalized manner. Furthermore, general and personalized approaches both suffer from patient compliance issues, limitations in contextual data streams used to drive successful outcomes, limitations in ability to provide just-in-time interventions, and other factors.

Genomic characterization of patients can be used for diagnostic purposes; however, such characterizations often provide a partial characterization of a patient's state, in the interests of improving personalization of preventive and curative care options. Furthermore, methods for identification of diagnostic signatures from patient samples, and generation and application of therapeutic pathways (e.g., combinatorial therapies) tailored to specific patients have not been viable due to limitations in current technologies.

Diet and lifestyle-related illnesses like cardiovascular health conditions and functional gastrointestinal disorders (FGIDs) are rapidly emerging health issues worldwide. Research has focused on addressing FGIDs via in-person cognitive-behavioral therapies and lifestyle modifications with a focus on diet modulation and pharmaceutical intervention. However, there is a paucity of work covering the effectiveness of digital care based on genome SNP and gut microbiome markers to guide lifestyle and dietary modulations on FGID associated symptoms, and on modelling diseased groups or outcomes based on a combination of these markers.

As such, there is a need in the field of multi-omics to characterize patient statuses and improve patient outcomes using personalized care approaches in a more informed manner.

DESCRIPTION OF THE EMBODIMENTS

Figure 1A:
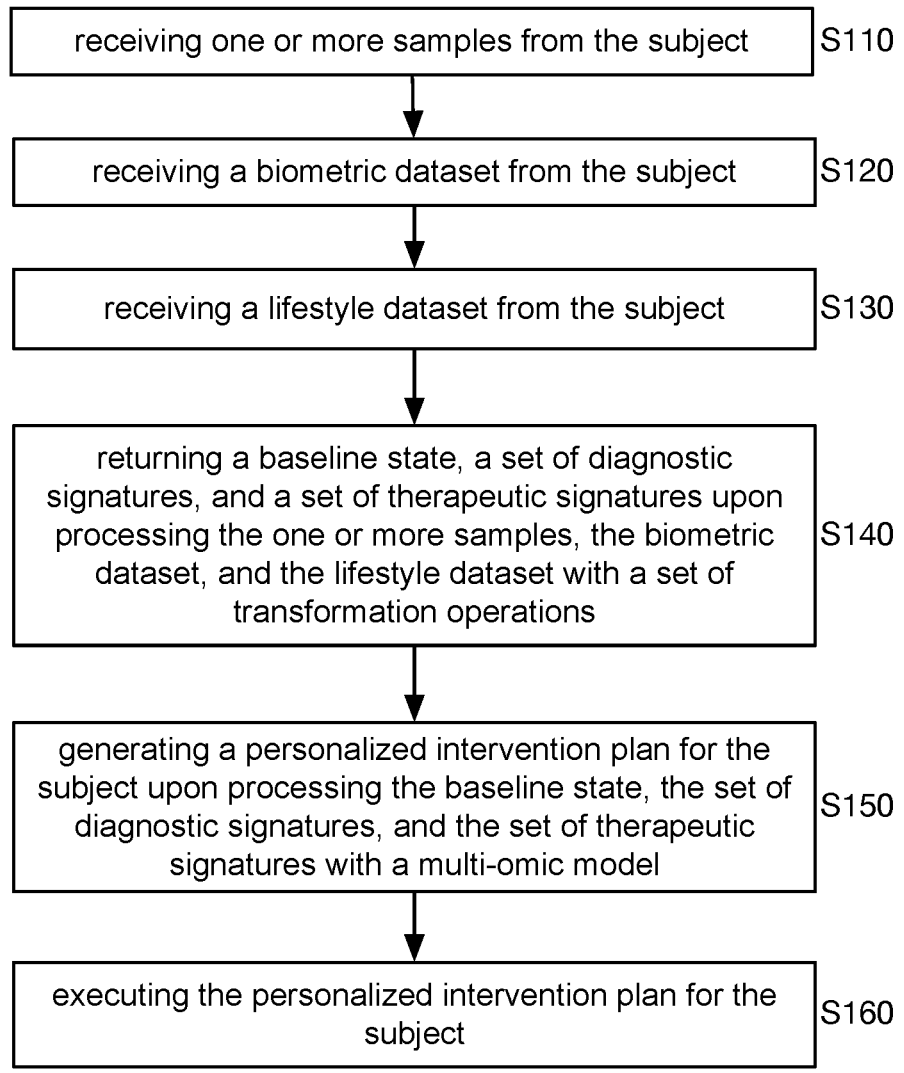
FIG. 1A depicts an embodiment of a workflow of a method for obtaining diagnostic and therapeutic signatures for a subject based on multi-omic models and executing a personalized intervention plan.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. BENEFIT(S)

The invention(s) provide systems and methods for generating multi-omic (i.e., genomic, microbiome analysis-based, behavior-based, lifestyle-based, clinical marker-based, etc.) diagnostics and therapeutic pathways for precision care (e.g., with respect to prevention, diagnosis, and/or treatment of conditions) in response to various indications. In examples, characterizations can be used to provide actionable insights, with example executed actions including recommendations of inexpensive dietary and lifestyle therapeutic interventions. Additionally or alternatively, characterizations and data processing from subjects can further reveal more complex diagnostic pathways and identify potential therapeutic pathways.

In specific examples, the invention(s) can be used to provide improved outcomes for patients with one or more of: cardiovasular and cardiometabolic disorders (e.g., hypertension, high LDL cholesterol, low HDL cholesterol, high triglycerides, etc.); insulin-related health conditions (e.g., type 2 diabetes, other forms of diabetes, prediabetes, polycystic ovary syndrome (PCOS), etc.); obesity or another overweight condition; chronic pain (e.g., joint pain including persistent joint aches and joint swellings, osteoarthritis, gout, rheumatoid arthritis, headaches, etc.); digestive health issues (e.g., irritable bowel syndrome (IBS), inflammatory bowel disease (IBD), acid reflux, gastroesophageal reflux disease (GERD), functional gastrointestinal disorders (FGIDs) such as functional constipation, functional diarrhea, bloating, etc.); skin health conditions (e.g., rashes/ dryness, itching, hair loss, acne, rosacea, eczema, atopic dermatitis, psoriasis, alopecia, etc.); mental health conditions (e.g., anxiety, depression, autism, bipolar disorder, memory loss, brain fog, cognitive functions, etc.); sleep issues (e.g., sleep apnea, disturbed sleep, fatigue, etc.); renal disorders (e.g., kidney stones, renal failure, etc.); non-alcoholic fatty liver disease (NAFLD); hormonal health conditions (e.g., hyperthyroidism, hypothyroidism, menopause, altered testosterone levels, etc.); and/or other conditions.

In specific applications, the platform and methods described can be used for prevention and/or treatment of cardiovascular conditions.

In specific applications, the platform and methods described can be used for prevention and/or treatment of digestive conditions. The invention(s) include systems and/ or model architecture for characterizing and improving health statuses of subjects with FGID symptoms, using demographic, genetic, microbiome data, and other contextual data. Additionally, the inventions aim at modeling changes in FGID symptom severity of subjects simultaneously with achieving unprecedented levels of body weight loss in a digital therapeutics care program compared to baseline symptom severity. In more detail, embodiments, variations, and examples of a digital therapeutics program, informed by outputs of models structured to process genomic loci of interest (SNPs), gut microbiome information, and interactions with participant diet, demographics, and lifestyle, were used to classify and achieve significant reductions in functional bowel disorder symptomatology in comparison to non-treatment groups. The methods and models disclosed herein can readily be implemented to study other comorbidities where genetics and gut microbiome also play a central role in disease etiology.

The invention(s) also confer the benefit of providing improved methods and systems for generation of diagnostic and therapeutic signatures from multi-omic data. Diagnostic signatures (described in more detail below) are returned by data transformation architecture, and in embodiments, can be indicative of decreased/increased likelihood of developing a health condition. Therapeutic signatures (described in more detail below) are returned by data transformation architecture and in embodiments, can be indicative of decreased/increased likelihood of improvement or remission of a health condition.

The invention(s) also confer the benefit of applying model outputs generated upon processing such signatures to develop new pharmaceutical, nutraceutical, skinceutical, and/or other compositions, including but not limited to chemical compositions (e.g., small molecule modulators) and biological compositions (e.g., pre-/pro-/syn-/post-biotics).

Additionally, in embodiments, the invention(s) described implement rapid processing of samples and data generated from sample processing, in order to detect presence of biomarkers from patients, and extract insights for diagnostic and therapeutic applications, in a manner that cannot be practically performed in the human mind.

Additionally, the inventions apply outputs of the analyses to effect one or more actions (e.g., therapeutic pathways) for improvement of patient health statuses and outcomes.

Additionally, the invention(s) involve collection of samples from patients and processing of other contextual data (e.g., behavior data, lifestyle-associated data), processing of samples to extract signatures, application of one or more transformations to the signatures to generate modified digital objects, create improved training data sets for machine learning/classification algorithms, and iteratively train the machine learning/classification algorithms, such that patient statuses can be returned upon processing subsequent samples hitherto unseen by the algorithm. Additionally, in embodiments, the invention(s) described implement rapid processing of samples and data generated from sample processing, in order to extract insights related to contributing factors to subject health, and rapid generation of personalized care program components, in a manner that cannot be practically performed by the human mind.

Additionally, the invention(s) include a platform for coordinating sampling from patients, processing of samples, generating multi-omic signatures from sample processing, returning insights upon processing multi-omic signatures with trained models, and applying therapeutic pathways for patients in a customized manner, by way of an application environment (e.g., mobile application environment, web application environment, etc.), coaching, and/or connected devices.

Additionally or alternatively, the invention(s) can confer any other suitable benefit.

1.1 Definitions

Multi-omics Intervention as a diagnostic approach combines one or more of: genome factors, microbiome factors, lifestyle factors, clinical markers, and other factors.
The multi-omics approach described herein allows identification of diagnostic and therapeutic signatures in patients and/or other subjects.

The term "microbiome", as used herein, refers to the ecological community of commensal, symbiotic, or pathogenic microorganisms in a sample.

The terms microbiome, microbiome information, microbiome data, microbiome population, microbiome panel and similar terms are used in the broadest possible sense, unless expressly stated otherwise, and would include: a census of currently present microorganisms, both living and non-living, which may have been present previously; a census of components of the microbiome other than bacteria and archaea (e.g., viruses, microbial eukaryotes, etc.); population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

Gut flora (e.g. gut microbiota, gastrointestinal microbiota, etc.) is the complex community of microorganisms that live in the digestive tracts of humans and other animals, including insects. Gut metagenome is the aggregate of all the genomes of gut microbiota.

As used herein, terms real-time microbiome data or information includes microbiome information that is collected or obtained at a particular stage of the preventive or curative care of an individual.

As used herein, the terms derived microbiome information and derived microbiome data are to be given their broadest possible meaning, unless specified otherwise, and includes any real-time, microbiome information that has been computationally linked or used to create a relationship.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition, or allows interpretation of a current or past occurrence.

Real time, derived, and predicted data can be collected and stored, and thus, become historic data for ongoing or future decision-making for a process, setting, or application.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with genetic material, cDNA, and mRNA encoded by a gene.

Reference to "DNA region" should be understood as a reference to a specific section of DNA. These DNA regions are specified either by reference to a gene name, a set of chromosomal coordinates or Reference single nucleotide polymorphisms (SNPs). Both the chromosomal coordinates and the gene or genomic region would be well known to, and understood by, the person of skill in the art. In general, a gene or genomic region can be routinely identified by reference to its name, via which both its sequences and chromosomal location can be routinely obtained, or by reference to its chromosomal coordinates, via which both the gene or genomic region name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation. Allelic variations encompass single nucleotide polymorphisms, insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations may exist between the actual nucleic acid sequences may exist between different individuals of the same species (e.g., between different human subjects) or across different species (e.g., between different bacterial strains). The present invention should therefore be understood to extend to all forms of DNA which arise from any other mutation, polymorphic or allelic variation.

The term "sequencing" as used herein refers to sequencing methods for determining the precise order of the nucleotide bases—adenine, guanine, cytosine, and thymine—in a nucleic acid molecule (e.g., a DNA or RNA nucleic acid molecule). It includes any method or technology that is used to determine the order of the four bases—adenine, guanine, cytosine, and thymine—in a strand of DNA. The advent of rapid DNA sequencing methods has greatly accelerated biological and medical research and discovery.

The term "barcode" as used herein, refers to any unique, non-naturally occurring, nucleic acid sequence that may be used to identify the originating source of a nucleic acid fragment.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

2. METHODS FOR MULTI-OMIC INTERVENTIONS AS DIAGNOSTICS

As shown in FIG. 1A, an embodiment of a method 100 includes (for each of a set of subjects): receiving one or more samples from the subject S110; receiving a biometric dataset from the subject S120; receiving a lifestyle dataset from the subject S130; returning a baseline state and a set of signatures (e.g., including diagnostic signatures and/or therapeutic signatures) upon processing the one or more samples, the biometric dataset, and the lifestyle dataset with a set of transformation operations S140; generating a personalized intervention plan for the subject upon processing the baseline state and the set of signatures with a multi-omic model S150; and executing the personalized intervention plan for the subject S160.

Figure 1B:
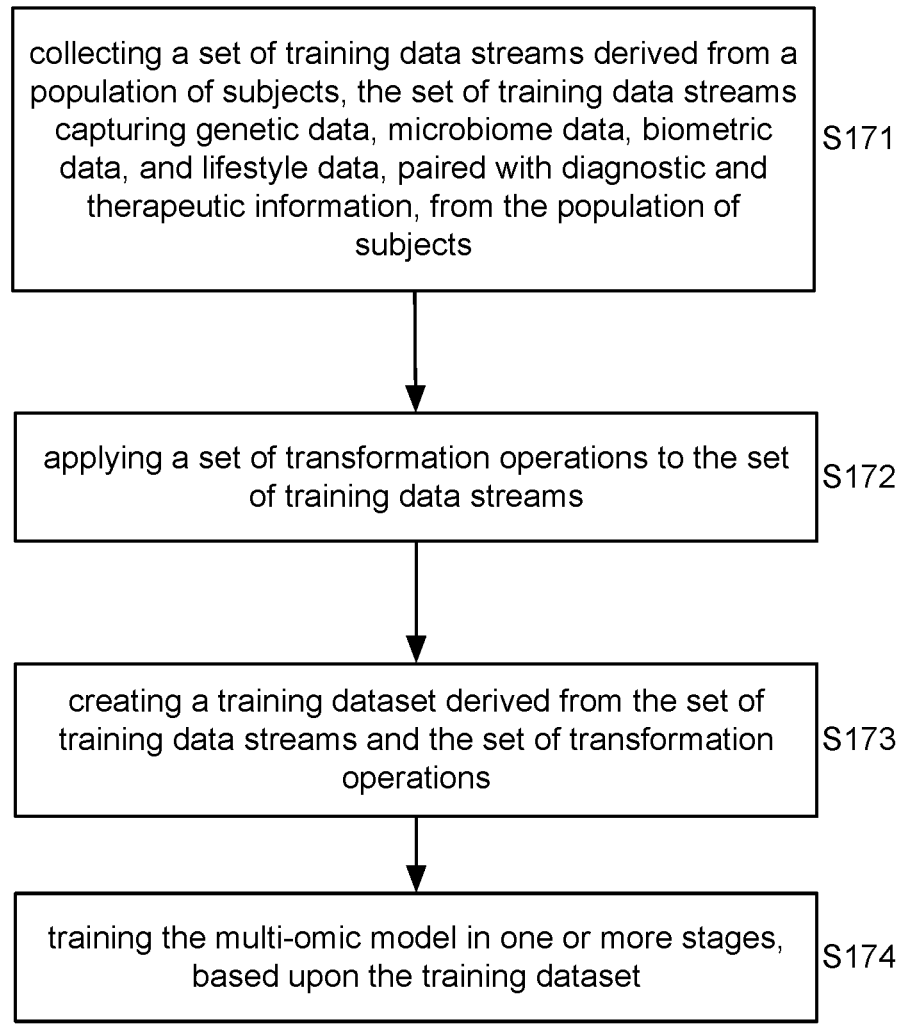
FIG. 1B depicts an embodiment of training of the multi-omic models used in a workflow of a method for obtaining diagnostic and therapeutic signatures of a subject.

In some variations, as shown in FIG. 1B, the method 100 can further include refining the multi-omic model S170, wherein refining the multi-omic model includes: collecting a set of training data streams derived from a population of subjects, the set of training data streams capturing genetic data, microbiome data, biometric data, and lifestyle data, paired with diagnostic and therapeutic information, from the population of subjects S171, applying a set of transformation operations to the set of training data streams S172, creating a training dataset derived from the set of training data streams and the set of transformation operations S173, and training the multi-omic model in one or more stages, based upon the training dataset S174.

Figure 1C:
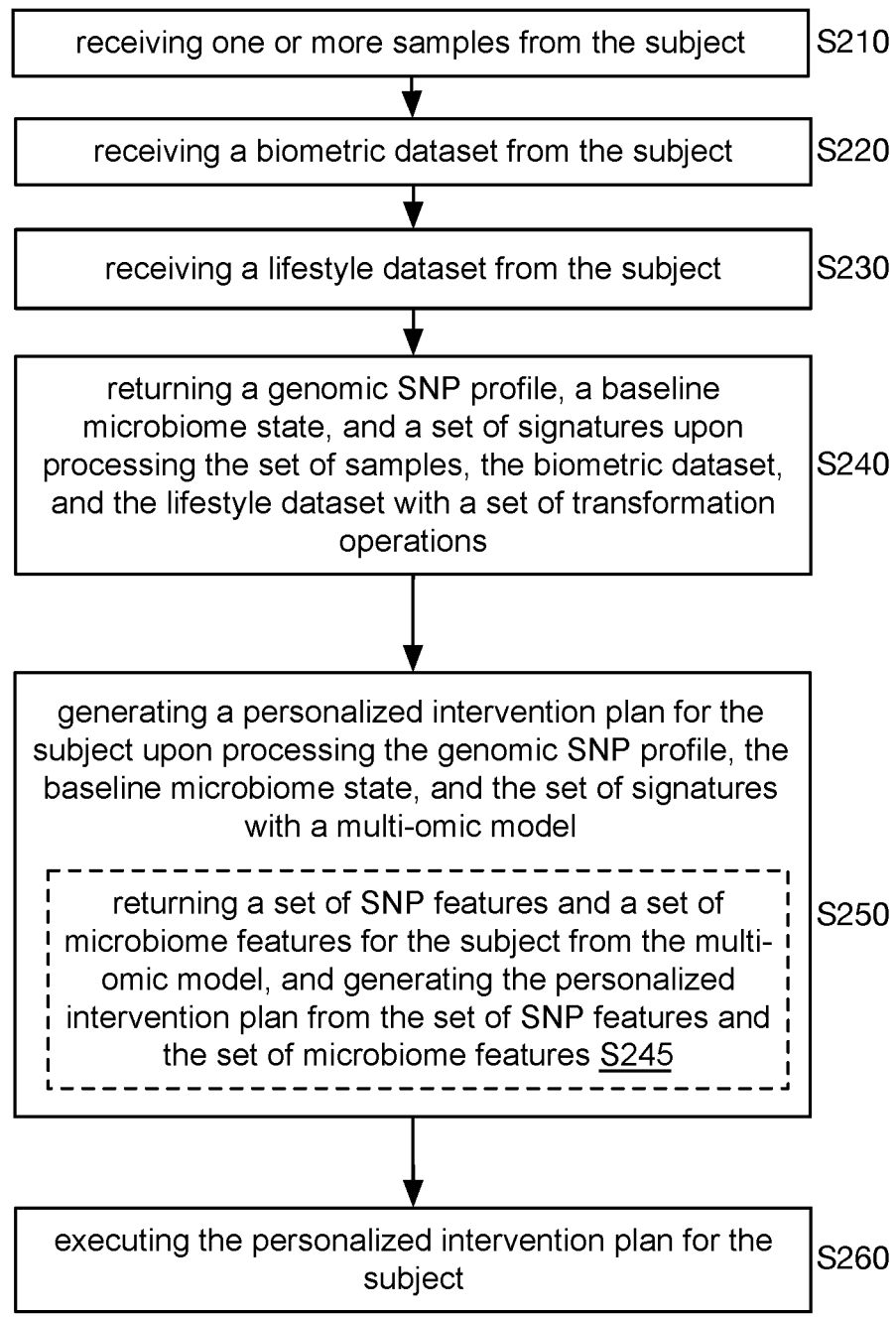
FIG. 1C depicts a variation of a workflow of a method for preventing and/or treating cardiovascular conditions based on multi-omic models, and executing a personalized intervention plan.

In some variations, as shown in FIG. 1C, a method 200 for prevention and/or treatment of a cardiovascular condition can include: simultaneously reducing severity of a set of cardiovascular symptoms, reducing hemoglobin A1c levels, and/or producing significant weight loss in a subject upon: receiving a set of samples from the subject S210; receiving a biometric dataset from the subject S220; receiving a lifestyle dataset from the subject S230; returning a genomic profile, a baseline microbiome state, and a set of signatures upon processing the set of samples, the biometric dataset, and the lifestyle dataset with a set of transformation operations S240; generating a personalized intervention plan for the subject upon processing the genomic SNP profile, the baseline microbiome state, and the set of signatures with a multi-omic model S250; and executing the personalized intervention plan for the subject S260. In variations, the method 200 can include returning a set of genomic features and a set of microbiome features for the subject from the multi-omic model, and generating the personalized intervention plan from the set of genomic features and the set of microbiome features S245.

Figure 1D:
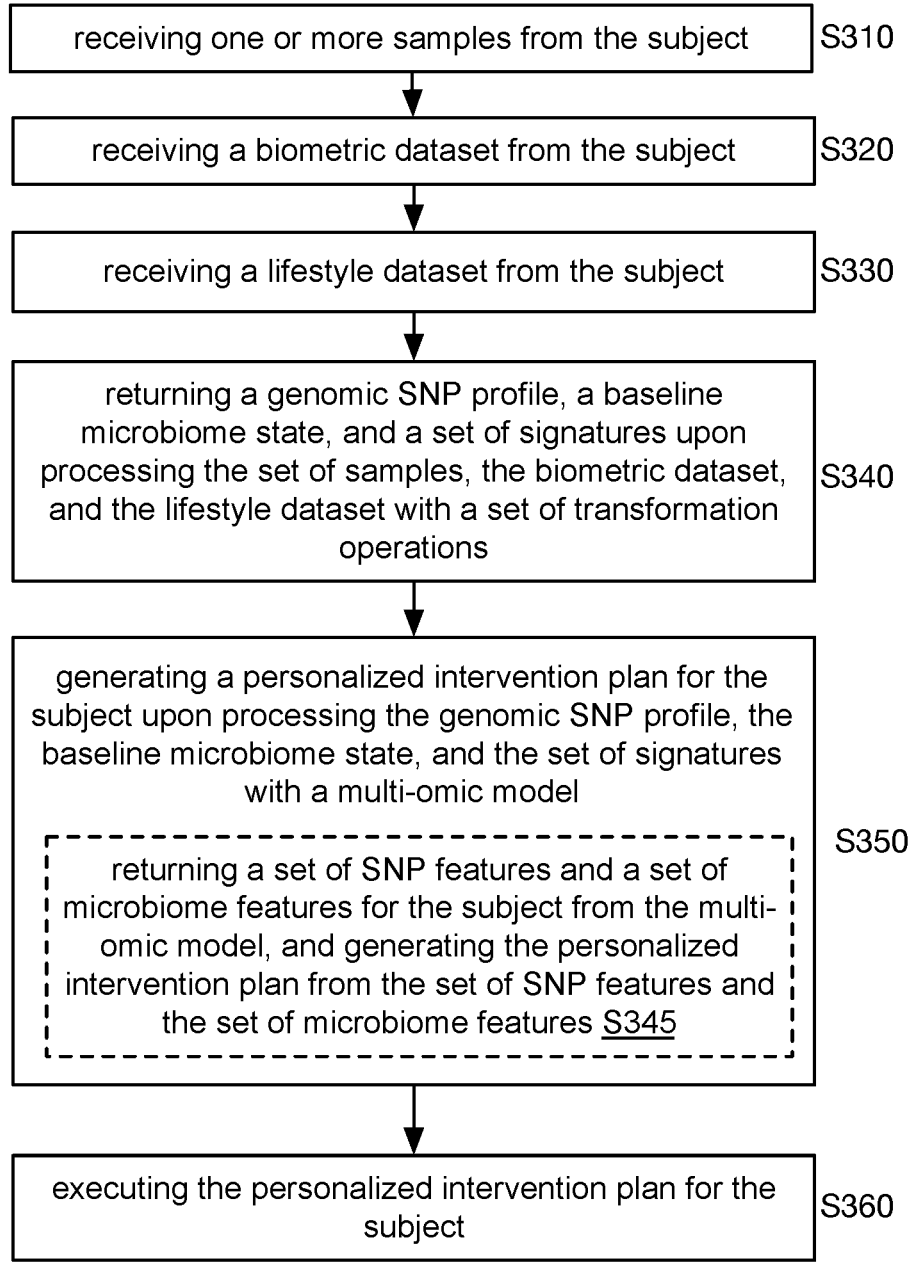
FIG. 1D depicts a variation of a workflow of a method for preventing and/or treating digestive health conditions based on multi-omic models, and executing a personalized intervention plan.

In some variations, as shown in FIG. 1D, a method 300 for prevention and/or treatment of a digestive condition can include: simultaneously reducing severity of a set of digestive disorder and comorbid condition symptoms and producing significant weight loss in a subject upon: receiving a sample from the subject S310; receiving a biometric dataset from the subject S320; receiving a lifestyle dataset from the subject S330; returning a genomic profile, a baseline microbiome state, and a set of signatures of the subject upon processing the set of samples, the biometric dataset, and the lifestyle dataset with a set of transformation operations S340; generating a personalized intervention plan for the subject upon processing the baseline state, the set of signatures with a multi-omic model S350; and executing the personalized intervention plan for the subject S360. In variations, the method 300 can include returning a set of genomic features and a set of microbiome features for the subject from the multi-omic model, and generating the personalized intervention plan from the set of genomic features and the set of microbiome features S345.

Embodiments, variations, and examples of the method 100 function to generate multi-omic (i.e., genomic, microbiome analysis-based, behavior-based, lifestyle-based, clinical marker-based, etc.) diagnostics and therapeutic pathways for precision care (e.g., prevention, diagnosis, and/or treatment) in response to various indications. The method 100 can generate multi-omic signatures (e.g., from individual biomarkers or combinations of genetic biomarkers, microbiome biomarkers, lifestyle biomarkers, etc.), in order to generate diagnostics and therapeutic pathways for subjects in a personalized manner. As such, the method 100 can improve patient outcomes with respect to various health states and indications, thereby addressing impacts on healthcare systems with personalized preventive and curative healthcare approaches in an improved manner.

Variations of the methods described can be implemented for different subject types, different demographics, different health states, different lifestyles, and/or other factors (e.g., social determinants of health, work determinants of health, familial determinants of health, etc.), with specific applications for improving health statuses in relation to various conditions and indications described in more detail below.

Furthermore, in downstream applications, refinement of models, system architecture, and sample processing techniques can be used to guide testing of, recommendation of, and/or implementation of (e.g., using automated or manual systems/devices) therapeutic interventions in order to improve desired outcomes (e.g., in relation to patient adherence to regimens, in relation to patient engagement, in relation to remission and reduction of comorbidities, etc.). As such, the method(s) can provide steps for monitoring, controlling, and analyzing patient data and lifestyles, with practical applications in personalized preventive and curative care across a wide range of conditions.

The method(s) described can be implemented by systems and platforms described in Section 3 below.

2.1 Methods—Sample, Biometrics, and Lifestyle Data Extraction 2.1.1 Sampling

Block S110 recites: receiving one or more samples from the subject, which functions to enable generation of a baseline state and one or more signatures from which models for returning diagnostics and personalized therapeutic pathways can be generated in subsequent portions of the method 100. In Block S110, samples can be retrieved from the subject (or each of a population of subjects) in a non-invasive manner. In variations, non-invasive manners of retrieving the one or more samples can implement one or more of: an absorbent material (e.g., a swab, a sponge, etc.), a non-absorbent material (e.g., a slide, etc.), a container (e.g., vial, tube, bag, etc.) configured to receive a sample from a region of a subject's body, and any other suitable sample-receiver. In variations, samples can be collected from one or more of a subject's mouth (e.g., a saliva sample), genitals, nose, skin, gut (e.g., through a stool sample, through a fecal sample, etc.) in a non-invasive manner. However, one or more samples can additionally or alternatively be received in a semi-invasive manner (e.g., glucose monitor, dry blood spots, etc.) or an invasive manner (e.g., blood sample, biopsy sample, etc.).

In above variations and examples, samples can be taken from the bodies of subjects without facilitation by a healthcare entity or another entity. In one example, a sampling kit can be provided to a subject, where the sampling kit facilitates self-sampling of genetic and/or microbiome samples from the subject. The sampling kit can further provide devices configured to facilitate reception of the biometric dataset and the lifestyle dataset from the subject in subsequent method blocks. The sampling kit can further include instructions for sample provision and setup of a user account within a platform for providing insights and care, elements configured to associate the sample(s) with the subject (e.g., barcode identifiers, tags, etc.), and a receptacle that allows the sample(s) from the subject to be delivered to a sample processing operation (e.g., by a mail delivery system). In another example, wherein samples are extracted from the user with the help of another entity, one or more samples can be collected in a clinical or research setting from a subject.

Samples can be collected once (e.g., at a single time point), or at a number of time points (e.g., at random points, at regular points, in relation to triggering events, with other frequency, etc.).

In expanded versions of Block S110 (e.g., with respect to generation of training and test datasets for model refinement in other portions of the method 100), samples can be retrieved from a wide variety of subjects with various conditions, demographics, and/or lifestyles, and can involve samples from human subjects and/or non-human subjects. In relation to human subjects, Block S110 can include receiving samples from a wide variety of human subjects, collectively including subjects of one or more categories such as: demographics (e.g., genders, ages, marital statuses, ethnicities, nationalities, socioeconomic statuses, sexual orientations, etc.), health conditions (e.g., health and disease states), living arrangements (e.g., living alone, living with pets, living with a significant other, living with children, etc.), environmental exposures (e.g. exposure to heavy metals, pesticides, xenobiotics etc.), dietary habits (e.g., omnivorous, vegetarian, vegan, sugar consumption, acid consumption, etc.), lifestyle tendencies (e.g., levels of physical activity, drug use, alcohol use, etc.), levels of activity, analyte states (e.g., cholesterol levels, lipid levels, hormone levels, etc.), weight, height, body mass index, genotypic factors, and any other suitable category.

Additionally or alternatively, receiving samples can include receiving samples from a targeted group of similar subjects to the subject, based on family relationships (e.g., twin relationships, triplet relationships, quadruplet relationships, etc., parental relationships, offspring relationships, etc.), subjects cohabiting with the subject, or subjects associated with the subject by other relevant linkages.

However, receiving the samples in Block S110 can additionally or alternatively be performed in any other suitable manner. Furthermore, some variations of the first method 100 can omit Block S110, or acquire sample data in another suitable manner.

2.1.2 Biometrics

Block S120 recites: receiving a biometric dataset from the subject, which further functions to enable generation of a baseline state and one or more signatures from which models for returning diagnostics and personalized therapeutic pathways can be generated in subsequent portions of the method 100.

In variations, the biometric dataset can include data derived from one or more of: body weight (e.g., receiving bodyweight values of the subjects generated from a digital weighing scale), body fat percent, muscle mass, body water, height or other length measurements (e.g., via a ruler or measuring tape), other body mass index (BMI)-associated parameters, gastrointestinally-derived signals, Bristol stool scores, stool frequency, abdominal pain intensity, blood chemical and biochemical information, inflammatory markers, fasting blood sugar, high density lipids, low density lipids, fecal calprotectin, blood interleukins, c-reactive protein, blood cell counts, sleep-associated signals, electrophysiology signals (e.g., electroencephalogram signals, electromyography signals, galvanic skin response signals, electrocardiogram signals, etc.), heart rate, body temperature, cardiovascular parameters, continuous glucose monitoring (glycemic response), respiration parameters (e.g., respiration rate, depth/shallowness of breath, etc.), blood oxygenation signals, motion parameters, and any other suitable physiologically relevant parameter of the subject.

In examples, the biometric dataset can include data derived from one or more of: blood chemical and biochemical profiles, medication use, fasting blood sugar, glycemic response, high density lipid values, and low density lipid values.

Additionally or alternatively, the biometric dataset can include or otherwise detect cyclic biometrics or biometrics that occur with some pattern (e.g., derived from user inputs, biometric monitoring devices worn by the user, or determined by an algorithm that tracks the user's physical, emotional, or neurological states).

As described above, the sampling kit that facilitates self-sampling of genetic and/or microbiome samples from the subject can further include devices configured to facilitate reception of the biometric dataset. In specific examples, the sampling kit can include one or more of: a weighing scale (e.g., a connected weighing scale), a fitness tracking device, an ingestible device (e.g., smart pill, gastric balloon, etc.), a wearable computing device, a wearable biometric sensor (e.g., analyte sensor, cardiovascular parameter sensor, respiratory parameter sensor, neurological signal parameter sensor, activity sensor, etc.), or other device configured to facilitate reception of the biometric dataset. Furthermore, the sampling kit can provide instructions or otherwise facilitate linking of any devices provided with the account of the subject.

The biometric dataset of Block S120 can include data sampled from devices once (e.g., at a single time point), or at a number of time points (e.g., at random points, at regular points, in relation to triggering events, with other frequency, etc.).

The biometric dataset can, however, be received in another manner or using other suitable devices.

2.1.3 Lifestyle Aspects

Block S130 recites: receiving a lifestyle dataset from the subject, which functions to enable generation of a baseline state and one or more signatures from which models for returning diagnostics and personalized therapeutic pathways can be generated in subsequent portions of the method.

In variations, the lifestyle dataset captures behavioral information for the subject pertaining to one or more of: energy levels (e.g., morning energy level, evening energy level, daytime energy level, etc.), dietary behavior, sleep behavior, stress levels, stress-associated events, cravings, exercise behavior, meditation behavior, perceived progress toward a health-associated goal, actual progress toward a health-associated goal, state of symptoms, social determinants of health, familial determinants of health, and work determinants of health, and/or other behavioral information. In examples, the lifestyle dataset can capture one or more of the following lifestyle characteristics of the subject: energy levels, food intake (e.g. through food photos which are then assessed and scored by a coaching entity or other entity, through dietary journal entries, through application programming interfaces (APIs) of diet-monitoring applications, etc.), sleep behavior, stress levels, cravings, exercise behavior, and weight loss progress. However, variations of the example can alternatively capture other types of lifestyle information from the subject.

In further examples, the lifestyle dataset can capture one or more of: a morning energy level, dietary behavior, sleep behavior, stress levels, cravings, exercise behavior, meditation behavior, state of symptoms of the subject, medication use, social determinants of health, familial determinants of health, and work determinants of health.

As described above, the sampling kit that facilitates self-sampling of genetic and/or microbiome samples from the subject can further include elements configured to facilitate reception of the lifestyle dataset. In specific examples, the sampling kit can include instructions for or otherwise provide access to a tool for receiving self-report data from the user pertaining to the lifestyle dataset. Additionally or alternatively, the sampling kit can include functionality for linking personal/protected information and/or accounts of the user (e.g., within social media platforms, within health tracking platforms, etc.) with the account of the subject associated with the platform (in a secure manner), such that aspects of the lifestyle dataset can be populated in a more automated manner.

In variations, the components of the lifestyle dataset can be retrieved once (e.g., upon intake of the subject); however, the components of the lifestyle dataset can alternatively be retrieved at a number of time points (e.g., at random points, at regular points, in relation to triggering events, with other frequency, etc.).

2.1.4 Other Relevant Datasets

While types of data are described in Blocks S110-S130, the method 100 can additionally or alternatively include retrieval of other supplemental or contextual data relevant to generating actionable insights in subsequent blocks of the method 100. For instance, the method 100 can include capture of current therapeutic approaches the subject participates in (e.g., existing medications, existing supplements, etc.), trends in usage or adherence to current therapeutic approaches the subject participates in (e.g., increasing use, decreasing use, steady use, etc.), medical history, family medical history, and/or other information. Additionally or alternatively, additional data can include information related to an environment of the user, such as a location of the user (e.g., as determined from a global positioning device, from a triangulation device), environmental temperature of the user, environmental audio of the user, and any other suitable environmental information of the user pertaining to potential stimuli affecting health, and/or environmental devices that can be used for therapeutic outputs associated with subsequent blocks of the method.

2.2 Methods—Sample and Data Processing

Block S140 recites: returning a baseline state and a set of signatures (e.g., diagnostic and/or therapeutic signatures associated with genomic and demographic features of the subject) upon processing the one or more samples, the biometric dataset, and the lifestyle dataset with a set of transformation operations. Block S140 functions to process samples and transform data from Blocks S110-S130 into various signatures that can be used to characterize the subject and to generate a personalized intervention plan for the subject based upon the characterization of the subject.

In examples, transformation operations can include one or more of: demultiplexing, generating amplicon sequence variants (ASVs), performing taxonomic and functional annotation of the set of sequencing reads based on at least one of local and global alignment methods, and graph-based methods, linear and nonlinear dimensionality reduction, applications of supervised, semi-supervised and unsupervised machine or statistical inference methods to derive informative features from the microbiome profiles, imputing missing sites, determining genetic ancestry of the subject, estimating genetic parameters comprising genetic diversity and homozygosity, estimating scores representing inherited risk, and estimated values of qualitative, continuous and categorical traits which are normalized to biological gender, genetic ancestry, age, socioeconomic status, biometric measurements and life-style variables.

Transformation operations are described in further detail below.

2.2.1 Sample Processing

In variations, processing the one or more samples can include any one or more of: sample lysis, disruption of membranes, extraction of DNA, RNA, nucleic acid fragments, other nucleic acid material, separation of non-target material from target material (e.g., RNA, proteins) from the sample, nucleic acid purification, nucleic acid fragmentation, nucleic acid amplification, protein extraction, target material washing, target material retrieval, nucleic acid synthesis (e.g., from captured mRNA), sequencing of amplified nucleic acids, library preparation, labelling using fluorescent dyes, hybridization to probe sequences contained within arrays, scanning of arrays to assess hybridization intensity between probes and targets, single-base extension of probes with labelled nucleotides, and/or other suitable processing steps. Thus, portions of Block S140 can be implemented using embodiments, variations, and examples of the sample handling network and/or computing system described in further detail.

Amplification can implement suitable amplification techniques (e.g., using polymerase chain reaction (PCR)-based techniques, using helicase-dependent amplification (HDA), using loop mediated isothermal amplification (LAMP), using self-sustained sequence replication (3SR), using nucleic acid sequence based amplification (NASBA), using strand displacement amplification (SDA), using rolling circle amplification (RCA), ligase chain reaction (LCR), etc.)). Amplification can implement primers targeted to specific genetic sequences (e.g., human sequences, non-human sequences), in association with generation of diagnostic and therapeutic signatures. Additionally, amplification can be quantitative (e.g. qPCR) such that amplicons (e.g. human sequence, bacterial sequences, fungal sequences, viral sequences, etc.) can be associated with absolute quantification data. Additionally or alternatively, primers used can be designed to mitigate amplification bias effects, as well as configured to amplify and/or sequence nucleic acids (e.g., of the 16S region, the 18S region, the ITS region, viral genetic markers, full metagenomic sequences, transcriptomic sequences, etc.) that are informative from a microbiome perspective.

In specific examples, nucleic acid sequences of interest include V3-V4 regions of 16S RNA; however, other loci of interest (e.g., housekeeping genes that provide taxonomic and/or functional information, insertions, deletions, etc.) can be assessed. Primers used in variations of Block S140 can additionally or alternatively include incorporated barcode sequences, unique molecule identifiers, adaptor sequences, or other sequences specific to each sample and/or in association with sequencing platforms, which can facilitate identification of material derived from individual samples post-amplification.

Furthermore, sequencing can be performed in coordination with a next generation sequencing platform (e.g., Illumina™ sequencing platform) or other suitable sequencing platform (e.g., Oxford nanopore sequencing platform, PacBio platform, etc.). Additionally or alternatively, any other suitable sequencing platform or method can be used (e.g., a Roche 454 Life Sciences platform, a Life Technologies SOLiD platform, etc.). Additionally or alternatively, sample processing can implement any other step configured to facilitate processing in cooperation with amplification, including adding barcodes for multiplexing, unique molecular identifiers, etc.

Processing the one or more samples can include performing an assessment of single nucleotide polymorphisms (SNPs) of the one or more subjects. SNP array processes can be performed in coordination with a high-throughput genotyping platform (e.g. Illumina™ Infinium Global Screening Array). Additionally or alternatively, any other suitable genotyping platform or method can be used (e.g., an Affymetrix® Genome-Wide Human SNP Array, etc.). Additionally or alternatively, sample processing can implement any other step configured to facilitate processing in cooperation with amplification. In specific examples, performing the assessment of SNPs can include characterizing a panel of genomic SNPs from the one or more subjects, where the panel of SNPs can include more than 2 SNPs, more than 3 SNPs, more than 4 SNPs, more than 5 SNPs, more than 6 SNPs, more than 7 SNPs, more than 8 SNPs, more than 9 SNPs, more than 10 SNPs, more than 11 SNPs, more than 12 SNPs, more than 13 SNPs, more than 14 SNPs, more than 15 SNPs, more than 16 SNPs, more than 17 SNPs, more than 18 SNPs, more than 19 SNPs, more than 20 SNPs, or another suitable number of SNPs.

Sample processing can further include operations for detecting allelic variations (e.g., risk alleles) or alleles of interest from the sample(s) of the subject. In variations, alleles of interest can be bi-allelic or multiallelic.

Additionally or alternatively, sample processing for generation of genomic data can include operations for detecting other loci of interest from the sample(s) of the subject.

2.2.2 Signal Processing

With respect to biometric signal acquisition and/or monitoring devices described above, Block S140 can include signal processing operations including one or more of: denoising, filtering, smoothing, clipping, transformation of discrete data points to continuous functions, and performing any other suitable signal conditioning process. For instance, some variations of Block S140 can additionally include performing a windowing operation and/or performing a signal cleaning operation. Signal cleaning can include removal of signal anomalies by one or more filtering techniques. In specific examples, filtering can include one or more of: Kalman filtering techniques, bootstrap filtering techniques, particle filtering techniques, Markov Chain Monte Carlo filtering techniques; and/or another suitable technique. Signal cleaning can thus improve data quality for further processing, in relation to one or more of: noise, sensor equilibration, sensor drift, environmental effects (e.g., moisture, physical disturbance, etc.), and any other suitable type of signal artifact.

2.2.3 Baseline and Signatures

The baseline state functions to establish a reference state against which progress is compared, as the subject participates in the personalized intervention plan generated in subsequent portions of the method 100. The baseline state is preferably associated with a state of the subject (e.g., microbiome baseline state) prior to participation in the personalized intervention plan, such that the baseline state characterizes a state of the subject prior to treatment according to the personalized intervention plan. However, the baseline state can alternatively characterize another suitable state of the subject. Furthermore, the method 100 can include re-establishment of a "baseline" state of the subject in coordination with provision of the personalized intervention plan. As such, the baseline state can be updated as the subject progresses during participation in the personalized intervention plan, at which point the diagnostic and therapeutic signatures may lead the subject into a different personalized intervention plan.

The baseline state can also characterize a physiological state of the subject, with respect to a condition or indication (e.g., health condition, disease state, etc.) described in more detail below. As such, the baseline state can characterize a clinical diagnosis, a laboratory diagnosis, a radiological diagnosis, a tissue diagnosis, a principal diagnosis, an admitting diagnosis, a differential diagnosis, a prenatal diagnosis, a diagnosis of exclusion, and/or other diagnostic criteria. Additionally or alternatively, the baseline state can characterize aspects associated with a condition or indication (e.g., a state of pain, a state of discomfort, etc.). Additionally or alternatively, the baseline state can characterize aspects associated with an emotional state, state of focus, or other cognitive state of the subject.

In some embodiments, the diagnostic signatures generated in Block S140 can include one or more of: genetic signatures, microbiome signatures (e.g., associated with microbial taxonomic features, associated with microbiome functional features, associated with microbial ecological features, etc.), biometrics, and/or lifestyle biomarkers indicative of decreased or increased likelihood of developing a health condition.

In some embodiments, the therapeutic signatures generated in Block S140 can include one or more of: genetic signatures, microbiome signatures (e.g., associated with microbial taxonomic features, associated with microbiome functional features, etc.), biometrics, and/or lifestyle biomarkers indicative of decreased/increased likelihood of improvement or remission of a health condition. The therapeutic signatures can be used to develop new pharmaceutical, nutraceutical or skinceutical compositions based on chemistry (e.g., small molecule modulators), biology (e.g., pre-/pro-/syn-/post-biotics), or any other suitable molecular entity. Additionally or alternatively, the therapeutic signatures can be used in Block S150 to generate the personalized intervention plan, with respect to personalized and combinatorial therapeutic pathways implementing different approaches.

2.2.3.1 Types of Biomarkers

In variations, genetic biomarkers can include or be derived from one or more of: single and multi-genic single nucleotide polymorphism (SNP)-based biomarkers, tandem repeats, indels (insertions and deletions), somatic amplifications, copy number variations (CNVs), translocations, inversions, other genetic features (e.g., mutations, recombinations, immigrations, etc.), imputed genotypes, genetic ancestry, genetic diversity and homozygosity, genetic scores representing inherited risk, and estimated values of qualitative, continuous and categorical traits which could be normalized to biological gender, genetic ancestry, age, socioeconomic status, biometric measurements and life-style variables, and/or other types of genetic biomarkers. In examples, SNP-based biomarkers are curated from one or more of: genome-wide association studies (GWAS), public repositories and other scientific literature, including allele frequency, odd ratios or beta coefficients for a particular impact on a phenotype, p-values or other statistical values, and study cohort size. Based on these data sources, single gene or multigenic/polygenic trait risk index scores are obtained either by weighted or unweighted scoring (depending on availability of odd ratios or beta coefficients). Risk indices for each trait are then used for defining interventions. Panels of traits can be configured to include 1 trait (e.g., as in a pico report), 2-4 traits (e.g., as in a nano report), 5-10 traits (e.g., as in a micro report), >10 traits (e.g., as in a macro report). Example macro reports include: nutrition report, fitness report, allergy report, skin health report, gut health report, mental health report, sexual health report, sleep report, cardiometabolic report, hormonal health report, and musculoskeletal health report. Example traits include zinc needs (e.g., based on SNPs on genes CA1, PPCDC and NBDY), vitamin K needs (e.g., based on SNPs on genes CYP4F2 and KVKORC1), vitamin E needs (e.g., based on SNPs on genes ZPR1, CYP4F2, TTPA and CD36), vitamin D needs (e.g., based on SNPs on genes CYP2R1, GC and NADSYN1), vitamin C needs (e.g., based on SNPs on gene SLC23A1), vitamin B9 needs (e.g., based on SNPs on genes MYT1L and MTHFR), vitamin B6 needs (e.g., based on SNPs on genes NBPF3 and ALPL), vitamin B12 needs (e.g., based on SNPs on genes FUT2, CUBN and TCN1), vitamin A needs (e.g., based on SNPs on gene BCMO1), selenium needs (e.g., based on SNPs on genes DMGDH and CBS), phosphate needs (e.g., based on SNPs on genes RGS14 and C12orf4), magnesium needs (e.g., based on SNPs on genes DCDC5, PRMT7, ATP2B1, MUC1, SHROOM3 and TRPM6), iron needs (e.g., based on SNPs on genes TMPRSS6, TRF2 and TF), cooper needs (e.g., based on SNPs on genes SIMM1 and SELENBP1), choline needs (e.g., based on SNPs on genes PEMT and MTHFD1), calcium needs (e.g., based on SNPs on gene CASR), anti-oxidant needs (e.g., based on SNPs on genes PON1, CAT, CYP1A2, GSTP1, NQO1, SOD2, NAT2 and GPx1P1), tendency to regain weight (e.g., based on SNPs on genes PPARG, TFAP2B, ADIPOQ and BDNF), tendency to prefer sweet foods (e.g., based on SNPs on genes FGF21, SLC2A2, TAS1R2 and TAS1R3), tendency to prefer fatty foods (e.g., based on SNPs on gene CD36), tendency to prefer bitter foods (e.g., based on SNPs on gene TAS2R38), tendency to overeat (e.g., based on SNPs on genes MC4R, TAS2R38 and FTO), tendency to gain weight (e.g., based on SNPs on genes SH2B1, KCTD15, SEC16B, MC4R, MTCH2, TMEM18, STK33, ETV5, BDNF, FTO, NEGR1 and ADIPOQ), saturated fats intake and weight gain tendency (e.g., based on SNPs on genes FTO and APOA2), protein intake and weight loss tendency (e.g., based on SNPs on gene FTO), poly-unsaturated fats intake and weight gain tendency (e.g., based on SNPs on gene BDNF and FADS), mono unsaturated fats intake and weight gain tendency (e.g., based on SNPs on genes ADIPOQ and PPARG), carbohydrate intake and weight gain tendency (e.g., based on SNPs on genes LRRN6C, FAIM2, FLJ35779, FTO, RBJ and SEC16B), salt intake and blood pressure sensitivity (e.g., based on SNPs on genes AGT and NPPA), riboflavin and blood pressure response (e.g., based on SNPs on gene MTHFR), lactose intolerance (e.g., based on SNPs on genes LCT and MCM6), gluten sensitivity (e.g., based on SNPs on genes HLA-DQ2.5 and HLA-DQ8), milk allergy (e.g., based on SNPs on gene TLR6 and IL2), peanut allergies (e.g., based on SNPs on gene HLA-DRA, STAT7 and LOC100507686), histamin intolerance (e.g., based on SNPs on gene AOC1, HNMT and LOC105375567), cockroach allergy (e.g., based on SNPs on gene IL12A), dust mites allergy (e.g., based on SNPs on gene C11orf30, TSLP, GSDMA, IL1RL1 and HLA-DQB1-AS1), pets allergy (e.g., based on SNPs on gene HLA-DQB1), hay fever (e.g., based on SNPs on gene IL1RL1, GSDMA, CLEC16A, WDR36, LRRC32, SMAD3, ZBTB10, TSLP, IL33 and HLA-DQB1), pollen allergy (e.g., based on SNPs on gene HLA-DQB1, TLR1, IL1RL1, GSDMA, TSLP and LRRC32), grass allergy (e.g., based on SNPs on gene ABL2, DNAH5, EPS15, LRRC32 and genes within the HLA), caffeine metabolism (e.g., based on SNPs on gene CYP1A2), caffeine consumption (e.g., based on SNPs on genes MLXIPL, GCKR, CYP1A2, AHR, ABCG2 and EFCAB5), alcohol flush (e.g., based on SNPs on gene ALDH2), weight loss or weight gain with exercise (e.g., based on SNPs on gene FTO), likelihood of injury (e.g., based on SNPs on genes COL5A1, MMP3, ESR1, ACTN3, MCT1 and IGF2), likelihood of fatigue (e.g., based on SNPs on gene MCT), insulin sensitivity with exercise (e.g., based on SNPs on gene LIPC), HDL cholesterol levels with exercise (e.g., based on SNPs on gene PPARD), exercise recovery (e.g., based on SNPs on gene TNF), exercise motivation (e.g., based on SNPs on gene BDNF), tendon strength (e.g., based on SNPs on genes COL5A1, COL1A1 and GDF5), power (e.g., based on SNPs on genes ACTN3, COTL1, MPRIP, CALCR, MSTN and PPARA), lung capacity (e.g., based on SNPs on genes TTC6 and an intergenic region), ligament strength (e.g., based on SNPs on genes MMP3 and COL1A1), heart capacity (e.g., based on SNPs on genes MYH6, CD46 and KIAA1755), hand grip strength (e.g., based on SNPs on genes GLIS1, HOXB3, Dec1, GBF1, MGMT, SYT1, HLA, KANSL1 and TGFA), flexibility (e.g., based on SNPs on gene COL5A1), endurance (e.g., based on SNPs on genes BDKRB2, ACTN3, ADRB3, AMPD1 and IL6), aerobic capacity (e.g., based on SNPs on genes NFIA-AS2, TSHR, ESRRB, PPARA and CREB1), and/or other traits.

In variations, the panel of SNPs can include SNPs associated with one or more of: with lactose intolerance, gluten sensitivity, milk and peanut allergies, caffeine metabolism, and inflammatory markers such as tumor necrosis factors (TNFs), interleukins (e.g., ILs), C-reactive proteins (CRPs), or other inflammatory markers. In specific examples, SNPs of the panel associated with caffeine metabolism can include one or more of: rs2472297 (risk allele C) and/or rs762551 (risk allele C) associated with gene CYP1A2; SNPs of the panel associated with gluten sensitivity can include one or more of: rs2187668 (risk allele T) associated with gene HLA-DQ 2.5, rs2395182 (risk allele T) associated with gene HLA-DQ 2.2 (M1), rs4639334 (risk allele A) associated with gene HLA-DQ7; rs4713586 (risk allele G) associated with gene HLA-DQ 2.2 (M3), rs7454108 (risk allele C) associated with gene HLA-DQ8, and/or rs7775228 (risk allele C) associated with gene HLA-DQ 2.2; SNPs of the panel associated with lactose intolerance can include one or more of: rs182549 (risk allele C) associated with gene MCM6 and/or rs4988235 (risk allele G) associated with gene MCM6; SNPs of the panel associated with dairy allergies can include one or more of: rs324015 (risk allele T) associated with gene STAT6; SNPs of the panel associated with peanut allergies can include one or more of: rs7192 (risk allele T) associated with gene HLA-DRA and/or rs9275596 (risk allele C) associated with gene MTCO3P1-AL662789.1; SNPs of the panel associated with inflammation can include one or more of: rs1800629 (risk allele A) associated with gene TNF, rs1800896 (risk allele T) associated with gene IL10, and/or rs3024496 (risk allele G) associated with gene IL10.

However, the panel of SNPs can additionally or alternatively include other SNPs, other risk alleles, and/or other loci, associated with other genes of interest.

SNPs can include SNPs having a desired minor allele fraction (MAF) for discrimination between non-risk and risk alleles. The MAF can be greater than 0.2, 0.3, 0.4, 0.5, 0.6, 0.7, 0.8, or 0.9. SNPs evaluated can be for coding regions (e.g., synonymous, non-synonymous, missense, nonsense) and/or non-coding regions. SNPs evaluated can be biallelic or multiallelic, with more than two alleles per SNP. Furthermore, SNPs selected for evaluation can have allele pairs that are well-discriminated (e.g., with respect to stabilization or destabilization characteristics). For instance, SNPs can be selected with prioritization of G/T, C/A, and T/A SNPs having high destabilization strength characteristics. The size of the SNP panel being evaluated, threshold MAF for each SNP, and distribution can thus be selected to optimize or otherwise increase the probability of returning an accurate model output in subsequent portions of the embodiments, variations, and examples of the method 100 described. In examples described below, trained models can return output combinations of SNP biomarkers having high predictive power in relation to one or more of: FGID, IBS, Constipation, Diarrhea, and/or other conditions.

In variations, microbiome biomarkers can be derived based on annotation methods that utilize one of local and global sequence alignment, graph-based (network) methods, linear and non-linear dimensionality reduction, and applications of supervised, semi-supervised and unsupervised machine or statistical inference methods using compositionally transformed and arithmetically transformed values from microbial taxonomic and functional abundances and can include one or more of: taxonomic features (e.g., based on operational taxonomic units (OTUs), based on amplicon sequence variants (ASVs), etc.); probiotic features (e.g., single strains associated with health outcomes), consortia biomarkers (e.g., derived from leveraging artificial intelligence to identify bidirectional links between bacteria in human ecological niches, in order to understand which microorganisms co-occur with or do not co-occur with others to define consortia, etc.); prebiotic biomarkers (e.g., specific fiber types, functionality of specific fibers with respect to taxonomies represented in the gut microbiome, etc.); synbiotic features (e.g., combinations of pro- and pre-biotic features, etc.); microbiome functional features, (e.g., postbiotic biomarkers, such as proteins or metabolites from microorganisms, other metabolic features, other functional features, etc.); and/or other types of microbiome-associated biomarkers.

In examples, microbiome biomarkers can include one or more of: a richness diversity index, a Shannon diversity index, a phylogenetic entropy index, beta diversity indices (e.g. weighted and unweighted UniFrac distances, bray-curtis dissimilarity index etc.), *Lactobacillus* relative abundance, *Bifidobacterium* relative abundance, *Akkermansia* relative abundance, *Christensenella* relative abundance, *Faecalibacterium* relative abundance, acetate metabolism relative abundance, propionate metabolism relative abundance, butyrate metabolism relative abundance, polyamine metabolism relative abundance, serotonin synthesis relative abundance, GABA synthesis relative abundance, vitamin B1 (thiamine) synthesis relative abundance, vitamin B2 (riboflavin) synthesis relative abundance, vitamin B3 (niacin) synthesis relative abundance, vitamin B5 (pantothenate) synthesis relative abundance, vitamin B6 (pyridoxine) synthesis relative abundance, vitamin B7 (biotin) synthesis relative abundance, vitamin B9 (folate) synthesis relative abundance, vitamin B12 (cobalamin) synthesis relative abundance, vitamin C synthesis relative abundance, vitamin K synthesis relative abundance, lactose degradation relative abundance, gluten degradation relative abundance, caffeine metabolism relative abundance, alcohol metabolism relative abundance, trimethylamine N-oxide synthesis relative abundance, histamine synthesis relative abundance, and/or other microbiome biomarkers. Additionally or alternatively, the microbiome markers can include abundance (e.g., absolute, relative or differential) of keystone microbial species and functional pathways as identified by machine learning algorithms, associated with health and disease conditions (e.g. gut health, mental health, metabolic disorders etc.).

In specific examples, microbiome biomarkers can be associated with one or more of: *Ruminococcus torques* group, *Candidatus soleaferrea, Intestinimonas*, Unclassified genus GCA-900066575 of Lachnospiraceae family, *Eubacterium hallii* group, *Alistipes, Megasphaera, Desulfovibrio*, Unclassified genus Clostridia UCG-014, *Escherichia-shigella, Fusicatenibacter, Tyzzerella, Megasphaera, Moryella, Parabacteroides, Eubacterium coprostanoligenes* group, Unclassified genus Anaerovoracaceae Family XIII AD3011 group, *Lachnospira, Terrisporobacter, intestinimonas, Prevotella*, Unclassified genus UCG-099 of Butyricicococcaceae family, *Lactobacillus, Phascolarctobacterium*, and/or other taxonomic groups. Additional examples of microbiome taxa and/or functions are described in more detail in Sections 2.5.1 and 2.5.2 below.

In examples described below, trained models can return output combinations of microbiome-associated biomarkers having high predictive power in relation to one or more of: Cardiovascular/cardiometabolic conditions, obesity and weight-related conditions, FGID, IBS, Constipation, Diarrhea, comorbidities, and/or other conditions.

In variations, lifestyle biomarkers can include or be derived from one or more of: energy levels (e.g., morning energy levels, midday energy levels, evening energy levels, etc.), dietary behavior (e.g., consumption behavior), sleep behavior, stress levels, stress-associated events, cravings, exercise behavior, perceived progress toward a health-associated goal, actual progress toward a health-associated goal (e.g., weight loss progress, fitness progress, exercise regimen progress, etc.), changes in appetite, state of symptoms, and/or other lifestyle biomarkers.

In variations, therapeutics biomarkers can include or be derived from one or more of: medication usage (e.g., current usage, changes in usage over time), supplement usage (e.g., current usage, changes in usage over time), psycho-social intervention biomarkers (e.g., cognitive behavioral therapy (CBT) characterizations), and/or other biomarkers associated with existing therapeutics that the subject interacts with.

Model outputs can be processed in relation to input subject condition statuses, subject body mass index (BMI), subject gender, combinatorial inputs (e.g., condition status: BMI; condition status: gender), residuals, and/or other inputs described above.

2.2.4 Model Architecture

In embodiments, models for processing inputs described and returning outputs described, in order to achieve the performance characteristics described, can include statistical models structured to receive input data, and to return indications of subsets of features having high predictive power with respect to subject characterization (e.g., in terms of estimates, in terms of standard error, in terms of t-values, in terms of P-values, etc.).

In variations, model architecture can include regression models (e.g., linear regression models, logistic regression models, polynomial regression models), correlation models (e.g., Pearson correlation, Kendall rank correlation, Spearman correlation, Point-Biserial correlation, etc.), and/or other model architecture. In specific examples, regression models can include quantile regression architecture (e.g., for data with high levels of outliers, high skewness and heteroscedasticity), ridge regression architecture, lasso regression architecture, elastic net regression architecture, principal components regression, partial least squares regression architecture, support vector regression, ordinal regression architecture, Poisson regression architecture, negative binomial regression architecture, quasi Poisson regression architecture, Cox regression architecture, Tobit regression architecture, and/or other regression architecture, with or without regularization and/or implementation of loss functions.

Prior to fitting models, input data can be conditioned or otherwise pre-processed, such that conditioned data elements (e.g., genomic reads associated with loci of interest, microbiome reads, functional data, behavioral data, sensor data, other contextual data described above, etc.) are suitable for further processing. Conditioning, as described above, can include filtering of data (e.g., removing sequencing reads or sensor data outputs that have confidence values below a threshold, removing sequencing reads having missing values greater than a threshold level, etc.).

In variations, the method 100 can include transforming output data into digital objects, such as visualizations, in order to facilitate generation of characterizations, interventions for condition prevention, interventions for condition treatment, and/or other actions (e.g., computer-generated and machine-implementable instructions) for improving or maintaining subject health. In specific examples, digital objects and visualizations can be generated upon transforming input data, using various statistical packages (e.g., R stats, ggplot2, pscl, car, pROC, Metrics, caret, glmnet, tidyverse, lubridate, imputeTS, and ggpubr packages) in sequence and/or in parallel.

Specific implementations of model architecture for health condition areas are described in Section 2.5 below, and embodiments, variations, and examples of model training are described in Section 2.6 below.

2.3 Methods—Exemplary Conditions Targeted

In variations, biomarker signatures and baseline states, as well as personalized therapeutics developed using the invention(s) described, can target one or more health conditions or indications.

In examples, conditions targeted can include one or more of: cardiovascular/cardiometabolic disorders (e.g., hypertension, high LDL cholesterol, low HDL cholesterol, high triglycerides, etc.); insulin-related health conditions (e.g., type 2 diabetes, other forms of diabetes, prediabetes, PCOS, etc.); obesity and other weight-associated conditions; acute pain, chronic pain associated with other conditions (e.g., joint pain including persistent joint aches and joint swellings, osteoarthritis, gout, rheumatoid arthritis, etc.); headaches (e.g., migraines, etc.); digestive health issues (e.g., functional gastrointestinal disorders (FGIDs), irritable bowel syndrome (IBS), inflammatory bowel disease (IBD), acid reflux, gastroesophageal reflux disease (GERD), functional constipation, functional diarrhea, bloating, etc.); neurological health conditions; integumentary/skin health conditions (e.g., rashes/dryness, itching, hair loss, acne, rosacea, eczema, atopic dermatitis, psoriasis, alopecia, etc.); mental health conditions (e.g., anxiety, depression, autism, bipolar disorder, memory loss, brain fog, cognitive functions etc.); sleep issues (e.g., sleep apnea, disturbed sleep, fatigue, etc.); renal disorders (e.g., kidney stones, renal failure, etc.); non-alcoholic fatty liver disease (NAFLD); hormonal health conditions (e.g., hyperthyroidism, hypothyroidism, thyroiditis, menopause, altered testosterone levels, etc.); and/or other conditions.

2.4 Methods—Personalized Intervention Plan

Block S150 recites: generating a personalized intervention plan for the subject upon processing the baseline state, the set of diagnostic signatures, and the set of therapeutic signatures with a multi-omic model, which functions to transform signatures into a customized combination of therapeutic approaches tailored to improve or maintain a health state of the subject.

The multi-omic model is preferably constructed to process signatures and/or baseline states generated from Block S140, and to return the personalized intervention plan that is tailored to the subject. In variations, the multi-omic model can return a set of SNP features and a set of microbiome features for the subjects, and generate their personalized intervention plans from the set of SNP features and the set of microbiome features.

In variations, the personalized intervention plan can have subportions (e.g., modules, phases). In variations, the subportions can include portions including one or more of: personalized medication regimens, personalized supplement regimens, personalized diets, personalized exercise regimens, personalized sleep regimens, personalized lifestyle recommendations, personalized behavioral therapeutic approaches (e.g., cognitive behavioral therapeutic approaches, etc.), medical procedures, preventative healthcare therapeutic approaches, and/or other suitable aspects. Furthermore, the personalized intervention plan can be characterized with a duration, such that the subject can complete the program and achieve one or more health goals. As such, generating the personalized intervention plan can include returning recommendations (e.g., dietary recommendations, sleep regimen recommendations, exercise regimen recommendations, etc.) and coaching components delivered in person and digitally, configured to adjust taxonomic abundances and microbiome function represented by microorganism taxa of the set of microbiome features, based upon risk alleles of the set of SNP features of the subject. However, the personalized intervention plan can be otherwise configured.

In variations, Block S150 can include generation of instructions, that can be executed by systems having a computing element (e.g., as described in more detail below). For instance, one or more components of the personalized intervention plan can be delivered digitally through a mobile device application, by way of an application-interface between coaching entities and the subjects being treated.

In one example, the personalized intervention plan can have a set duration (e.g., 36 weeks, 24 weeks, 12 weeks, another suitable number of weeks, etc.), and can be configured for delivery using one or more interfaces (e.g., web interface, mobile device interface, wearable computing device interface, telephonic interface, in-person interface, interface with one or more robotic devices, etc.) with the subject.

The example personalized intervention plan has a first phase, a second phase, and a third phase configured to promote behavior change in the subject, provide therapeutic interventions, and achieve desired outcomes with respect to diagnoses and characterizations generated (e.g., based on diagnostic signatures processed by the model, based on therapeutic signatures processed by the model, etc.) in prior blocks of the method 100.

In the example, the first phase has a duration (e.g., 4 weeks, another suitable number of weeks) configured to guide the subject in focusing on baselining health and habits, with functionality for tracking lifestyle through a mobile device application. In the example, the second phase has a duration (e.g., 12 weeks, another suitable number of weeks) focused on personalizing therapeutic approaches for producing transformations in behavior for the subject. In the example, the third phase has a duration (e.g., 8 weeks, another suitable number of weeks) focused on personalizing therapeutic approaches for stabilizing the subject's life, with respect to maintenance of desired states (e.g., building and maintaining healthy habits, preventing relapse, maintaining remission, etc.).

In more detail with respect to the personalized intervention plan, the platform can provide the kit (e.g., genetic and microbiome sampling kit, connected devices, biometric devices, instructions, etc.), and interaction with the kit by the subject facilitates establishment of a physiological baseline that can serve as a reference point for progress, with respect to the personalized intervention plan. In the example, the kit can be mailed (e.g., as facilitated by the platform), to the subject's home. The kit also provides instructions for downloading an application with an interface to the platform, as well as functionality for receiving inputs associated with the lifestyle dataset described above. In one specific example, the subject is prompted to download the mobile application, complete a lifestyle intake form, and schedule a counseling session as part of a personalized therapeutic approach.

Subsequently, with respect to the personalized intervention plan, the platform guides and supports the subject using counseling entities (e.g., specialized counselors, artificial intelligence counseling entities, etc.) through a 24 week chronic lifestyle illness transformation journey with regular sessions (e.g., weekly and bi-weekly sessions) that can be scheduled and/or ad hoc. In more detail, a counseling session of the specific example can be a 15-20 telephonic behavioral counseling session, but variations of the example can have another duration and/or be provided in another format. The personalized intervention plan provides personalized therapeutic pathways configured to reconfigure diet, lifestyle and physical activity of the subject to achieve a goal (e.g., 5-10% weight loss goal, other goal), which is shown to reduce chronic inflammatory conditions. With respect to the personalized intervention plan generated in Block S150, personalized and actionable insights are returned by the model and delivered to the subject (e.g., through entities, through application interfaces, through other interfaces with the platform, etc.) as they complete phases of the personalized intervention plan (e.g., complete tasks, interact with modules, interact with tools for monitoring diet (e.g., through upload of photo documentation of their meals/diet/consumption), monitor their lifestyle vitals: morning energy, sleep, stress, cravings, exercise, and weight loss progress through the mobile application and wireless scale, etc.). In examples, the subject can engage with the personalized intervention plan at any time or place via their mobile device application and/or web application, which allows for flexible participation. Additionally or alternatively, the personalized intervention plan can provide time-sensitive tasks and/or prompt interaction in a timely manner, with respect to more acute states of the subject (e.g., triggering events, symptom flare ups, etc.).

In variations, the personalized intervention plan can further provide one or more of the following: inflammatory nutrition and fitness insights; probiotic analysis and functional gut microbiome reports; food recommendations (e.g. meal plans to adjust abundances of various microorganisms); meal plans to decrease pathogenic or pathobiont microorganisms; meal plans to modulate specific microbial functions; etc.); prebiotic recommendations; gut biome monitoring to track immunity and gut microbiome-related disorders; other microbiome characteristics to track other statuses and conditions; and other information.

In examples, model outputs can be used to evolve a food guide of the personalized intervention plan, as the subject progresses through the phases of the program and updates when a new set of information about the subject is available. In an example, the food guide contains at any given time: a food list, foods to eat, foods to exclude, foods to eat in moderation, sample meal plan, grocery list, pantry list, portion guidelines, how to structure an approved meal plan, any other information about the current stage of the subject journey, ancillary food guides for major food chains and generic recommendations common to all phases (e.g., approved snacks, tips for craving, tips for takeout food). In the example, in the first phase the food guide can be personalized based on preferences, exclusions and comorbidities informed by subjects in intake forms. In the second phase, the guide can be further personalized incorporating information about deficiencies, intolerances and high risks derived from genetic traits in the DNA nutrition report and DNA fitness report, as well as microbial diversity, probiotic abundance and microbial metabolic pathway abundance from the gut microbiome report. In the third phase, the guide can be further personalized incorporating information about additional deficiencies, intolerances and high risks derived from additional genetic traits in the DNA reports (e.g., allergy report, skin health report, gut health report, mental health report, sexual health report, sleep report, cardiometabolic report, hormonal health report, and musculoskeletal health report), as well as comparative features in two or more gut microbiome reports, including comparative diversity index, comparative probiotic abundance, and comparative microbial metabolic pathways.

In another example, a specific meal plan of a personalized intervention plan to adjust abundances of a specific microorganism (or profile of microorganisms). For instance, meal plans can be generated based on model outputs, and *Akkermansia muciniphila* can be recommended to subjects that have low *Akkermansia muciniphila* abundance in their gut microbiome samples when compared to a healthy reference cohort, after a low fermentable oligosaccharides, disaccharides, monosaccharides and polyols (FODMAP) diet, after completing an antibiotic course, or when hitting a weight plateau. The meal plan of the specific example can incorporate a grocery list highlighting protein, fruit and vegetables; a pantry lust including broth, dairy, fermented dairy, nuts & seeds, prebiotic, salad dressings, seasonings, spices; breakfast recipes, lunch recipes, and dinner recipes; a how to plan your own *Akkermansia* meal plan section; and a food list including protein, fats, nuts, seeds, group 1 vegetables, fermented dairy, group 2 vegetables, fermented vegetables, other fermented products, group 3 vegetables, prebiotics, beverages, herbs & spices, group 1 fruits, and group 2 fruits.

In an additional example, the personalized intervention plan provides prebiotic recommendations specific to tackle deficiencies or health conditions. A first blend containing chicory inulin powder and partially hydrolyzed guar gum is recommended to subjects suffering from a group of health conditions (e.g., constipation, and those seeking to lose weight with no additional gut health comorbidities). A second blend containing chicory inulin powder and 100% green bananas is recommended to subjects suffering from a different group of health conditions (e.g., diarrhea). Recommended dosage is from 2.5 g to 50 g per day for intervals of up to 60 days.

In variations, the application environment (e.g., mobile application environment, web application environment, etc.) can support one or more of the following: a dietary consumption log (e.g., food log, drink log, etc.) that can receive inputs from the subject and/or automatically track consumption of the subject (e.g., in coordination with applications supported by Apple Health™, Google Health™, etc.); a prebiotic consumption log; a Bristol stool scale log; personalized meal and fitness plans generated from the personalized intervention plan; personalized guidance for anxiety, stress and sleep management generated from the personalized intervention plan. Additionally or alternatively, the application environment can include interfaces for connections with (e.g., using Bluetooth™, using another protocol) connected smart devices (e.g., as described above, for automatic weight, cardiovascular parameter tracking, blood analyte parameter tracking, motion tracking, etc.).

In variations, the application environment can further support telehealth interactions between the subject and a counseling/healthcare-providing entity. For instance, the application environment can provide one or more of: communication interfaces that connect the subject with a physician and/or facilitate delivery of care to the subject (e.g., through automated processing of insurance claims, through generation of appointments, through enabling consultations with a medical doctor, etc.); communication interfaces that provide constant or near constant access (e.g., 24 hour, 7 days a week access, etc.) to trained coaches, nutritionists, counselors, therapists, etc.; communication interfaces that enable telehealth group coaching; exercise regimen components (e.g., group fitness content, exercise guidance content, such as yoga content, etc.); stress management material (e.g., provided to the subject in response to detected stress states and/or triggering events, provided to the subject such that the subject can access the content in a convenient manner, etc.); interfaces to a private (e.g., invite-only) social network or community; tasks (e.g., healthy habits challenges); interfaces for reward provision (e.g., community celebration events, incentives, other perks, etc.); and other suitable interfaces.

The application environment can, however, support other suitable functionality associated with the personalized intervention plan.

2.5 Methods—Execution of Personalized Intervention Plan and Exemplary Results

Block S160 recites: executing the personalized intervention plan for the subject, where executing the personalized intervention plan can involve executing components of the intervention plan through interfaces described above and/or in relation to the system described below. As such, execution can involve mobile device application interfaces, web application interfaces, interfaces with an entity (e.g., human care-providing entity, digital care-providing entity, etc.), and/or other suitable interfaces.

Execution of the personalized intervention plan produces improved outcomes for subjects participating in their respective personalized intervention plans, examples of which include: improved engagement (e.g., enrollment of 93% of participants; consistent engagement by a significant percentage of participants after 60 days); improved outcomes (e.g., significant improved weight loss, significant reductions in A1C levels associated with diabetes, significant reductions in cardiovascular symptoms, significant reductions in digestive disorder conditions and comorbidities, such as irritable bowel syndrome (IBS) symptoms, acid reflux symptoms, headache symptoms, anxiety symptoms, musculoskeletal pain symptoms, skin condition symptoms, sleep disruption symptoms, etc.); reduction in medication use/necessity; reduction in healthcare costs; and other suitable benefits.

Additionally or alternatively, improved outcomes can be measured at an individual level or at an aggregate number of subjects within a cohort and can include: percent weight loss, weight loss over a period of time, average number of months maintaining weight loss after completing the program, average reduction in HbA1C levels, average reduction of fasting blood glucose, decreased bloating symptomatology, decreased constipation symptomatology, decreased cramping symptomatology, decreased diarrhea symptomatology, decreased gassiness symptomatology, decreased heartburn and acid reflux symptomatology, decreased IBS symptomatology, overall digestive issues symptoms improvement, decreased anxiety symptomatology, decreased brain fog or memory challenges symptomatology, decreased depression symptomatology, decreased disturbed sleep symptomatology, decreased headaches or migraines symptomatology, decreased insomnia symptomatology, decreased sleep apnea symptomatology, overall mental health issues symptoms improvement, overall sleep-related conditions symptoms improvement, decreased chronic pain symptomatology, among other improved outcomes.

Executing the personalized intervention plan in Block S160 can include providing results presented in a genetics section of one or more reports generated from model outputs (e.g., within an application environment), which were determined by the number of markers and risk genotypes present in the genomic raw data. Reports can then be transmitted to the entities involved (e.g., subjects, caretakers, insurance companies, etc.) by mobile application and/or web application architecture. Executing the personalized intervention plan in Block S160 can further implement genetic risk profiles to guide the course of subjects' precision care, as well as analyzing gut microbiome profiles (collected from regular stool swab sampling) to guide the course of care. Based on analysis of these genetic and gut microbiome risk profiles, an analysis (e.g., a Total Wellness Report) can thus be provided in Block S160, and in an exemplary program implementation, the results were systematically reviewed with the participants 1:1 by the health coach over a 4-month period at regular, pre-determined, weekly and bi-weekly intervals.

Executing the personalized intervention plan in Block S160 can further include providing a personalized care program that implements body metrics, gut microbiome and genetic profiles, and personalized health-coaching to manage weight loss. In accordance with the personalized care program, participants can be provided with digital tools for tracking 10 key lifestyle and wellness markers (i.e., weight, sleep, hunger, cravings, stress, meditation, superfoods, energy, foods to avoid, and exercise), documenting the food they consume (e.g., through a photo journal, through a text journal, through a wearable device, etc.), and are assigned a health coach who works personally with the participant through guided sessions as scheduled by the subjects to interpret the personalized wellness reports generated from participants' app usage and from sampling participants' DNA and gut microbiota. In accordance with the personalized care program, the reports also provide a breakdown of obesity risk based on individuals' genetic and gut microbiome profiles. The program can be geared toward participant goals (e.g., losing at least 5% of their baseline body weight by Day 90 of the program). To achieve this goal, example implementations of the program were structured to provide automated and manual tools for motivating participants to make incremental lifestyle changes focused around reducing sugar consumption, timing meals to optimize insulin sensitivity, reducing systemic inflammation by identifying possibly inflammatory and anti-inflammatory nutrients via genetic testing, establishing a base level of physical activity and doing so in a manner that reduces inflammation, optimizing gut health based on microbiome testing, and establishing these behavioral modifications as habits, supported by health coaching and the applications so that the changes are sustainable long-term.

In specific examples, implementation of the personalized intervention plan, based upon outputs of models described, achieved groundbreaking performance with respect to individual or simultaneous reduction in symptom severity associated with one or more of: hemoglobin A1C levels, digestive disorder symptoms, comorbidities (e.g., associated with weight gain, insomnia/sleep disorders, depression/anxiety symptoms, chronic inflammatory pain, chronic acne/eczema other skin condition symptoms, other symptoms, etc.).

Variations of the methods described can produce over 5% reduction in cardiovascular symptom severity, over 6% reduction in cardiovascular symptom severity, over 7% reduction in cardiovascular symptom severity, over 8% reduction in cardiovascular symptom severity, over 9% reduction in cardiovascular symptom severity, over 10% reduction in cardiovascular symptom severity, over 15% reduction in cardiovascular symptom severity, or greater values of reduction in cardiovascular symptom severity in comparison to baseline states for a subject on the personalized intervention plan.

Variations of the methods described can produce over 0.5% reduction in hemoglobin A1C values, over 1% reduction in hemoglobin A1C values, over 2% reduction in hemoglobin A1C values, 3% reduction in hemoglobin A1C values, over 4% reduction in hemoglobin A1C values, over 5% reduction in hemoglobin A1C values, or greater values of reduction in hemoglobin A1C values in comparison to baseline states for a subject on the personalized intervention plan.

Variations of the methods described can produce over 20% reduction in digestive disorder symptoms, over 30% reduction in digestive disorder symptoms, over 40% reduction in digestive disorder symptoms, over 50% reduction in digestive disorder symptoms, over 60% reduction in digestive disorder symptoms, over 70% reduction in digestive disorder symptoms, over 80% reduction in digestive disorder symptoms, over 90% reduction in digestive disorder symptoms, over 95% reduction in digestive disorder symptoms, over 99% reduction in digestive disorder symptoms, or greater values of reduction in digestive disorder symptoms in comparison to baseline states for a subject on the personalized intervention plan.

Variations of the methods described can produce over 50% reduction in insomnia/sleep disorder symptoms (e.g., apnea, disturbed sleep), over 60% reduction in insomnia/sleep disorder symptoms, over 70% reduction in insomnia/sleep disorder symptoms, over 80% reduction in insomnia/sleep disorder symptoms, over 90% reduction in insomnia/sleep disorder symptoms, over 95% reduction in insomnia/sleep disorder symptoms, over 99% reduction in insomnia/sleep disorder symptoms, or greater values of reduction in insomnia/sleep disorder symptoms in comparison to baseline states for a subject on the personalized intervention plan.

Variations of the methods described can produce over 30% reduction in depression/anxiety symptoms, over 40% reduction in depression/anxiety symptoms, over 50% reduction in depression/anxiety symptoms, over 60% reduction in depression/anxiety symptoms, over 70% reduction in depression/anxiety symptoms, over 80% reduction in depression/anxiety symptoms, over 90% reduction in depression/anxiety symptoms, over 95% reduction in depression/anxiety symptoms, over 99% reduction in depression/anxiety symptoms, or greater values of reduction in depression/anxiety symptoms in comparison to baseline states for a subject on the personalized intervention plan.

Variations of the methods described can produce over 30% reduction in chronic inflammatory pain symptoms, over 40% reduction in chronic inflammatory pain symptoms, over 50% reduction in chronic inflammatory pain symptoms, over 60% reduction in chronic inflammatory pain symptoms, over 70% reduction in chronic inflammatory pain symptoms, over 80% reduction in chronic inflammatory pain symptoms, over 90% reduction in chronic inflammatory pain symptoms, over 95% reduction in chronic inflammatory pain symptoms, over 99% reduction in chronic inflammatory pain symptoms, or greater values of reduction in chronic inflammatory pain symptoms in comparison to baseline states for a subject on the personalized intervention plan.

Variations of the methods described can produce over 10% reduction in chronic acne/eczema symptoms, over 20% reduction in chronic acne/eczema symptoms, over 30% reduction in chronic acne/eczema symptoms, over 40% reduction in chronic acne/eczema symptoms, over 50% reduction in chronic acne/eczema symptoms, over 60% reduction in chronic acne/eczema symptoms, over 70% reduction in chronic acne/eczema symptoms, over 80% reduction in chronic acne/eczema symptoms, over 90% reduction in chronic acne/eczema symptoms, over 95% reduction in chronic acne/eczema symptoms, over 99% reduction in chronic acne/eczema symptoms, or greater values of reduction in chronic acne/eczema symptoms in comparison to baseline states for a subject on the personalized intervention plan.

Variations of the methods described can produce over 1% more weight loss, over 2% more weight loss, over 3% more weight loss, over 4% more weight loss, over 5% more weight loss, over 6% more weight loss, over 7% more weight loss, over 8% more weight loss, over 9% more weight loss, over 10% more weight loss, over 15% more weight loss, over 20% more weight loss, over 25% more weight loss, or greater weight loss in comparison to baseline states for a subject on the personalized intervention plan.

Variations of the methods described can produce over 40% reduction in brain fog/memory challenge symptoms, over 50% reduction in brain fog/memory challenge symptoms, over 60% reduction in brain fog/memory challenge symptoms, over 70% reduction in brain fog/memory challenge symptoms, over 80% reduction in brain fog/memory challenge symptoms, over 90% reduction in brain fog/memory challenge symptoms, over 95% reduction in brain fog/memory challenge symptoms, over 99% reduction in brain fog/memory challenge symptoms, or greater values of reduction in brain fog/memory challenge symptoms in comparison to baseline states for a subject on the personalized intervention plan.

Variations of the methods described can produce over 40% reduction in headache/migraine symptoms, over 50% reduction in headache/migraine symptoms, over 60% reduction in headache/migraine symptoms, over 70% reduction in headache/migraine symptoms, over 80% reduction in headache/migraine symptoms, over 90% reduction in headache/migraine symptoms, over 95% reduction in headache/migraine symptoms, over 99% reduction in headache/migraine symptoms, or greater values of reduction in headache/ migraine symptoms in comparison to baseline states for a subject on the personalized intervention plan.

Variations of the methods described can produce over 40% reduction in a set of cardiovascular symptoms, over 50% reduction in a set of cardiovascular symptoms, over 60% reduction in a set of cardiovascular symptoms, over 70% reduction in a set of cardiovascular symptoms, over 80% reduction in a set of cardiovascular symptoms, over 90% reduction in a set of cardiovascular symptoms, over 95% reduction in a set of cardiovascular symptoms, over 99% reduction in a set of cardiovascular symptoms, or greater values of reduction in a set of cardiovascular symptoms in comparison to baseline states for a subject on the personalized intervention plan.

In examples, cardiovascular symptoms can include one or more of: blood pressure, fasting blood sugar, glycemic response, high density lipids, and low density lipids.

In examples, the set of cardiovascular symptoms can include one or more of: pain level (e.g., chest pain level, extremity pain level, neck pain level, throat pain level, abdominal pain level, back pain level, etc.), chest tightness, chest pressure, angina, respiratory distress (e.g., shortness of breath, blood oxygenation, respiration rate, etc.), extremity numbness, extremity strength, vasculature narrowness, cardiovascular parameters (e.g., heart rate, heart rate variability, blood pressure, output, electrocardiogram signatures, stroke volume, cardiac index, etc.), cholesterol levels (e.g., HDL levels), blood glucose levels, and other cardiovascular symptoms. Cardiovascular symptoms can be associated with one or more of: coronary artery disease, hypertension, cardiac arrest, congestive heart failure, arrhythmias, peripheral artery disease, stroke, congenital heart disease, and/or other diseases or comorbidities.

In examples, a subject experienced reduction of blood pressure from 134/85 to 113/71 after 140 days in the program. In variations, the methods produced over 5% reduction, over 6% reduction, over 7% reduction, over 8% reduction, over 9% reduction, over 10% reduction, over 11% reduction, over 12% reduction, over 13% reduction, over 14% reduction, over 15% reduction, or greater reductions in systolic blood pressure over a period of time in the program. In variations, the methods produced over 5% reduction, over 6% reduction, over 7% reduction, over 8% reduction, over 9% reduction, over 10% reduction, over 11% reduction, over 12% reduction, over 13% reduction, over 14% reduction, over 15% reduction, over 16% reduction, or greater reductions in diastolic blood pressure over a period of time in the program.

In examples, a subject after 91 days in the program experienced reduction of blood glucose from 140 mg/dL to 120 mg/dL. In variations, the methods produced over 5% reduction, over 6% reduction, over 7% reduction, over 8% reduction, over 9% reduction, over 10% reduction, over 11% reduction, over 12% reduction, over 13% reduction, over 14% reduction, over 15% reduction, or greater reductions in blood glucose (e.g., measured in mg/dL) over a period of time in the program.

Variations of the methods described can produce one or more of the above results simultaneously, within a duration of 2 days, 3 days, 4 days, 5 days, 6 days, 7 days, 8 days, 9 days, 10 days, 20 days, 30 days, 40 days, 50 days, 60 days, 70 days, 80 days, 90 days, 100 days, any intermediate number of days, or greater than 100 days, with sustained maintenance of results.

Embodiments, variations, and examples of the methods described can simultaneously reduce severity of symptoms and/or increase weight loss with the personalized care program components generated based upon model outputs.

For instance, methods described can simultaneously reduce hemoglobin A1c levels, fasting blood sugar, glycemic response, high density lipids, and low density lipids by at least 1% in a subject.

Figure 2:
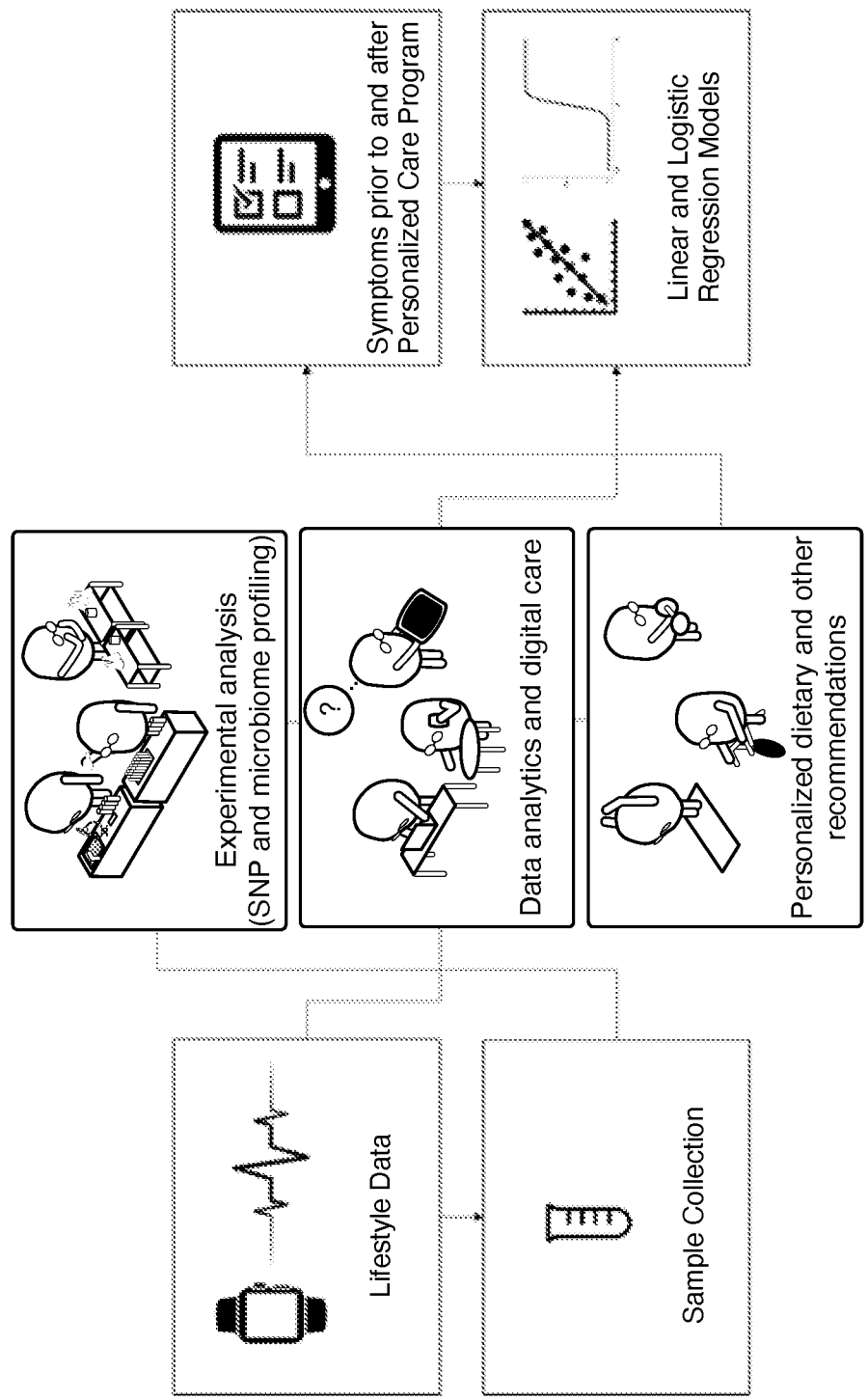
FIG. 2 depicts a graphical abstract of an embodiment of the invention(s), for providing personalized care for various health conditions.
Figure 3:
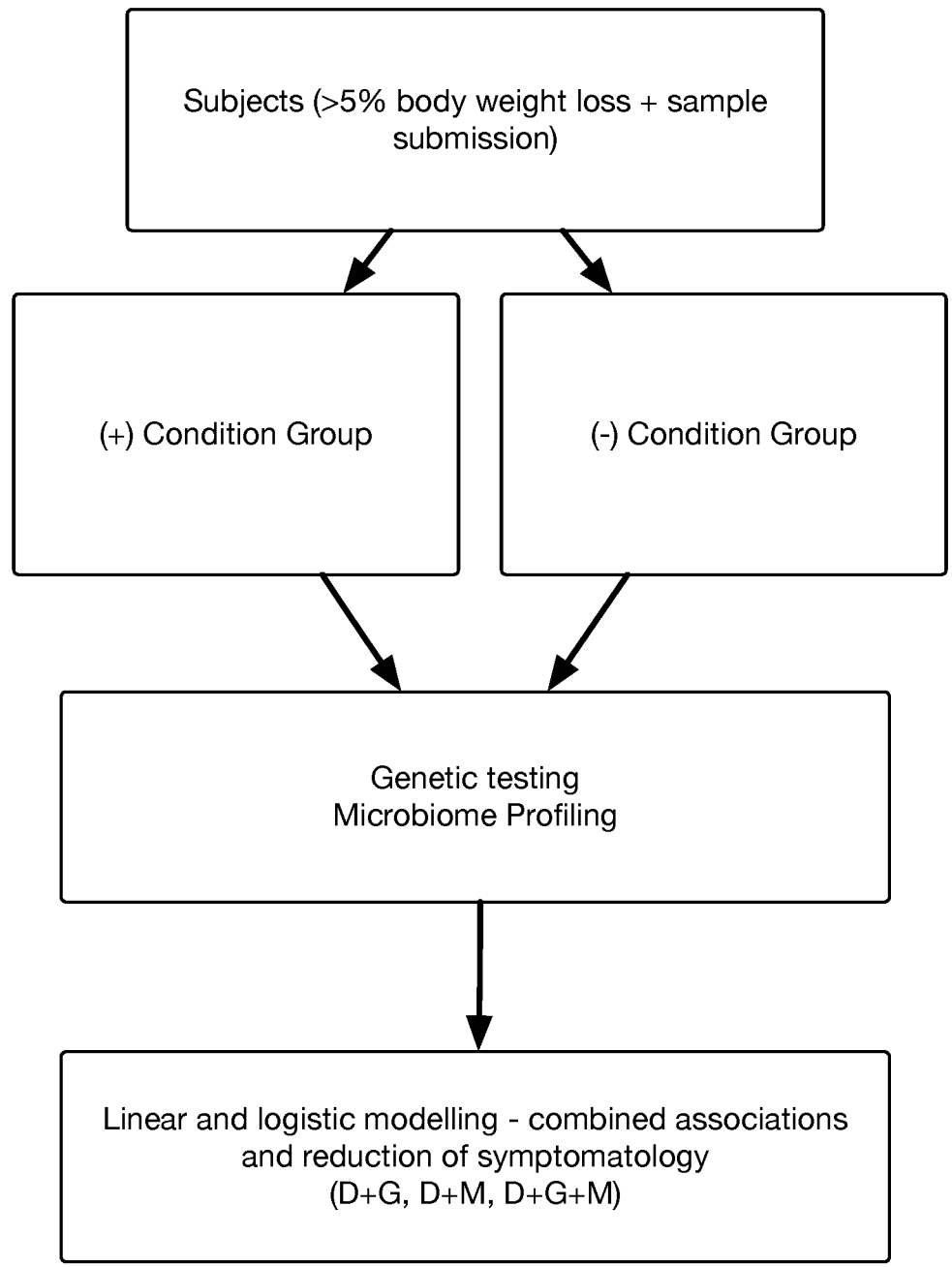
FIG. 3 depicts a workflow for processing input data from subjects, with model architecture, to providing personalized care for various health conditions.

Variations of the methods described can produce other reductions in symptom severity, for other symptoms as well. Exemplary methodologies, implementations of personalized care plans, and performance benefits over current care options are described as follows:

2.5.1 Method Exemplary Execution and Performance—Digestive and Gastrointestinal Conditions In an exemplary application of the platform for prevention and/or treatment of digestive and gastrointestinal conditions (as shown in FIG. 2 and FIG. 3), subjects across groups with and without gastrointestinal disorders (e.g., FGIDs, other gastrointestinal disorders) were analyzed and treated with personalized care. In examples, subjects self-collected saliva samples using buccal swabs (e.g., Mawi Technologies iSwab DNA collection kit, Model no. ISWAB-DNA-1200) and gut samples (e.g., fecal samples) using fecal swabs (e.g., Mawi Technologies iSWAB Microbiome collection kit, Model no. ISWAB-MBF-1200). Sample collection was completed by following standardized directions provided to all subjects in an instruction manual. The platform then performed saliva DNA extraction, purification, and genotyping (e.g., with automated sample processing apparatus executing machine-readable instructions, as described above and below in relation to system components) using Affymetrix's Direct to Consumer Array version 2.0 ("DTC") on the Affymetrix GeneTitan platform. The platform also performed sample processing of baseline (pre-intervention) fecal samples followed by 16S rRNA gene amplicon sequencing. The platform also performed DNA extraction (e.g., using Qiagen MagAttract Power Microbiome DNA Kit) by way of an automated liquid handling DNA extraction instrument. The platform also amplified and sequenced the V3-V4 region of 16S rRNA gene by way of an Illumina MiSeq platform using 2×300 bp paired-end sequencing. The platform demultiplexed sequence reads and generated amplicon sequence variants (ASVs) using DADA2 in QIIME2 (version 2020 August). In examples, the platform trimmed primers and low quality bases (Q<30) from the reads. Computing components with architecture for transforming input data performed taxonomic annotation using a Naive Bayes classifier against the 99% non redundant Silva 138 reference database. In examples, hits to mitochondria, chloroplast, eukaryota, and unassigned taxa at phylum level were excluded. As such, data generated from processed samples was prepared and processed by the platform according to the exemplary statistical model architecture aspects described as follows:

Statistical Model Architecture: Data from 177 subjects (with either or both genome SNP or gut microbiome data) over the course of their symptom improvement and weight loss journey in the personalized digital care program was analyzed by way of the trained model architecture described. Input data to the models included demographic data (e.g., gender, age, weight and BMI during gut microbiome sample collection and weight loss achieved during the program), genomic loci of interest (e.g., SNPs) and baseline gut microbiome data. In examples, the model architecture implemented Wilcoxon sum rank/signed rank test or Kendall correlation test, as appropriate, to assess: (a) the change in severity of either of the gastrointestinal symptoms (e.g., FGID symptoms) and also a summative severity change, and (b) the effect of variables on the change in severity. Significance results were adjusted for multiple comparisons using false discovery rate (FDR) correction method for the microbiome data.

Genome Loci/SNP-Related Statistical Model Architecture: 16 SNP predictors, associated with lactose intolerance, gluten sensitivity, milk and peanut allergies, caffeine metabolism, and inflammatory markers (TNF & IL10), were from curated panels used for personalized interventions for subjects. Each SNP value was encoded as the number of risk alleles (0, 1, or 2) for each subject. In specific examples, SNPs of the panel associated with caffeine metabolism can include one or more of: rs2472297 (risk allele C) and/or rs762551 (risk allele C) associated with gene CYP1A2; SNPs of the panel associated with gluten sensitivity can include one or more of: rs2187668 (risk allele T) associated with gene HLA-DQ 2.5, rs2395182 (risk allele T) associated with gene HLA-DQ 2.2 (M1), rs4639334 (risk allele A) associated with gene HLA-DQ7; rs4713586 (risk allele G) associated with gene HLA-DQ 2.2 (M3), rs7454108 (risk allele C) associated with gene HLA-DQ8, and/or rs7775228 (risk allele C) associated with gene HLA-DQ 2.2; SNPs of the panel associated with lactose intolerance can include one or more of: rs182549 (risk allele C) associated with gene MCM6 and/or rs4988235 (risk allele G) associated with gene MCM6; SNPs of the panel associated with dairy allergies can include one or more of: rs324015 (risk allele T) associated with gene STAT6; SNPs of the panel associated with peanut allergies can include one or more of: rs7192 (risk allele T) associated with gene HLA-DRA and/or rs9275596 (risk allele C) associated with gene MTCO3P1-AL662789.1; SNPs of the panel associated with inflammation can include one or more of: rs1800629 (risk allele A) associated with gene TNF, rs1800896 (risk allele T) associated with gene IL10, and/or rs3024496 (risk allele G) associated with gene IL10. As such, the multi-omic model can include a first subarchitecture for processing genomic input data associated with lactose intolerance, gluten sensitivity, milk and peanut allergies, caffeine metabolism, and inflammatory markers, wherein said first subarchitecture is structured to infer non-genotyped alleles by means of one or more methods to accomplish dimensionality reduction and statistical inferences methods for data imputations, detection and encoding values of a set of genotyped and non-genotyped risk alleles of the genomic profile for the subject.

First subarchitecture (or variants for different conditions) can additionally or alternatively include structures for inferring non-genotyped alleles by means at least one of dimensionality reduction and statistical inferences methods for data imputations, with detection and encoding values of a set of risk alleles of the genomic profile for the subject.

First subarchitecture (or variants for different conditions) can additionally or alternatively include structures for processing genomic input data associated with lactose intolerance, histamin intolerance, alcohol intolerance, gluten sensitivity, cockroach allergy, dust mites allergy, pets allergy, hay fever, pollen allergy, grass allergy, milk allergy and peanut allergies, caffeine metabolism, and inflammatory markers, said first subarchitecture structured to infer non-genotyped alleles by means of at least one of dimensionality reduction and statistical inferences methods for data imputations, with detection and encoding values of a set of risk alleles of the genomic profile for the subject.

Microbiome-related Statistical Model Architecture: The statistical model architecture processed bacterial genera abundances for 168 subjects for which baseline gut microbiome was collected, using Qiime2, qiime2R, and phyloseq. The following microbial features were filtered out from downstream analysis, according to the design of the model architecture: (a) ASVs not classified at the phylum level, (b) phyla that had <25 ASVs (*Elusimicrobiota, Nanoarchaeota, Bdellovibrionota*, WPS-2), (c) uncultured and Incertae *Sedis taxa*, (d) genera that had <30 reads in at least 15% of samples, and (e) genera for which >25% of samples had zero read count. In total 105 genera were retained in downstream analysis. Abundance of these bacterial genera were transformed to centered log-ratio (CLR) (e.g., using the zCompositions package) after first replacing zeros with pseudo counts based on a Bayesian-multiplicative replacement (e.g., from the zCompositions package). Permutational multivariate analysis of variance (PERMANOVA) was performed on the gut microbiome Aitchison distance matrix, using gender, BMI (closest to date of gut biome sampling) and FGID status as variables using the CLR transformed abundances. Additionally, the read counts after zero replacement were transformed using additive log ratio (ALR) to be utilized in downstream model statistics (see below). As such, the multi-omic model can include a second subarchitecture for processing microbiome-associated input data, said second subarchitecture structured to return bacterial taxonomic abundances of the baseline microbiome state, said second subarchitecture further structured to filter out ASVs not classified at the phylum level, phyla that had <25 ASVs, *Elusimicrobiota* data, *Nanoarchaeota* data, *Bdellovibrionota* data, Incertae *Sedis* data, and said second subarchitecture further structured to transform bacterial taxonomic abundances to centered log-ratio (CLR) values.

Second subarchitecture can additionally or alternatively include structures for returning microbial taxonomic abundances of the microbiome state, said second subarchitecture further structured to return microbial diversity indices of a whole microbial community or a subset of the whole microbial community, and functional data, and/or for transforming microbial taxonomic and functional abundances to compositionally transformed and arithmetically derived values.

Higher-Level Model Architecture: In a specific implementation of model architecture for generating personalized interventions for gastrointestinal disorders, model architecture included lasso regression architecture as a first stage for variable selection prior to fitting linear and logistic regression model, with input data characterizing loci reads (e.g., SNP reads) with >10% missing values removed, followed by imputing remaining missing loci/SNP reads to their most frequent value (i.e., mode). This resulted in the removal of rs4713586 gluten sensitivity SNP from both reduction in summative symptom severity and reduction in constipation symptom severity models. In order to avoid poor performance in regression models, variables with Pearson correlation to another variable of ≥80% were removed. This excluded two SNPs from all regression models that incorporated DNA: rs182549 of the lactose persistence haplotype was removed while the more highly cited correlated (Pearson correlation, r=0.99) haplotype SNP, rs4988235, was retained. Additionally, IL10 SNP rs3024496 was removed as being highly correlated (Pearson correlation, r=−0.95) with rs1800896, another IL10 SNP, which was preferentially retained as having a higher risk in the population.

Then, for regression models, the model architecture was structured to transform bacterial abundance data using an additive log-ratio (ALR) operation, which maintains subcompositional coherence, permitting genera to be removed in downstream analysis (e.g., removing insignificant predictors from a regression model). For this, the easy Coda package was employed to analyze all 105 microorganisms (e.g., microbial genera) utilizing variances, variances explained, and Procrustes correlations to select candidate references for ALR. An additional criterion employed by the model architecture was a prevalence criterion, as zero values are problematic with log-ratios. Based on these criteria, *Blautia* was the selected reference for the gastrointestinal condition model. In all cases of highly correlated microbe pairs, the unclassified microbe was removed, or if both were unclassified, then the microorganism with the larger mean absolute correlation in that dataset was removed. This resulted in removing up to 5 microorganisms (of 105 total microorganisms) from regression models incorporating microbial predictors. According to model architecture, gender and locis (e.g., SNPs) were scaled to a range between −1 and 1. According to model architecture, age and gender were two demographic variables used in all models, and age was used in models with no transformation, in order to test association of age and/or gender in the context of the moderation effect of genetic and microbiome variables.

After the above data preparation, lasso regression model architecture was employed for variable selection in the modeling of datasets that included the microbial predictors (e.g., 105 microorganism predictors of the microbiome dataset). Optimal lambda was chosen by a fivefold cross-validation grid search, setting standardize=TRUE so that variables would compete fairly in regularization. The lambda resulting in the minimum mean cross-validated error was selected, or if this resulted in a paucity of predictors, then a plateau lambda in error vs. lambda plot having a sufficient number of predictors was selected. Mean squared error was employed in linear lasso regression, while the mean absolute error was used in logistic regression models. Predictors with non-zero coefficients were retained by the model architecture for subsequent best-fit regression to describe the differences of the subjects (e.g., in symptoms, in changes in symptoms, in changes in symptom severity, etc.) over the course of treatment.

To generate descriptive models, the exemplary model architecture implemented a step function operation (e.g., using the Akaike information criterion (AIC)) to obtain a high-quality fit. If any insignificant variables remained, the model was structured to remove insignificant variables one-by-one, beginning with the least significant, until only significant variables remained, resulting in a final interpretable model for each investigation and set of predictors.

The descriptive modeling of condition vs. non-condition (e.g., FGID vs. non-FGID) was performed using a logistic regression model for demographic and genomic data (e.g., D+G model), producing coefficients to describe the impact of each predictor on condition of interest (e.g., FGID) in a cohort of subjects. A second logistic model was fit with demographic plus baseline gut microbiome genera remaining after pre-processing (e.g., D+M model). A third logistic model employed lasso for variable selection from demographic variables, genomic SNPs, and baseline genera (D+G+M model).

The exemplary model architecture was constructed such that for subjects who were pre-characterized as having FGID conditions (e.g., through self reports, through pre-diagnoses, etc.), change in symptom severity was analyzed with respect to demographic, genome SNPs, and baseline gut microbiome data. The model architecture was used to process data from 104 subjects, who rated the severity of their FGID symptoms on a scale of 1-5. A linear regression model was fit to describe the change in summative symptom severity as a function of demographic and genomic variables (using the D+G model). As above, this model was compared with two additional models: demographic plus microbial predictors (the D+M model) and demographic, genomic, plus microbial predictors (the D+G+M model). Lasso regression was employed as above for variable selection, followed by the use of the step function. Additionally, changes in IBS, diarrhea and constipation symptom severity were modeled for those subsets of participants who reported them, using lasso with threefold cross-validation and linear regression as above with D+G, D+M, and D+G+M predictors.

Results: In total, subjects (including different genders, ages, and body mass indices) were successful at losing 5% or more body weight, and had genetic and/or gut microbiome data changes assessed according to the described models in symptomatology of their symptoms (as shown in FIG. 3). The model architecture was implemented to generate comparisons between baseline characteristics of those who reported gastrointestinal condition symptoms and those who did not. The model returned outputs indicating a significant difference in gender ($\chi^2$ test, p=0.004*) and initial BMI (Wilcoxon sum rank test, p=0.009*), between those who reported gastrointestinal condition symptoms and those who did not, but no significant difference was found between different age groups (Wilcoxon sum rank test, p=0.60). Subsequently, the model architecture also returned outputs indicating the effects of gender, BMI and FGID status on the beta diversity of baseline gut microbiome of subjects. PERMANOVA analyses demonstrated that gender had a significant effect on the beta diversity ($R^2$=0.012, p=0.030*), whereas BMI ($R^2$=0.007, p=0.279) and FGID status ($R^2$=0.005, p=0.532) did not.

FGID: For the exemplary group of subjects being analyzed and undergoing care, the model outputs indicated that gut microbiome taxa are a stronger predictor of FGID symptoms than the genomic SNPs analyzed in this study: SNP values were not significantly different (by Welch's two-sample t-tests) between respondents with FGID and those without. Logistic regression modeled the associations of demographic, genome SNP and baseline gut microbiome variables with FGID status in this cohort (Tables 1, 2 and 3), fitting separate average effect size for each predictor while controlling for all other model variables. The D+G model described females in this cohort as 3.26 times more likely than males to suffer FGID, while controlling for the genomic predictors in the model (Table 2), and each risk allele of the rs2187668 gene was associated with 2.93 times greater likelihood of being an FGID sufferer. Similarly, risk alleles for rs2472297 and rs9275596 were associated with lowered likelihood of FGID—conferring 0.45 and 0.56 times likelihood of being an IBD sufferer.

TABLE 1

FGID vs Non-FGID Logistic Model:
Demographics + Genomics (D + G)

| Variable | OR | 2.5% C.I. | 97.5% C.I. |
| --- | --- | --- | --- |
| Gender | 3.255 | 1.421 | 7.856 |
| Caffeine Metabolism (rs2472297), Risk Allele C | 0.447 | 0.211 | 0.888 |
| Gluten Sensitivity (rs2187668), Risk Allele T | 2.926 | 1.140 | 8.269 |
| Peanut Allergy (rs9275596), Risk Allele C | 0.556 | 0.323 | 0.935 |

McFadden pseudo $R^2$: 0.089

A second logistic model implemented according to methods described extracted associations of D+M together on likelihood of a subject having a FGID (Table 2). The 9 taxa identified by lasso regression were used as predictors for a logistic regression model to describe the classification of 168 subjects into their corresponding FGID status, using the genus *Blautia* as the reference denominator for ALR. In this model, the effect of female gender while controlling for microbial predictors was an average 2.33 times likelihood of FGID as compared with male gender. Genera *Ruminococcus torques* group, *Akkermansia*, unclassified genus CAG-56 of Lachnospiraceae family, *Haemophilus*, and *Terrisporobacter* were all associated with increased FGID. *Holdemanella*, unclassified genus UCG-010 of Oscillospirales order, *Anaerostipes*, and *Fusicatenibacter* were all associated with decreased (protective of) FGID status.

TABLE 2

FGID vs Non-FGID Logistic Model:
Demographics + Microbiome (D + M)

| Variable | OR | 2.5% C.I. | 97.5% C.I. |
|---|---|---|---|
| Gender | 2.334 | 1.213 | 4.686 |
| *Ruminococcus torques* group | 1.193 | 1.039 | 1.391 |
| *Akkermansia* | 1.076 | 1.011 | 1.151 |
| *Holdemanella* | 0.932 | 0.878 | 0.986 |
| Unclassified genus CAG-56 of Lachnospiraceae family | 1.095 | 1.024 | 1.175 |
| Unclassified genus UCG-010 of Oscillospirales order | 0.904 | 0.839 | 0.970 |
| *Anaerostipes* | 0.806 | 0.680 | 0.938 |
| *Haemophilus* | 1.115 | 1.034 | 1.210 |
| *Fusicatenibacter* | 0.894 | 0.803 | 0.985 |
| *Terrisporobacter* | 1.076 | 1.008 | 1.153 |

McFadden pseudo $R^2$: 0.220

A third logistic model implemented according to methods described generated associations of D+G+M variables together on likelihood of a subject having FGID status (Table 3), no SNPs had significant association with FGID risk. Variables in Tables 2 and 3 are identical, with just slight variations in odd ratios (ORs). Pseudo $R^2$ values from the D+M model (0.220) and the D+G+M model (0.227), were very similar, and improved from that of the D+G model (0.089).

TABLE 3

FGID vs Non-FGID Logistic Model: Demographics +
Genomics + Microbiome (D + G + M)

| Variable | OR | 2.5% C.I. | 97.5% C.I. |
|---|---|---|---|
| Gender | 2.256 | 1.151 | 4.638 |
| *Ruminococcus torques* group | 1.186 | 1.030 | 1.388 |
| *Akkermansia* | 1.080 | 1.013 | 1.156 |
| *Holdemanella* | 0.928 | 0.871 | 0.985 |
| Unclassified genus CAG-56 of Lachnospiraceae family | 1.100 | 1.028 | 1.184 |
| Unclassified genus UCG-010 of Oscillospirales order | 0.912 | 0.845 | 0.978 |
| *Anaerostipes* | 0.797 | 0.671 | 0.929 |
| *Haemophilus* | 1.098 | 1.017 | 1.193 |
| *Fusicatenibacter* | 0.892 | 0.801 | 0.983 |
| *Terrisporobacter* | 1.074 | 1.003 | 1.153 |

McFadden pseudo $R^2$: 0.227

Figure 4:
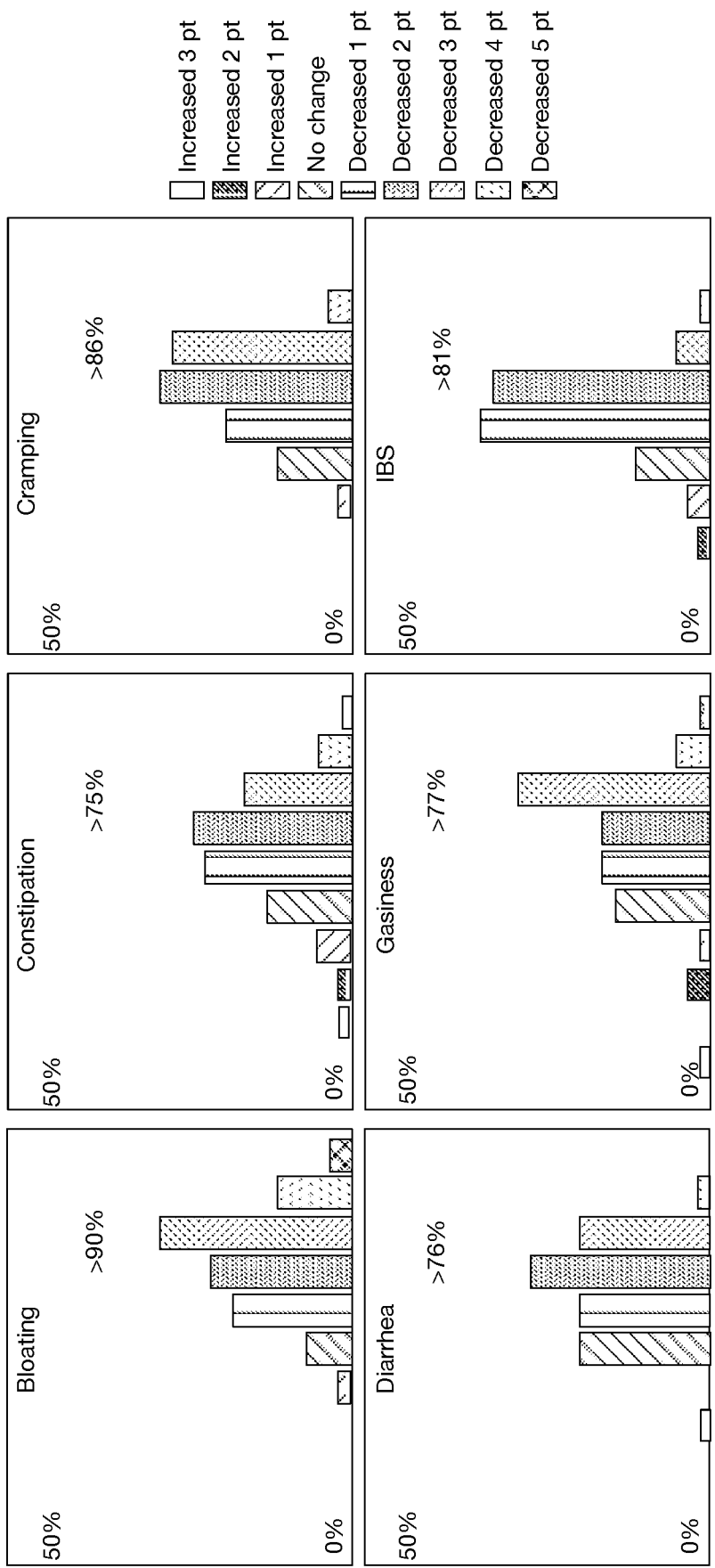
FIG. 4 depicts exemplary results of the methods and systems described, for subjects with FGID symptoms and comorbid conditions.

Upon provision of a personalized care plan/course of treatment by the platform, subjects reported a reduction in severity of gastrointestinal condition-related symptoms: The proportion of subjects who experienced at least one point improvement in symptom severity ranged from 75.32% for diarrhea to 90.63% for bloating (as shown in FIG. 4). Improvement in summative severity across the 6 symptom areas was seen by 89.42% of subject participants, with an average summative reduction of 51.17% (Wilcoxon signed rank test, p=4.89e-17*). The improvement in FGID symptomatology over the course of digital therapeutics intervention (percent summative reduction) was not correlated with percent weight loss (Kendall=0.12, p=0.91), age (Kendall=−0.66, p=0.51), or gender (Wilcoxon sum rank, p=0.809). The methods also improved comorbid condition symptoms including: insomnia, sleep disorder symptoms, depression symptoms, anxiety symptoms, chronic inflammatory pain symptoms, and skin condition symptoms.

Individually, the methods implemented by the platform produced an average 45.93% reduction in severity of IBS (Wilcoxon signed rank, p=1.61e-08*), 61.01% average reduction in severity of bloating (Wilcoxon signed rank test, p=2.97e-16*), 38.55% average reduction in severity of gassiness (Wilcoxon signed rank, p=6.33e-12*), 61.69% average reduction in severity of cramping/belly pain (Wilcoxon signed rank, p=4.33e-12*), 37.54% average reduction in severity of constipation (Wilcoxon signed rank, p=3e-09*) and a 48.97% average reduction in severity of diarrhea (Wilcoxon signed rank, p=1.65e-07*).

As such, the model architecture generated and implemented genomic and microbiome predictors, which, when affected by the interventions of the personalized care plans, reduced summative symptom severity: In a linear D+G model of reduction in summative symptom severity, each additional risk allele for SNPs rs4639334 and rs7775228 returned by the model was associated with an increase in self-reported summative FGID symptom severity.

In a linear D+M model of reduction in summative FGID symptom severity, the returned gut microbial genera *Candidatus soleaferrea*, *Eubacterium hallii* group, *Alistipes*, and *Desulfovibrio* were all associated with an increase in summative FGID symptom severity. Microbial genera *Ruminococcus torques* group, *Intestinimonas*, unclassified genus GCA-900066575 of Lachnospiraceae family, and *Megasphaera* were all associated with self-reported reduction in summative FBD symptom severity.

In a linear D+G+M model of reported FGID symptom severity (Table 4), risk alleles of the same two SNPs returned by the model were again associated with an increase in self-reported summative FGID symptom severity, as were gut microbial genera *Desulfovibrio*, *Candidatus soleaferrea* and *Eubacterium ventriosum* group Microbial genera *Megasphaera*, unclassified genus CAG-352 of Rumniococcaceae family, *Ruminococcus torques* group, *Streptococcus* and *Intestinimonas* were all associated with self-reported reduction in summative FGID symptom severity. Adjusted $R^2$ values were 0.124 for the D+G model, 0.318 for the D+M model and 0.442 for the D+G+M model. This indicates that the fit of the models improved when adding microbiome predictors, with the best fit model for reduction in summative FGID symptom severity containing a mixture of genomic SNP and microbiome variables.

TABLE 4

Reduction in Summative FGID Symptom Severity Linear Model:
Demographics + Genomics + Microbiome (D + G + M)

| Variable | Estimate | Std. Error | t value | Pr(>|z|) |
|---|---|---|---|---|
| *Megasphaera* | 0.495 | 0.136 | 3.631 | <0.001* |
| *Desulfovibrio* | −0.517 | 0.105 | −4.910 | <0.001* |
| Unclassified genus CAG-352 of Rumniococcaceae family | 0.257 | 0.104 | 2.477 | 0.015* |
| Gluten Sensitivity (rs4639334), Risk Allele A | −2.013 | 0.792 | −2.541 | 0.013* |
| *Ruminococcus torques* group | 0.646 | 0.246 | 2.626 | 0.010* |
| Gluten Sensitivity (rs7775228), Risk Allele C | −1.936 | 0.828 | −2.338 | 0.022* |
| *Streptococcus* | 0.505 | 0.218 | 2.322 | 0.023* |
| *Intestinimonas* | 0.319 | 0.116 | 2.756 | 0.007* |
| *Soleaferrea* | −0.461 | 0.150 | −3.076 | 0.003* |
| *Eubacterium ventriosum* group | −0.290 | 0.134 | −2.157 | 0.034* |

IBS, Constipation, and Diarrhea: The models further returned results indicating that a reduction in IBS symptom severity was better explained by a mixture of genomic and microbiome predictors whereas reduction in diarrhea and constipation symptom severity was better explained by microbiome predictors only: Tables 5, 6, and 7 present linear D+G+M models for reduction of symptom severity for IBS, constipation and diarrhea, respectively (and D+M and D+G models were also implemented). Adjusted $R^2$ values for reduction in IBS symptom severity models were 0.130 for the D+G model, 0.432 for the D+M model and 0.487 for the D+G+M model. Adjusted $R^2$ values for reduction in constipation symptom severity models were 0.038 for the D+G model, 0.413 for the D+M model and 0.389 for the D+G+M model. Adjusted $R^2$ values for reduction in diarrhea symptom severity models were 0.090 for the D+G model, 0.610 for the D+M model and 0.528 for the D+G+M model. This shows that genomic SNP models performed rather poorly, and that the inclusion of microbiome variables always improved fit of the models. Interestingly, for IBS symptom reduction the D+G+M was the best fit model, whereas for constipation and diarrhea symptom reduction the D+M models were the best fit.

Results returned by the best-fit models indicated that Unclassified genus Clostridia UCG-014, *Escherichia-Shigella* and *Megasphaera* were associated with reduction of IBS symptom severity, whereas *Moryella, Fusicantenibacter* and risk alleles of rs7775228 (gluten sensitivity) were associated with an increase in IBS symptom severity.

For constipation there were only microbial taxa in the D+M model: *Parabacteroides*, Unclassified genus of Anaerovoracaceae Family XIII AD3011 group, *Lachnospira* and *Terrisporobacter* were associated with reduction in symptom severity, whereas *Eubacterium coprostanoligenes* group was associated with increase. For diarrhea change in symptom severity, as for constipation, only microbial taxa were found significant in the D+M model: *Intestinimonas, Prevotella, Lactobacillus* and *Phascolarctobacterium* were associated with reduction in symptom severity, while Unclassified genus UCG-009 of Butyricicoccaceae family was associated with increase.

TABLE 5

Reduction in IBS Symptom Severity Linear Model: Demographics +
Genomics + Microbiome (D + G + M)

| Variable | Estimate | Std. Error | t value | Pr(>|z|) |
|---|---|---|---|---|
| Gluten Sensitivity (rs7775228), Risk Allele C | −0.566 | 0.225 | −2.515 | 0.016* |
| Unclassified genus *Clostridia* UCG-014 | 0.092 | 0.024 | 3.844 | <0.001* |
| *Escherichia-Shigella* | 0.087 | 0.028 | 3.122 | 0.003* |
| *Fusicatenibacter* | −0.096 | 0.038 | −2.501 | 0.016* |
| *Megasphaera* | 0.101 | 0.034 | 3.007 | 0.004* |
| *Moryella* | −0.079 | 0.028 | −2.775 | 0.008* |

Adjusted $R^2$: 0.487

TABLE 6

Reduction in Constipation Symptom Severity Linear Model:
Demographics + Genomics + Microbiome (D + G + M)

| Variable | Estimate | Std. Error | t value | Pr(>|z|) |
|---|---|---|---|---|
| *Parabacteroides* | 0.231 | 0.073 | 3.174 | 0.003* |
| *Eubacterium coprostanoligenes* group | −0.161 | 0.051 | −3.125 | 0.003* |
| *Lachnospira* | 0.123 | 0.047 | 2.606 | 0.013* |
| Gluten Sensitivity (rs7775228), Risk Allele C | 0.757 | 0.327 | 2.311 | 0.026* |

Adjusted $R^2$: 0.389

TABLE 7

Reduction in Diarrhea Symptom Severity Linear
Model: Demographics + Genomics +
Microbiome (D + G + M)

| Variable | Estimate | Std. Error | z value | Pr(>|z|) |
|---|---|---|---|---|
| *Ruminococcus torques* group | 0.203 | 0.076 | 2.669 | 0.013* |
| *Lactobacillus* | 0.114 | 0.042 | 2.706 | 0.012* |
| Unclassified genus UCG-009 of Butyricicoccaceae family | −0.107 | 0.035 | −3.045 | 0.005* |
| *Prevotella* | 0.069 | 0.031 | 2.249 | 0.034* |

Adjusted $R^2$: 0.528

For the set of subjects being analyzed and treated, implementation of personalized intervention plans produced an average 1.01% reduction in A1C values, up to 89% reduction in digestive disorder symptoms (e.g., associated with constipation, associated with diarrhea, associated with abdominal pain, etc.), up to 75% reduction in insomnia/sleep disorder symptoms (e.g., in relation to restfulness of sleep, in relation to duration of sleep, in relation duration of wake, in relation to duration of sleep associated with different phases of sleep, etc.), up to 66% reduction in depression/anxiety symptoms, up to 66% reduction in chronic inflammatory pain symptoms, up to 50% reduction in chronic acne/eczema symptoms, and up to 5% more weight loss, in comparison to baseline states (e.g., assessed prior to implementation of the personalized intervention plans, assessed relative to control groups not provided with personalized intervention plans).

Of the subjects enrolled who successfully lost 5% or more body weight through a digital therapeutics program, 104 presented one or more FGIDs. These FGID sufferers were significantly different from the non-FGID group in terms of gender and the BMI at time of sampling, based upon analyzed model outputs. Additionally, model outputs indicated that gender was significantly associated with the composition of baseline gut microbiome samples in these subjects. Thus, using gender as a demographic variable, the system(s) and method(s) described were configured for training of linear and logistic regression models to differentiate FGID status using D+G, D+M, and D+G+M variables. The models confirmed that female gender was associated with higher prevalence of FGID as seen in the logistic regression D+G model, where females were 3.26 times more likely to be FGID sufferers than males while holding genomic predictors constant. Additionally, when baseline microbiome was added to the model (D+G+M model), females were on average 2.26 times more likely to suffer from FGID than males while holding constant both genomic and microbial predictors. Thus, some of the gender association in the D+G model is explained by microbiome variables in the D+G+M model, reinforcing the role of gender in shaping the baseline gut microbiome of subjects.

Of note, the SNP associated with gluten sensitivity (rs2187668, risk allele T) was seen to be strongly associated with FGID status, with relevance to characterizations of celiac disease patients. Interestingly, the D+G+M model did not select any genomic variables and was identical to the D+M model, and not surprisingly the pseudo $R^2$ scores for these models are similar (0.227 for D+G+M vs 0.220 for D+M). Both of these models have pseudo $R^2$ scores higher than for the D+G model (0.089), indicating that baseline microbiome better classified participants having FGID than models based on genomic predictors, and furthermore, that the addition of SNPs did not improve classification of FGID by gender plus baseline microbiome. Of the microbiome taxa variables identified in the models, many have been already reported in the literature associated with FGIDs. Previous studies show strong association of the *Ruminococcus torques* group with FGIDs.

Models implemented by the systems and methods then assessed the change in reported symptom severity over the course of the digital therapeutics program. In total, 89.42% of subjects experienced significant reduction of severity of at least one symptom. This improvement in symptom severity was not correlated with percent weight loss, gender, or age. Reduction in symptom severity was significant for all six symptoms investigated individually, and for summative symptom severity (all of them together). When the architecture modeled the reduction in summative FGID symptom severity over the course of digital therapeutics intervention, the model architecture returned results identifying the D+G+M linear model as the best fitting, with an adjusted $R^2$ of 0.442, compared with 0.124 for the D+G model and 0.318 for the D+M model. For these participants, 2 genomic SNPs and 8 microbial taxa were the significant predictors in the best model. Thus, gender and baseline microbiome best classified subjects with or without symptoms, whereas a combination of genomic SNPs and microbiome variables best modeled reduction in summative FGIDs symptom severity.

The models further returned results enabling examination of reduction of symptom severity for three functional bowel disorders of interest: IBS, constipation and diarrhea. For IBS the best-fit model was the one containing D+G+M variables, whereas for constipation and diarrhea, the best-fit models were those only containing D+M variables. When analyzing the variables found significant to the best fit models for this cohort, the inventions were used to identify a number of genomic SNPs and microbial taxa that are shared across two or more models. SNP rs7775228 (risk allele C) was associated in the linear D+G+M model with increase in summative symptom severity (Table 5), as well as in the linear D+G+M model with increase in IBS symptom severity (Table 6). Interestingly, despite not being the best fit models, it also was associated in the linear D+G model with increase in diarrhea symptom severity and associated in the linear D+G+M model with reduction of constipation symptom severity. In addition to its association with gluten sensitivity, which is the reason why the invention(s) include this SNP as part of the care protocols, rs7775228 has been shown involved in seasonal allergic rhinitis and as a protein biomarker for inflammation.

In terms of the microbial taxa shared across two or more models, genus *Fusicatenibacter* was associated with greater prevalence of FGID in the D+G+M logistic model of this cohort, and associated with increase in IBS symptom severity in the D+G+M linear model. Genus *Intestinimonas* was associated with reduction in summative FGID symptom severity in the D+G+M model, and also with reduction in diarrhea symptom severity in the D+M model. Genus *Megasphaera* was noted to be strongly associated with reduction in summative FGID symptom severity in the D+G+M linear model of Table 5 and also associated with reduction in IBS symptom severity in the D+G+M linear model of Table 6. Interestingly, genus *Lactobacillus* appears associated with reduction in diarrhea symptom severity in the linear D+M model. Moreover, these bacteria, specifically, *Fusicatenibacter, Megasphaera* and *Intestinimonas* which were either negatively associated with FGID status or were associated with reduction in severity of FGID symptoms are previously reported to be Short Chain Fatty Acids (SCFAs) producers.

The analyses also revealed some novel bacterial signatures that were associated with FGID status. *Desulfovibrio* was observed to possess significant association with increase in FGID symptomatology. *Ruminococcus torques* group appears associated with FGID status in the D+G+M logistic model, and associated with reduction in summative FGID symptom severity in the D+G+M model. Despite not being the best fit model, this taxa also was associated with reduction of diarrhea symptom severity in the linear D+G+M model. Additionally, genus *Terrisporobacter*, known to be associated with inflammation and gut dysbiosis, was associated with FGID status in the D+G+M logistic model. Collectively, these returned model outputs indicate a potential of gut microbial profiling not only for predicting current gastrointestinal health, but also for generating personalized care plans for the reduction in FGID related symptoms, as was performed in an exemplary manner here.

Variations of the specific implementations of the models for FGID and gastrointestinal health condition symptoms can include: adjusting model architecture for different demographics/cohorts of subjects/health conditions; utilization of other genomic loci; demographic data; lifestyle data (e.g., associated with intolerances and allergies, associated with probiotic use, associated with pre-biotic use, associated with antibiotic use, etc.); other microbiome data (e.g., associated with other taxonomic groups, associated with other functional products produced by microbiome constituents, etc.); comorbidity data (e.g., associated with one or more of: musculoskeletal pain, skin conditions, hypothyroidism, diabetes, cholesterol, hypertension, mental health, etc.); clinical instruments to rate symptom severity over the course of the personalized treatment plan; and/or other information to improve results of the personalized care plans.

Still, the exemplary systems and methods described achieved reduction in symptom severity of FGIDs, including IBS, diarrhea and constipation. Such results support use of the personalized care plans as a therapy for insulin resistance, empowering subjects to manage their inflammation by awareness of the impact of processed foods and foods to which they are sensitive as per their genomic SNPs and microbiome results. Dietary fiber coaching also results in increased vegetable diversity and quantity. The microbial taxa identified in the models and their corresponding effect on reduction of FGIDs symptom severity, provides support for associations of a number of microbial taxa in the prognosis of FGIDs symptomatology. Moreover, the methods presented here can be readily implemented to study other comorbidities where genetics and gut microbiome play a role in disease etiology.

2.5.2 Method Exemplary Execution and Performance—Cardiovascular Conditions, Obesity, and Associated Comorbidities In an exemplary application, the platform can provide mechanisms for prevention and/or treatment of cardiovascular conditions, including conditions associated with insulin regulation (e.g., diabetes, other conditions described), obesity, overweightness, and/or other comorbidities. In an exemplary implementation, genome SNP data (e.g., through SNP genotyping), gut microbiome data (e.g., through sampling and gut microbiota analysis), lifestyle information, and other factors disclosed above were generated from subjects, processed with model architecture, and used to provide care through a personalized digital care program that delivered both human and digital personalized coaching for lifestyle changes (e.g., diet and exercise guidance) through mobile and web application components, with the goal of producing groundbreaking performance in weight loss achievements by subjects. In the exemplary application, the cohort of subjects completed at least 100 days in their respective personalized weight loss programs, which provided next-generation, prescription-grade, digital therapeutics based on processing genetic data, microbiome data, lifestyle data, and demographics to individualized dietary and lifestyle regimens using artificial intelligence (AI). Participating subjects achieved over 5% reductions in baseline body weight, with reversals in weight-related inflammatory gut, musculoskeletal, cardiovascular, mental health, and insulin-related comorbidities. Additional details of sample acquisition, processing, model architecture, and AI-informed personalized care programs generated are provided as follows:

Upon enrollment, participating subjects were provided with online login access to the platform through an application interface, which provided digital objects for facilitating completion of a health questionnaire to extract demographic, lifestyle, and other data. Subjects were also provided with a digital weighing scale and buccal swab and stool sampling kits. The application provided to participating subjects included tools for tracking subjects' weight (e.g., by way of the digital weighing scale), assessing dietary intake (e.g., through machine vision processing and manual entry of information associated with uploaded photographs of food items consumed), and tracking wellness and lifestyle associated metrics (e.g., sleep quality and quantity, exercise type and duration, stress and meditation, energy levels, cravings, recommended foods consumed/avoided, etc.). Dietary intake was assessed by coaches who assigned a nutrient density score to meals based on their inflammatory, fiber diversity and expected insulin response.

Then, based on processing of genetic data, gut microbiome profiles upon processing of buccal and gut sample/fecal swab samples, lifestyle data, and demographic information with trained model architecture, a wellness report was generated for participating subjects based upon returned model outputs. Model outputs were returned regularly, and results were evaluated with the participants one-on-one by a health coach over the course of four months at predetermined weekly and bi-weekly intervals. The personalized care programs for each participant were tuned to produce incremental lifestyle changes focused on reducing sugar consumption, timing meals to optimize insulin sensitivity, reducing systemic inflammation by identifying possibly inflammatory and anti-inflammatory nutrients, and increasing fiber diversity to improve gut health. These behavioral changes were implemented with the help of virtual health coaching and the application to ensure that these changes were habit forming and sustainable.

Sample collection and processing: Genome SNP array and gut microbiome profiling: In examples, subjects self-collected saliva samples with buccal swabs and gut samples with fecal swabs with standardized directions provided. The platform also performed nucleic acid extraction, purification, and genotyping for the saliva sample (e.g., with an Affymetrix GeneTitan platform, with an Infinium Global Screening Array iScan System, etc.). The platform performed sample processing of baseline (pre-intervention) microbiome samples, followed by 16S rRNA gene amplicon sequencing to generate a set of sequencing reads, and DNA extraction (e.g., using Qiagen MagAttract Power Microbiome DNA Kit) by way of an automated liquid handling and DNA extraction instrument. The platform amplified the amplicon regions of 16S rRNA (e.g. V4 region, V3-V4 region, V3-V5 region, full length 16S rRNA gene) and sequenced amplicons (e.g., using an Illumina MiSeq platform with 2×300 bp paired-end sequencing). Sequence reads were then demultiplexed and ASVs generated (e.g., using the DADA2 package). Primers and low quality bases (e.g., with a threshold of Q<30) were trimmed from the reads, and chimeras were removed. The platform then performed taxonomic annotation using a Naive Bayes classifier against the 99% non redundant SILVA 138 reference database; however, variations of the methods described included taxonomic annotation performed by way of VSEARCH against the SILVA reference database. Hits to mitochondria, chloroplast, eukaryota, and unassigned taxa (e.g., at the phylum level, at other taxonomic levels) were excluded; however, variations of the examples described can include non-exclusion of such taxa.

Statistical Model Architecture: Data from subjects (with genome SNP and/or microbiome data) over the course of participating in the personalized digital care program were processed as follows. Input variables included demographic variables (e.g., gender, age, weight and body mass index taken in coordination with repeated instances gut microbiome sample collection and weight measurements acquired through use of the digital scales), engagement variables (e.g., food photos posted, days in program, coaching sessions completed, exercise entries, cravings logged), genomic loci/SNP data, and baseline gut microbiome data. In examples, Wilcoxon sum rank/signed rank test or Kendall correlation test, as appropriate, were implemented by model architecture. Significance results were adjusted for multiple comparisons using false discovery rate (FDR) correction method for the microbiome data.

Genome Loci/SNP-Related Statistical Model Architecture: 197 SNP predictors derived from curated panels associated with obesity, fitness, nutrient metabolism and inflammatory markers were used for personalized interventions of subjects. According to model architecture, each SNP value was encoded as the number of risk alleles (0, 1, or 2) for each subject. As such, the multi-omic model can include a first subarchitecture for processing SNP-associated input data, said first subarchitecture structured to detect and encode values of a set of risk alleles of the genomic profile for the subject.

Microbiome-related Statistical Model Architecture: Model architecture was structured to return bacterial genera abundances, using Qiime276, qiime2Rn and phyloseq. In examples, model architecture was structured to filter some microbial features from downstream analysis. In more detail: (a) Amplicon sequence variants (ASVs) not classified at the phylum level, (b) phyla that had <25 ASVs, (c) uncultured and Incertae Sedis taxa, (d) genera that had <30 reads in at least 15% of samples, and (e) genera for which >25% of samples had zero read count were filtered from downstream analyses. Model architecture was structured to transform abundances of bacterial genera to centered log-ratio (CLR) (e.g., using the zCompositions package) after first replacing zeros with pseudo counts based on a Bayesian-multiplicative replacement (e.g., from the zCompositions package). Model architecture was structured to perform permutational multivariate analyses of variance (PERMANOVA) on gut microbiome Aitchison distance matrices, using gender, BMI (e.g., BMI values closest to dates of gut microbiome sampling) and weight loss as variables using the CLR transformed abundances. Additionally, model architecture was structured to transform read counts after zero replacement using additive log ratio (ALR), to be utilized in downstream model statistics. As such, the multi-omic model can include a second subarchitecture for processing microbiome-associated input data, said second subarchitecture structured to return bacterial taxonomic abundances of the baseline microbiome state, said second subarchitecture further structured to filter out ASVs not classified at the phylum level, phyla having less than 25 ASVs, Incertae Sedis data (and other filtering criteria), and said second subarchitecture further structured to transform bacterial taxonomic abundances to centered log-ratio (CLR) values.

Higher-Level Model Architecture: Model architecture included linear and logistic regression models. Outputs of model architecture were processed and visualizations were generated (e.g., using the R stats, ggplot2, pscl, car, pROC, Metrics, caret, glmnet, tidyverse, lubridate, imputeTS and ggpubr packages). In examples, in order to utilize lasso regression for variable selection prior to fitting linear and logistic models, SNPs for which a proportion of subjects had missing values (e.g. >5%, >10%, >15%, >20%, or any other percentage) were removed, followed by imputing remaining missing loci/SNP reads to their most frequent value (i.e., mode). To avoid poor performance in regression models, variables with Pearson correlation to another variable above a certain threshold (e.g. >=75%, >=80%, >=85%, or any other percentage) were removed.

Then, for regression models, the model architecture was structured to transform bacterial abundance data using an additive log-ratio (ALR) operation, which maintains subcompositional coherence, permitting genera to be removed in downstream analysis (e.g., removing insignificant predictors from a regression model). For this, the easyCoda package was employed to analyze all 105 microorganism (e.g., microbial genera) utilizing variances, variances explained, and Procrustes correlations to select candidate references for ALR. An additional criterion employed by the model architecture was a prevalence criterion, as zero values are problematic with log-ratios. Based on these criteria, Blautia was the selected reference for the gastrointestinal condition model. In all cases of highly correlated microbe pairs, the unclassified microbe was removed, or if both were unclassified, then the microorganism with the larger mean absolute correlation in that dataset was removed. In all cases of highly correlated microbe pairs, the unclassified microbe was removed, or if both were unclassified, then the microbe with the larger mean absolute correlation in that dataset was removed. This resulted in removal of microbes from regression models incorporating microbial predictors. According to model architecture, gender and locis (e.g., SNPs) were scaled to a range between −1 and 1.

According to model architecture, demographic input variables included gender, age, and baseline BMI. Behavioral engagement variables (e.g., number of coaching sessions, number of food photos posted in the application, number of logged exercise sessions, logged cravings, number of weight entries posted in the application, number of tasks completed, number of energy entries, number of meditation entries, and recorded stressor events, etc.) were represented as the average number per day (ex: 3 food photos, 1 weight entry, 0.1 coaching sessions per day). Number of days in the program was also included as a predictor. The number of energy entries and number of meditation entries variables were removed in preprocessing due to high correlation of >=0.8 with the number of stress entries variable, resulting in 7 engagement variables (average per day) along with the number of days in the program remaining as predictors for the Demographic/Engagement models.

After the above data preparation, lasso regression model architecture was employed for variable selection in the modeling of datasets, retaining predictors having non-zero coefficients with optimal lambda chosen by 5-fold cross-validation grid search. The lambda resulting in the minimum mean cross-validated error was selected, or if this resulted in a paucity of predictors, then a plateau lambda in the error vs lambda plot having sufficient number of predictors was selected. Model architecture employed mean squared error in linear lasso regression, and employed McFadden pseudo $R^2$ in logistic regression models. After lasso regression, model architecture employed a step function (stats package), using Akaike information criterion (AIC) to obtain a high-quality fit. If any insignificant variables remained, these were removed one-by-one from the least significant variable resulting in a final interpretable model for each investigation and set of predictors.

After pre-processing, model architecture was structured to fit regression models to variables producing coefficients to describe the impact of each predictor on the modelled outcome in the cohort. As described above, for each model subarchitecture, the step function was employed, followed by removal of any remaining insignificant variables, resulting in the final interpretable models. Linear regression model outputs were fitted to subjects' percent weight loss. Logistic regression model outputs were fitted to success/failure of losing weight with the intervention. Success was defined as 5% or greater weight loss, failure as weight gain or negligible change (e.g., less than 2 lbs. weight change).

Results: In total, subjects who had completed at least 100 days in a digital therapeutics program generated based upon the described model architecture, successfully lost weight and had reductions in weight/obesity-related comorbidities. In more detail, the personalized digital therapeutics program provided digitally delivered recommendations alongside health coaching to drive active engagement of subjects. In the exemplary implementation, over 75% of enrolled subjects lost weight, and over 13% maintained a stable weight.

Figure 5:
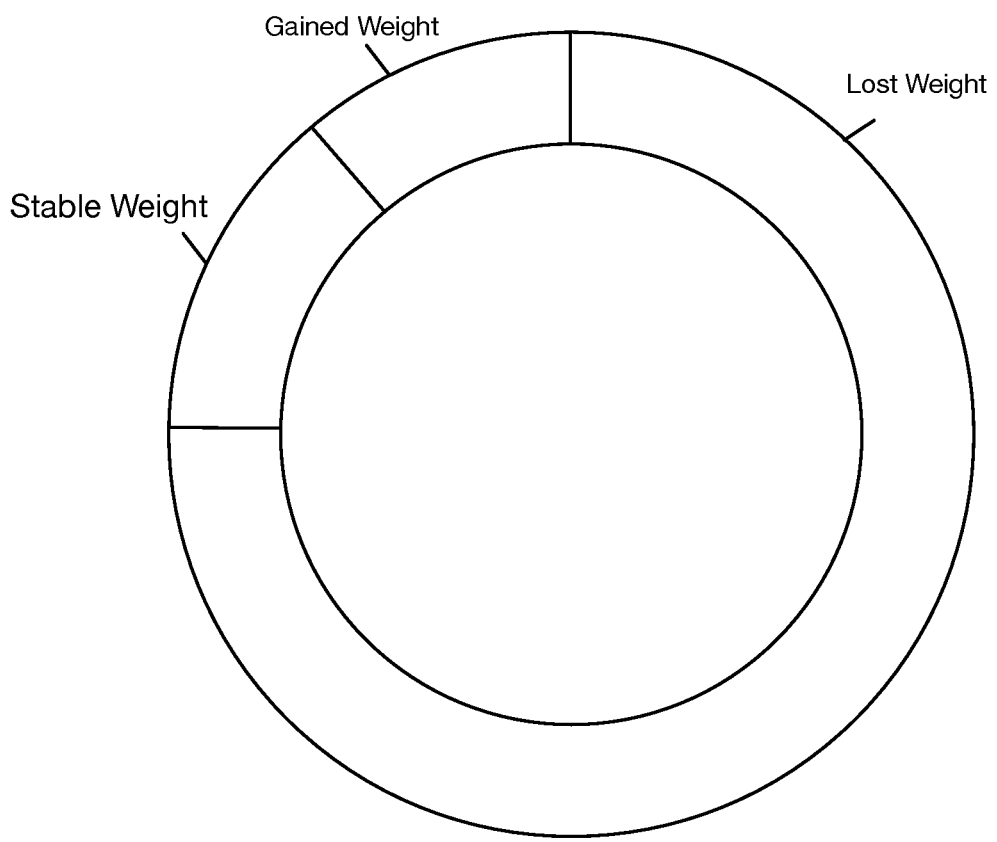
FIG. 5 depicts exemplary results in weight reduction for subjects with FGID symptoms and comorbid conditions.

Subjects, on average, achieved and maintained $\geq$5% weight loss, as shown in FIG. 5).

Genomic SNPs and gut microbiome taxa improve body weight loss models: The logistic regression model architecture modeled the associations of demographic (D), engagement (E), genome SNP (G) and baseline gut microbiome (M) variables with body weight loss in the cohort (Tables 8, 9, 10, and 11), fitting separate average effect size for each predictor while controlling for all other model variables. The D+E model correlation between predicted and actual percent weight loss was 0.24, with a mean squared error (MSE) of 30.5 (Table 8). As such, model architecture can be structured to return a set of SNP features, wherein the set of SNP features comprises characterizations of risk allele detection for the subject, for a set of SNPs comprising SNPs in tables shown and/or other SNPs.

TABLE 8

Percentage Weight Loss model: Linear Engagement Mode

| Variable | Fitted coefficient | P-Value |
|---|---|---|
| Days in Program | 0.009 | 0.00183 |
| Engagement (e.g., Food Photos Posted Per Day) | 1.136 | 9.55e−05 |
| Coaching Sessions Completed Per Day (average) | 30.419 | 0.01302 |

In a second logistic model, model architecture was structured to return associations of D+E+M together on body weight loss (Table 9). The addition of baseline microbiome predictors (correlation 0.3, MSE 29.5) improved model accuracy.

TABLE 9

Percentage Weight Loss Per Engagement or Microbiome Profile, Linear Model

| Variable | % Weight Loss | P-value |
|---|---|---|
| Days in Program | 0.010139 | 0.000574 |
| Food Photos Posted Per Day (average) | 1.065847 | 0.000231 |
| Coaching Sessions Completed Per Day (average) | 31.109873 | 0.010186 |
| [Ruminococcus]_gauvreauii_group | −0.305268 | 0.000529 |
| Subdoligranulum | 0.232517 | 0.022100 |
| [Eubacterium]_brachy_group | 0.195361 | 0.038772 |
| [Eubacterium]_nodatum_group | −0.197467 | 0.035873 |

With a third model architecture structure to process associations of D+E+G variables together on body weight loss (Table 10), the addition of genomic (correlation 0.43, MSE 26.4) predictors improved model accuracy.

TABLE 10

Percentage Weight Loss Per Engagement or Genetic Risk, Linear Model

| Variable | % Weight Loss | P-value |
|---|---|---|
| Days in Program | 0.009 | 0.001705 |
| Food Photos Posted Per Day (average) | 1.116 | 5.4e−05 |
| Coaching Sessions Completed Per Day (average) | 26.928 | 0.022968 |
| rs2016520 | 1.225294 | 0.001023 |
| rs6968554 | −0.667489 | 0.028725 |
| rs17700633 | −1.128314 | 0.000532 |
| rs29941 | 0.873933 | 0.004322 |

TABLE 10-continued

Percentage Weight Loss Per Engagement or Genetic Risk, Linear Model

| Variable | % Weight Loss | P-value |
|---|---|---|
| rs2185570 | 1.142849 | 0.021738 |
| rs1800566 | −0.769662 | 0.026924 |
| rs10246939 | 0.750911 | 0.010244 |
| rs6318 | 1.000176 | 0.007534 |
| rs762551 | 0.812917 | 0.010957 |
| rs4654748 | −1.060840 | 0.000363 |
| rs11076023 | 0.715936 | 0.015810 |
| rs12611820 | 0.830458 | 0.015397 |
| rs2112347 | 0.677719 | 0.026135 |
| rs1260326 | 0.655095 | 0.035332 |
| rs526934 | −0.689348 | 0.047765 |

An additional gain of fit was achieved with a fourth model structured to analyze D+E+G+M variables together in relation to body weight loss (Table 11; correlation 0.46, MSE 25.4).

TABLE 11

Percentage Weight Loss Per Engagement with Microbiomic and Genetic Profile, Linear Model

| Variable | Estimate | P-value |
|---|---|---|
| Food Photos Posted Per Day (average) | 0.933190 | 0.000655 |
| Rs4654748 | −1.024550 | 0.000499 |
| Rs2016520 | 1.202316 | 0.001066 |
| Rs6968554 | −0.621730 | 0.037746 |
| Rs17700633 | −1.108252 | 0.000601 |
| [Ruminococcus]_gauvreauii_group | −0.323827 | 9.22e−05 |
| Days in Program | 0.010364 | 0.000223 |
| rs29941 | 0.798770 | 0.007845 |
| Rs2185570 | 1.284483 | 0.009163 |
| Coaching Sessions Completed Per Day (average) | 33.406705 | 0.004204 |
| Rs762551 | 0.789841 | 0.012392 |
| rs12611820 | 0.787465 | 0.020534 |
| rs2112347 | 0.718392 | 0.016897 |
| rs6318 | 0.843827 | 0.021887 |
| Rs11076023 | 0.692699 | 0.017922 |
| Rs6994076 | 0.676072 | 0.022291 |
| Subdoligranulum | 0.227602 | 0.018383 |
| rs4680 | 0.554019 | 0.050977 |
| Rs7385804 | −0.668658 | 0.041690 |
| Rs1800566 | −0.722207 | 0.034516 |
| rs526934 | −0.688317 | 0.044708 |
| rs526934 | −1.061404 | 0.047775 |

Table 12 reports the impact of the D+E variables on success/failure to lose 5% of body weight by 423 subjects (McFadden pseudo $R^2$=0.10), as defined above. Table 13 represents values from the same logistic regression model based on D+E+G variables (McFadden pseudo $R^2$=0.20), Table 14 represents values from the same logistic regression model based on D+E+M variables (McFadden pseudo $R^2$=0.12), and Table 15 includes all variables: D+E+M+G (McFadden pseudo $R^2$=0.20).

TABLE 12

Success/Failure in 5% Weight Loss model: Logistic Engagement Model

| Variable | Odds Ratio | 2.5% CI | 97.5% CI |
|---|---|---|---|
| Days in Program | 0.32 | 0.15 | 0.69 |
| Food Photos Posted Per Day (average) | 1.84 | 1.24 | 2.80 |
| Coaching Sessions Completed Per Day (average) | 1.10e+07 | 9.92e+1 | 1.73e+12 |

TABLE 12-continued

Success/Failure in 5% Weight Loss
model: Logistic Engagement Model

| Variable | Odds Ratio | 2.5% CI | 97.5% CI |
|---|---|---|---|
| Exercise Entries Per Day (average) | 3.78 | 1.41 | 9.85 |
| Cravings Logged Per Day (average) | 0.24 | 0.06 | 0.85 |

TABLE 13

Percentage Weight Loss Per Engagement
or Genetic Risk, Logistic Model

| Variable | Odds Ratio | 2.5% CI | 97.5% CI |
|---|---|---|---|
| Food Photos Posted Per Day (average) | 1.728460 | 1.1431186 | 2.699787 |
| Coaching Sessions Completed Per Day (average) | 1.064178e+06 | 5.8336189 | 2.930138e+11 |
| Exercise Entries | 2.872685 | 1.0603978 | 8.816437 |
| Gender | 4.736816e−01 | 0.2529803 | 8.623200e−01 |
| rs4654748 | 5.689331e−01 | 0.4088875 | 7.845057e−01 |
| rs11076023 | 1.781088 | 1.2760146 | 2.510822 |
| rs660339 | 6.0727436−01 | 0.4266722 | 8.568704e−01 |
| rs6994076 | 1.577059 | 1.1418210 | 2.196684 |
| rs2815752 | 6.283290e−01 | 0.4391151 | 8.890215e−01 |
| rs17700633 | 6.980782e−01 | 0.4920205 | 9.868498e−01 |
| rs2241766 | 6.119230e−01 | 0.3785443 | 9.856039e−01 |
| rs1800795 | 6.472841e−01 | 0.4491182 | 9.276035e−01 |
| rs29941 | 1.399105 | 1.0000055 | 1.969223 |
| rs526934 | 6.583905e−01 | 0.4541079 | 9.482034e−01 |
| rs838147 | 6.565913e−01 | 0.4643377 | 9.202014e−01 |

TABLE 14

Percentage Weight Loss Per Engagement or Microbiome Profile, Logistic Model

| Variable | Odds Ratio | 2.5% CI | 97.5% CI |
|---|---|---|---|
| Days in Program | 1.003181e+00 | 1.00036356 | 1.006086e+00 |
| Food Photos Posted Per Day (average) | 1.859673e+00 | 1.24246429 | 2.864282e+00 |
| Coaching Sessions Completed Per Day (average) | 4.800462e+07 | 334.59537796 | 9.878126e+12 |
| Exercise Entries | 3.514510e+00 | 1.30365729 | 1.081409e+01 |
| Cravings Entries | 2.106750e−01 | 0.05669355 | 7.770015e−01 |
| Gender | 5.578597e−01 | 0.31151500 | 9.738602e−01 |
| *Blautia* | 6.952023e−01 | 0.52258469 | 9.142857e−01 |
| *Anaerostipes* | 1.197374e+00 | 1.00036507 | 1.441664e+00 |
| *[Ruminococcus]_gauvreauii*_group | 9.188178e−01 | 0.84207617 | 1.001035e+00 |

TABLE 15

Percentage Weight Loss Per Engagement with Microbiomic
and Genetic Profile, Logistic Model

| Variable | Odds Ratio | 2.5% CI | 97.5% CI |
|---|---|---|---|
| Food Photos Posted Per Day (average) | 1.728460e+00 | 1.1431186 | 2.699787e+00 |
| rs4654748 | 5.689331e−01 | 0.4088875 | 7.845057e−01 |
| rs11076023 | 1.781088e+00 | 1.2760146 | 2.510822e+00 |
| rs660339 | 6.072743e−01 | 0.4266722 | 8.568704e−01 |
| Exercise Entries | 2.872685e+00 | 1.0603978 | 8.816437e+00 |
| rs6994076 | 1.577059e+00 | 1.1418210 | 2.196684e+00 |
| rs2815752 | 6.283290e−01 | 0.4391151 | 8.890215e−01 |
| rs17700633 | 6.980782e−01 | 0.4920205 | 9.868498e−01 |
| Gender | 4.736816e−01 | 0.2529803 | 8.623200e−01 |
| Rs2241766 | 6.119230e−01 | 0.3785443 | 9.856039e−01 |
| rs1800795 | 6.472841e−01 | 0.4491182 | 9.276035e−01 |
| Coaching Sessions Completed Per Day (average) | 1.064178e+06 | 5.8336189 | 2.930138e+11 |
| rs526934 | 6.583905e−01 | 0.4541079 | 9.482034e−01 |
| rs838147 | 6.565913e−01 | 0.4643377 | 9.202014e−01 |
| rs29941 | 1.399105e+00 | 1.0000055 | 1.969223e+00 |

Additionally or alternatively, genomic SNP variables (e.g., rsids) that can be used to inform or intervene with respect to cardiometabolic health can include one or more of: rs10246939, rs1042713, rs10741657, rs11076023, rs1260326, rs12611820, rs1501299, rs17300539, rs17700633, rs1799931, rs1800566, rs1800795, rs2016520, rs2112347, rs2185570, rs2241766, rs236918, rs2815752, rs29941, rs4074995, rs4654748, rs4680, rs526934, rs6318, rs660339, rs6968554, rs6994076, rs7138803, rs7385804, rs762551, rs7903146, rs838147, rs9376026.

Figure 6A:
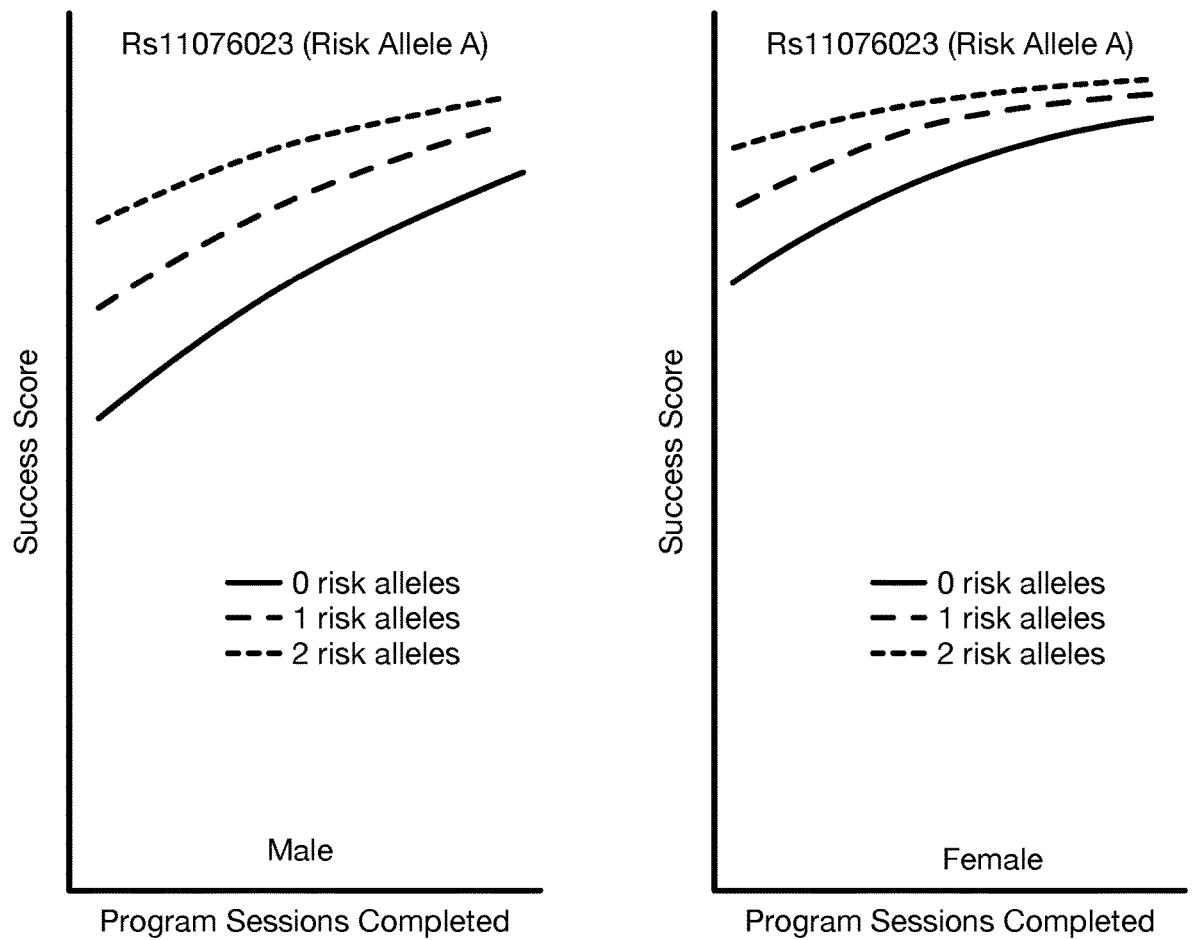
FIGS. 6A-6E depict exemplary results associated with genomic and microbiome markers used to guide personalized care regimen components according to methods described.
Figure 6B:
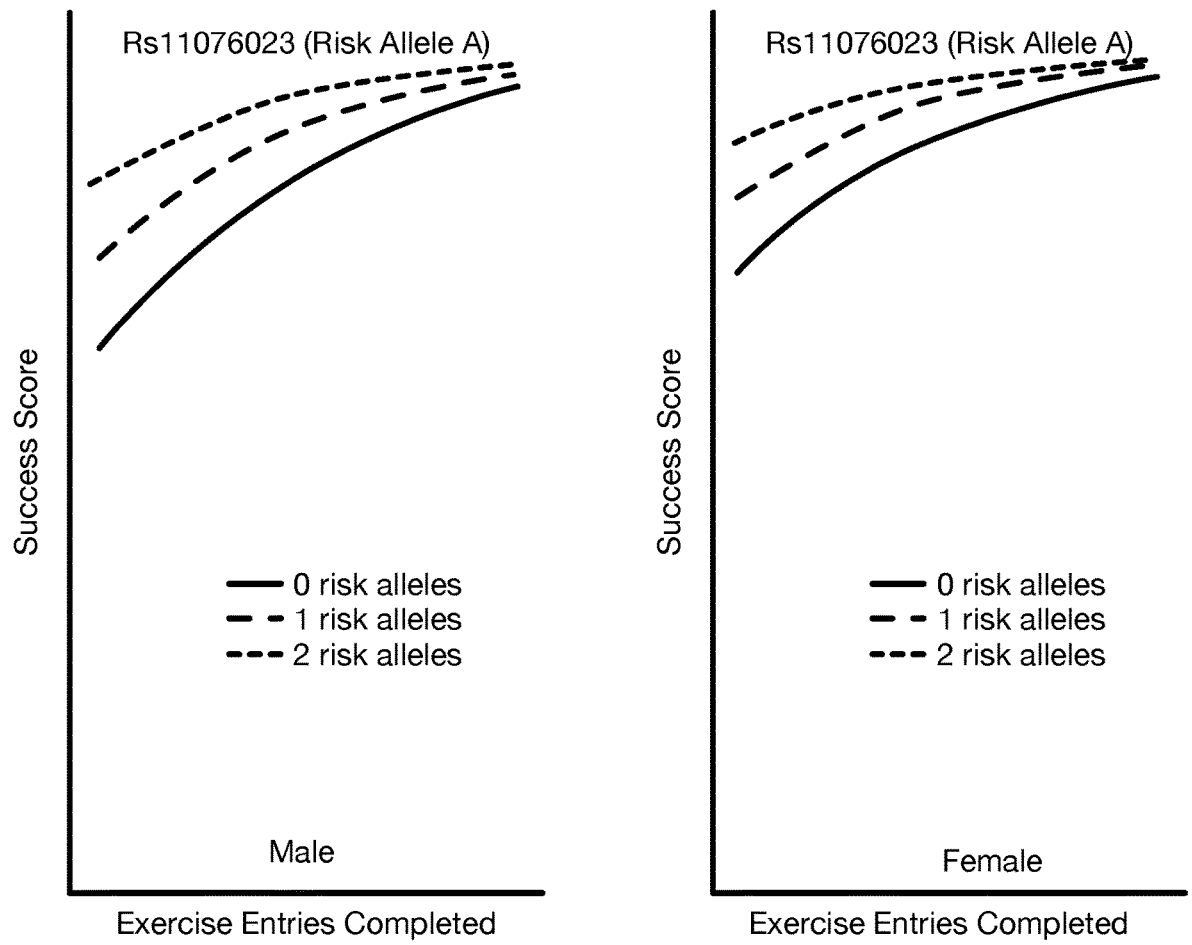
Figure 6C:
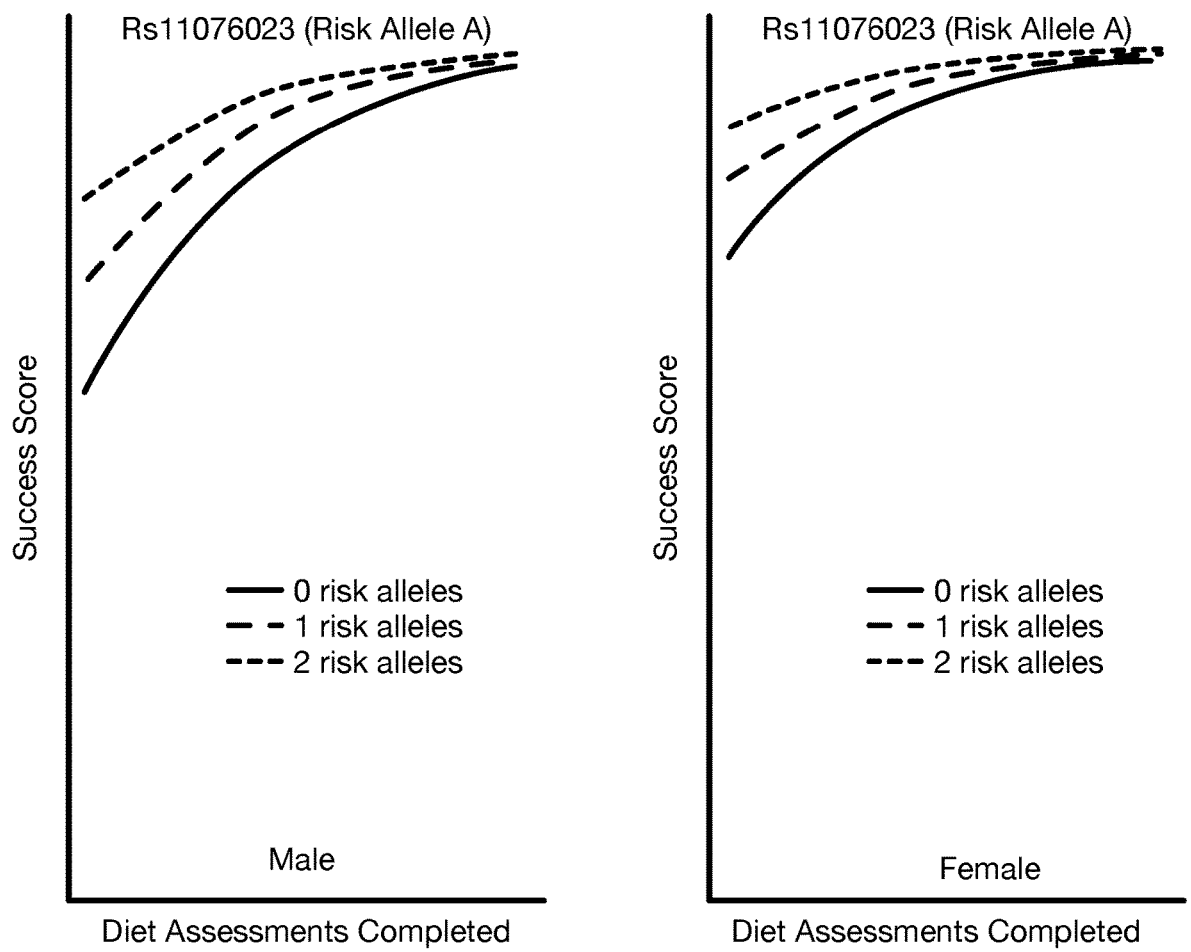

In examples, the model outputs provided insights into the interplay between genomic SNPs and engagement variables. For example, for Rs11076023 (an SNP associated with weight gain on a high carbohydrate diet), risk alleles observed and processed correlated positively with success score (e.g., an increase from 0 to 1 to 2 SNP risk alleles was correlated with an increase in success score). FIG. 6A demonstrates results indicating that an increased number of coaching sessions is associated with increased success score in all three risk groups (panel A for females and panel B for males). FIG. 6B shows the association of Rs11076023 and logged exercise, and FIG. 6C shows the association of Rs11076023 and food posts (panels A for females and panels B for males).

Figure 6D:
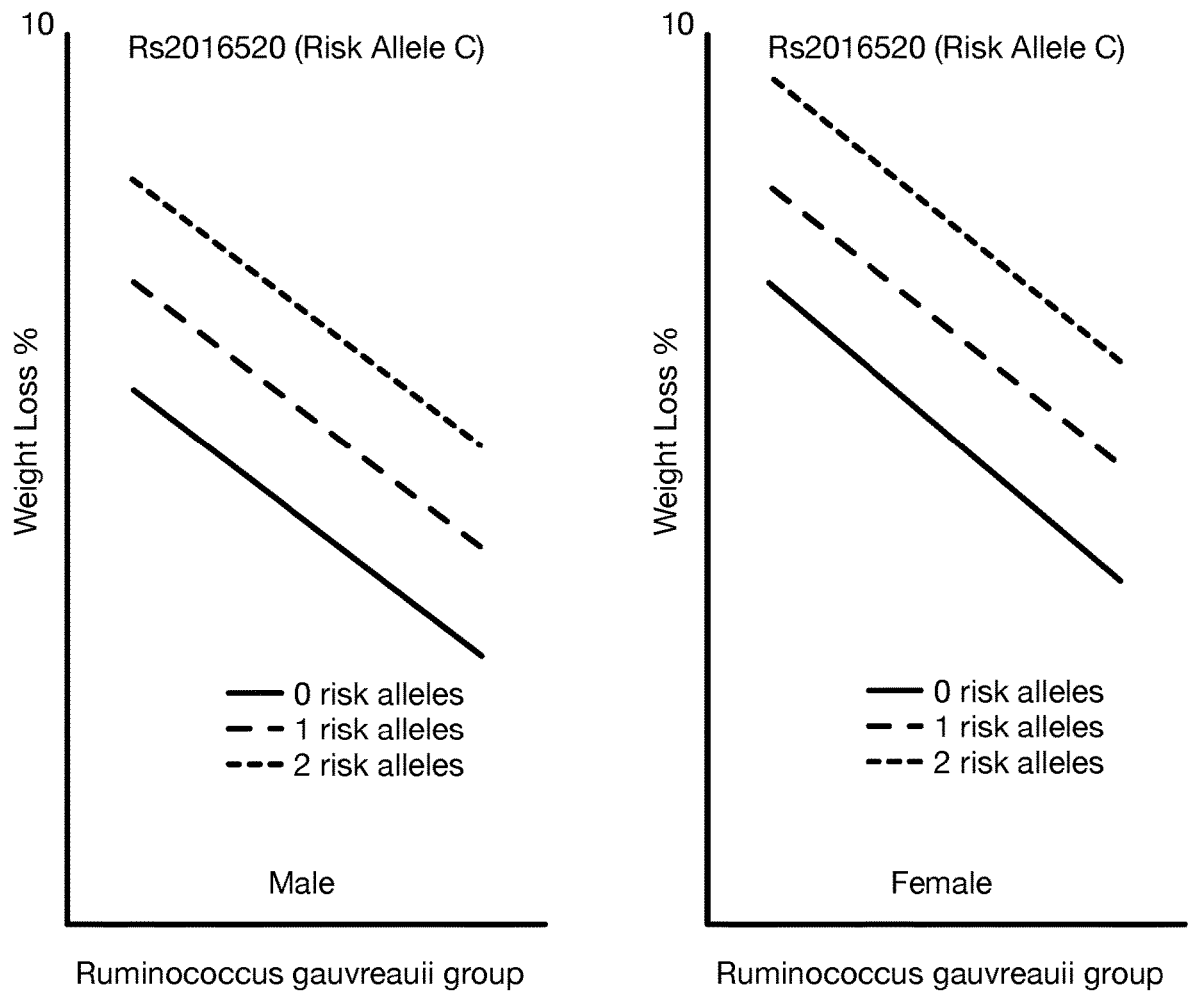
Figure 6E:
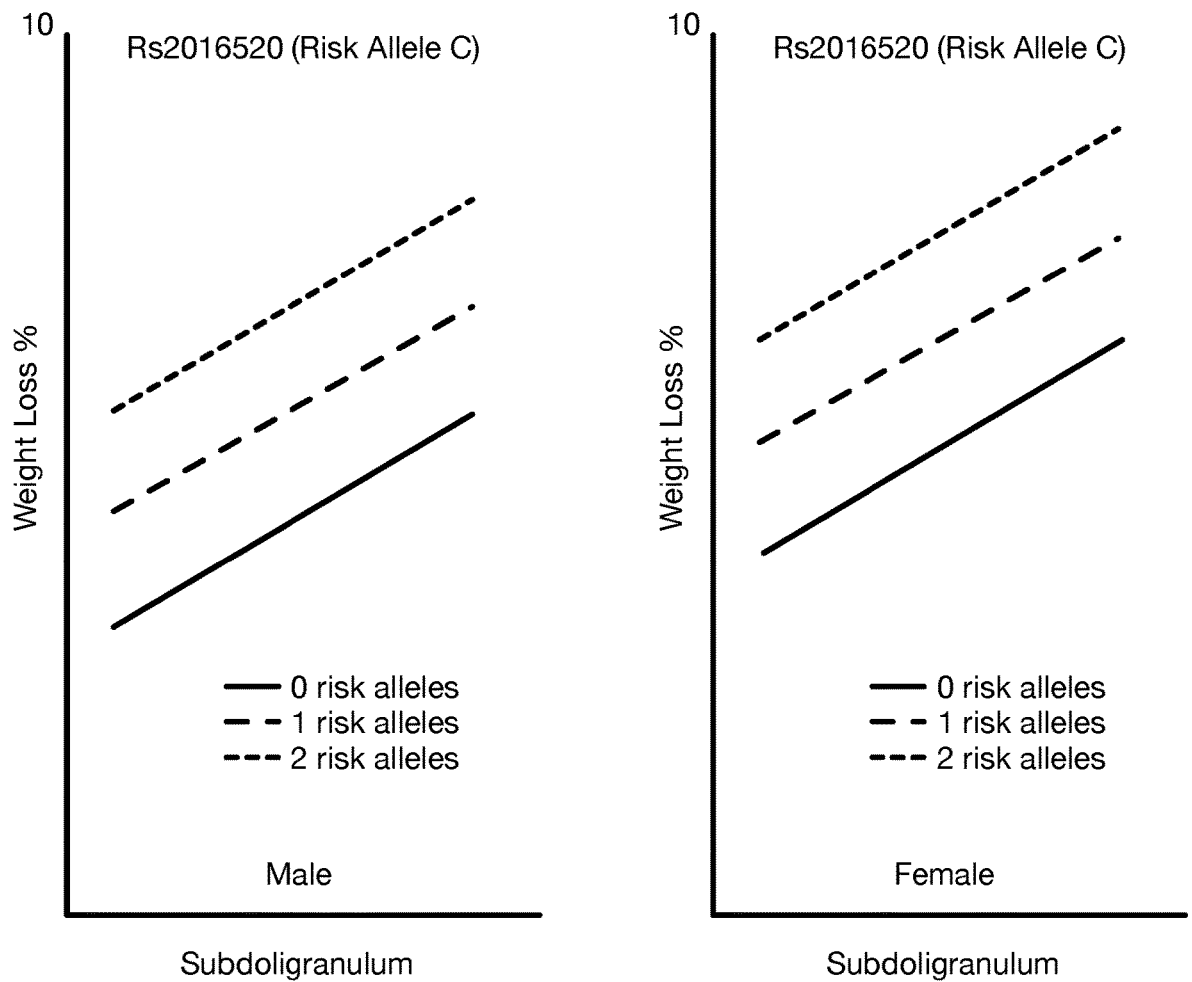

In examples, returned model outputs further demonstrated the interplay between genomic SNPs and gut microbiome taxa represented in samples from subjects. For example, for Rs2016520 (an SNP associated with cholesterol metabolism, BMI and waist circumference), as the risk alleles of SNP rs2016520 increase from 0 to 1 to 2, there is an increase in success in weight loss. FIG. 6D demonstrates that increased abundance of *Ruminococcus gauvreauii* is associated with diminished weight loss success in all three risk groups, whereas FIG. 6E demonstrates that increased abundance of Subdoligranulum is associated with increased weight loss success (panels A for females and panels B for males).

In examples, a principal ratio analysis of the 36 genera that passed the filters mentioned above was performed, and the pairs of genera that explained the most variance in the success-fail groups and the whole dataset are shown in Tables 16, 17, 18, and 19.

TABLE 16

Principal Ratio Analysis for Fail Group

|  | k | Partner | Pair | var |
|---|---|---|---|---|
| *Bacteroides* | 1 | *Prevotella* | *Bacteroides* | 16.9316952991137 |
| *Prevotella* | 2 | *Ruminococcus* | *Prevotella* | 32.0864230265136 |
| *Phascolarctobacterium* | 3 | *Bifidobacterium* | *Phascolarctobacterium* | 43.3048246803659 |

TABLE 17

Principal Ratio Analysis for Success Group

|  | k | Partner | Pair | var |
|---|---|---|---|---|
| *Bacteroides* | 1 | *Ruminococcus* | *Bacteroides* | 18.3813023348154 |
| *Rumirtococcus* | 2 | *Prevotella* | *Ruminococcus* | 33.8433359834344 |
| *Phascolarctobacterium* | 3 | *Dialister* | *Phascolarctobacterium* | 43.8564704808079 |

TABLE 18

Principal Ratio Analysis for the whole dataset

|  | k | Partner | Pair | var |
|---|---|---|---|---|
| *Ruminococcus* | 1 | *Bacteroides* | *Ruminococcus* | 17.9954294354687 |
| *Ruminococcus*1 | 2 | *Prevotella* | *Ruminococcus* | 32.9635549799476 |
| *Phascolarctobacterium* | 3 | *Dialister* | *Phascolarctobacterium* | 42.9881177639388 |

TABLE 19

Principal Ratio Analysis for Success/Fail dataset

|  | k | Partner | Pair | var |
|---|---|---|---|---|
| *Bacteroides*1 | 1 | *Ruminococcus* | *Bacteroides* | 17.2987646499403 |
| *Ruminococcus* | 2 | *Prevotella* | *Ruminococcus* | 32.8625810293734 |
| *Phascolarctobacterium* | 3 | *Dialister* | *Phascolarctobacterium* | 43.0784200857799 |

The digital therapeutics care programs provided to subjects, informed by genetic and baseline gut microbiome and their interactions with subject lifestyle. Personalized care program regimens generated according to model outputs were effective in achieving significant reductions of body weight across large subject pools. Different components of personalized care (e.g. fiber types) affect the microbial taxa identified in the models and their corresponding effect on reduction of weight, in a significant manner, which were demonstrated to guide creation of personalized treatment regimens. The platform thus generates precision dietary interventions for weight loss utilizing both genomic risk and baseline microbiome data, with digitally delivered recommendations alongside health coaching to drive active engagement of subjects for improved intervention efficacy. Moreover, the exemplary platform described, and variations thereof, can be readily implemented for digital therapeutics care for other comorbidities where genetics and gut microbiome play a role in disease etiology.

2.6 Methods—Model Training and Refinement

In some variations, as shown in FIG. 1B, the method 100 can further include refining the multi-omic model S170, wherein refining the multi-omic model includes: collecting a set of training data streams derived from a population of subjects, the set of training data streams capturing genetic data, microbiome data, biometric data, and lifestyle data, paired with diagnostic and therapeutic information, from the population of subjects S171, applying a set of transformation operations to the set of training data streams S172, creating a training dataset derived from the set of training data streams and the set of transformation operations S173, and training the multi-omic model in one or more stages, based upon the training dataset S174.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions.

Data/signal inputs indicated in relation to blocks S110, S120, S130, and S140 above and/or other inputs (e.g., contextual inputs, derivative inputs, combinatorial inputs, etc.) can be used for training the multi-omic model. In more detail, features may be transformed either individually or in combination before being processed by the model(s). Combinatorial features can include microbiome-derived features, genomic (e.g., SNP, allelic variations, loci of interest)-associated features, lifestyle features, demographic features, and/or other features.

Additionally or alternatively, dynamic aspects (e.g., changes over time in features, changes in frequency between instances of respective features, other temporal aspects, other frequency-related aspects, etc.) of features derived from the samples can be used to predict or otherwise anticipate health condition statuses for generation of personalized intervention plan components.

Inputs can be aggregated from populations of subjects associated with different demographic characteristics, health statuses, health conditions, lifestyles, and/or other suitable factors.

In relation to model architecture, inputs to models described above can produce outputs that are subsequently used as inputs to an overarching model (e.g., classification model having multiple layers) that returns diagnostics, characterizations of the subject (e.g., in relation to health state, disease state, etc.), personalized intervention plan aspects, and/or other aspects based upon processing features in stages. However, the model(s) can implement other suitable architecture having other suitable flow for processing features derived from the inputs.

Returned classification outputs of models can include returned confidence-associated parameters in such classifications. In particular, confidence-associated parameters can have a score (e.g., percentile, other score) that indicates confidence in the returned output.

Furthermore, refined versions of the model can be configured to process fewer inputs (e.g., only a subset of inputs described above) in order to return accurate outputs for generating personalized intervention plan components associated with Blocks S150 and S160 above. Furthermore, previous features derived from inputs (e.g., new signals/signatures, interesting signals/signatures, etc.) can be returned by computing components during model refinement.

While embodiments, variations, and examples of models (e.g., in relation to inputs, outputs, and training) are described above, models associated with the method 100 can additionally or alternatively include other machine learning architecture.

Statistical analyses and/or machine learning algorithm(s) can be characterized by a learning style including any one or more of: supervised learning (e.g., using back propagation neural networks), unsupervised learning (e.g., K-means clustering), semi-supervised learning, reinforcement learning (e.g., using a Q-learning algorithm, using temporal difference learning, etc.), and any other suitable learning style.

Furthermore, any algorithm(s) can implement any one or more of: a regression algorithm, an instance-based method (e.g., k-nearest neighbor, learning vector quantization, self-organizing map, etc.), a regularization method, a decision tree learning method (e.g., classification and regression tree, chi-squared approach, random forest approach, multivariate adaptive approach, gradient boosting machine approach, etc.), a Bayesian method (e.g., naïve Bayes, Bayesian belief network, etc.), a kernel method (e.g., a support vector machine, a linear discriminant analysis, etc.), a clustering method (e.g., k-means clustering), an associated rule learning algorithm (e.g., an Apriori algorithm), an artificial neural network model (e.g., a back-propagation method, a Hopfield network method, a learning vector quantization method, etc.), a deep learning algorithm (e.g., a Boltzmann machine, a convolution network method, a stacked auto-encoder method, etc.), a dimensionality reduction method (e.g., principal component analysis, partial least squares regression, etc.), an ensemble method (e.g., boosting, boot strapped aggregation, gradient boosting machine approach, etc.), and any suitable form of algorithm.

In an example, model training can be based on a cohort of subjects who lose >5% body weight while receiving personalized digital care for weight loss and present concomitant reduction of cardiovascular and/or functional bowel disorder symptomatology. A diagnostic signature can be built based on predictive variables identified in linear and/or logistic regression models on the likelihood of a subject having a disorder versus not exhibiting a disorder. Example variables include: demographics (e.g., number of coaching sessions completed, number of weight entries logged, number of Bristol stool scores logged, etc.), gut microbiome taxa (e.g., *Ruminococcus torques* group, *Haemophilus, Akkermansia, Terrisporobacter, Holdemanella, Fusicatenibacter, Anaerostipes*, other taxa described etc.), gut microbiome functional pathways (e.g. acetate production, serotonin production, etc.), genomic SNPs (e.g. associated with inflammation, associated with obesity, associated with gut disorders, associated with other factors described, etc.), and any other type of variable. In the same example cohort, therapeutic signatures can be identified in models for reduction in symptomatology for different conditions (e.g., diarrhea, constipation, IBS, IBD, gassiness, bloating, reflux, cramping, abdominal pain, etc.). Example variables for therapeutic signatures include demographics (e.g., gender, number of food posts, etc.), genomics markers (e.g., rs7775228, other markers described, etc.), gut microbiome taxa (e.g., *Parabacteroides, Lachnospira, Eubacterium coprostanoligenes* group, *Ruminococcus torques, Lactobacillus, Prevotella*, other taxa described, etc.), and any other type of variable.

The invention(s) can also include modified variations of operations for training and refinement of other model architecture configured for improving other conditions.

3. SYSTEM

Figure 7A:
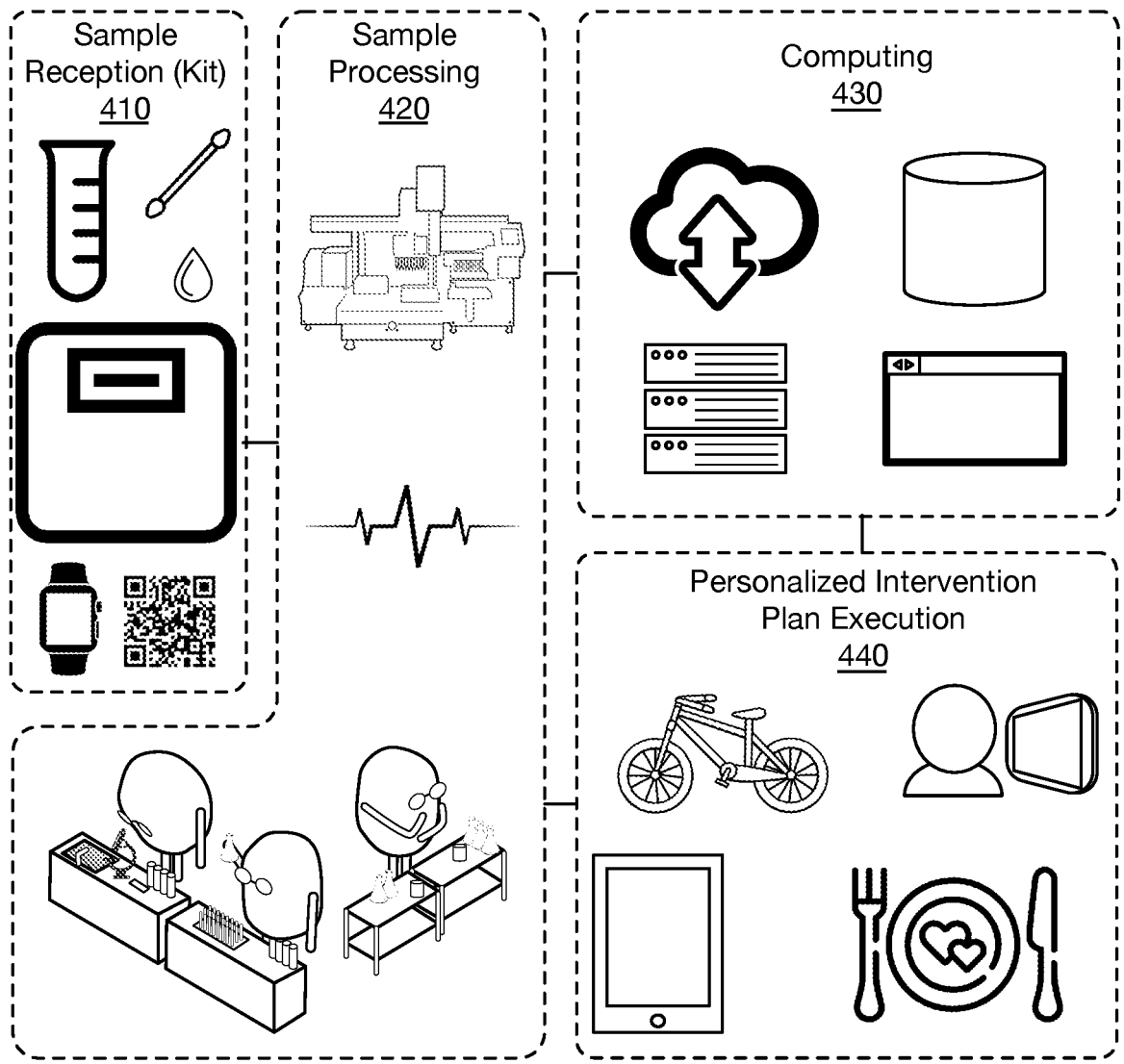
FIG. 7A depicts an embodiment of a system implementing multi-omic models to generate personalized care programs for subjects.

As shown in FIG. 7A, a system/platform 400 for multi-omics interventions as diagnostics, for generation of personalized therapeutic and diagnostic approaches, includes: one or more sample reception subsystems 410; one or more sample processing subsystems 420 in communication with the sample reception subsystems 410; a computing platform 430 comprising one or more processing subsystems comprising non-transitory computer-readable medium comprising instructions stored thereon, that when executed by the processing subsystems perform one or more steps of methods described above; and one or more execution subsystems 440 configured to execute components of personalized intervention plans informed by processes of the computing platform 230. In variations, the execution subsystems 440 can be configured to execute control instructions generated by the computing platform 430, where control instructions can involve instructions for controlling operation modes of one or more of: application interfaces (e.g., mobile application interfaces, web application interfaces, etc.) for signal reception, data aggregation, and/or retrieval of other inputs to be processed by system architecture; sample processing architecture (e.g., by automated/robotic subsystems), communication interfaces for performing telehealth operations, communication interfaces for providing group therapies, communication interfaces for providing counseling (e.g., through human entities, through digital entities), interfaces for providing rewards and/or other incentives to subjects, interfaces for providing and monitoring tasks provided to subjects, interfaces for connecting devices (e.g., biometric monitoring devices) of the subject with an account of the subject within the system/platform 100; interfaces for providing medications to the subject; interfaces for providing dietary advice/tracking diet behavior of the subject; and/or other suitable functionality for delivering components of a personalized intervention plan.

Embodiments of the system 400 are configured to perform one or more portions of methods described above; however, variations of the system 400 can be configured to perform other suitable methods.

The sample reception subsystem(s) 410 can include automated platforms for receiving and storing laboratory samples from sample acquisition devices of the sampling kits described above. The sample processing subsystem(s) 420 in communication with the sample reception subsystems 410 can include automated platforms for executing processing operations described above (e.g., in relation to sequencing and detection of genomic regions of interest in samples, in relation to sequencing and detection of microbiome taxa and functions of interest from samples, etc.). Such sample reception subsystems 410 and sample processing subsystems 420 can include automated and/or robotic apparatuses for transferring sample material and/or combining sample material with processing reagents, delivering processed samples to sequencing equipment, returning results from sequencing equipment for analysis by the computing platform 430, and/or other performing other suitable operations.

The computing platform 430 comprising one or more processing subsystems comprising non-transitory computer-readable medium comprising instructions stored thereon, that when executed by the processing subsystems perform one or more steps of methods described above; and one or more execution subsystems 440 configured to execute components of personalized intervention plans informed by processes of the computing platform 430.

The execution subsystems 440 can be configured to execute control instructions generated by the computing platform 430, where control instructions can involve instructions for controlling operation modes of one or more of: application interfaces (e.g., mobile application interfaces, web application interfaces, etc.) for signal reception, data aggregation, and/or retrieval of other inputs to be processed by system architecture; sample processing architecture (e.g., by automated/robotic subsystems), communication interfaces for performing telehealth operations, communication interfaces for providing group therapies, communication interfaces for providing counseling (e.g., through human entities, through digital entities), interfaces for providing rewards and/or other incentives to subjects, interfaces for providing and monitoring tasks provided to subjects, interfaces for connecting devices (e.g., biometric monitoring devices) of the subject with an account of the subject within the system/platform 400; interfaces for providing medications to the subject; interfaces for providing dietary advice/tracking diet behavior of the subject; and/or other suitable functionality for delivering components of a personalized intervention plan.

In particular, the execution subsystems 440 are structured to implement a next-generation, prescription-grade, digital therapeutics program that uses artificial intelligence (AI) to analyze genetics, gut bacteria, lifestyle habits, socioeconomic and behavioral risk patterns to create evidence-based personalized nutrition, fitness, sleep and stress management program to reduce weight and reverse weight-related inflammatory gut, musculoskeletal, cardiovascular insulin-related, and/or illnesses. In examples, the execution subsystems 440 are structured to execute digital precision care interventions by mobile applications of subject devices. The execution subsystems 440 include non-transitory media storing computer-readable instructions and architecture for a genomic loci and gut microbiome-informed health program that is geared primarily toward individuals who suffer from inflammatory health conditions typically associated with being overweight, obese, or otherwise having a cardiovascular health issue.

Figure 7B:
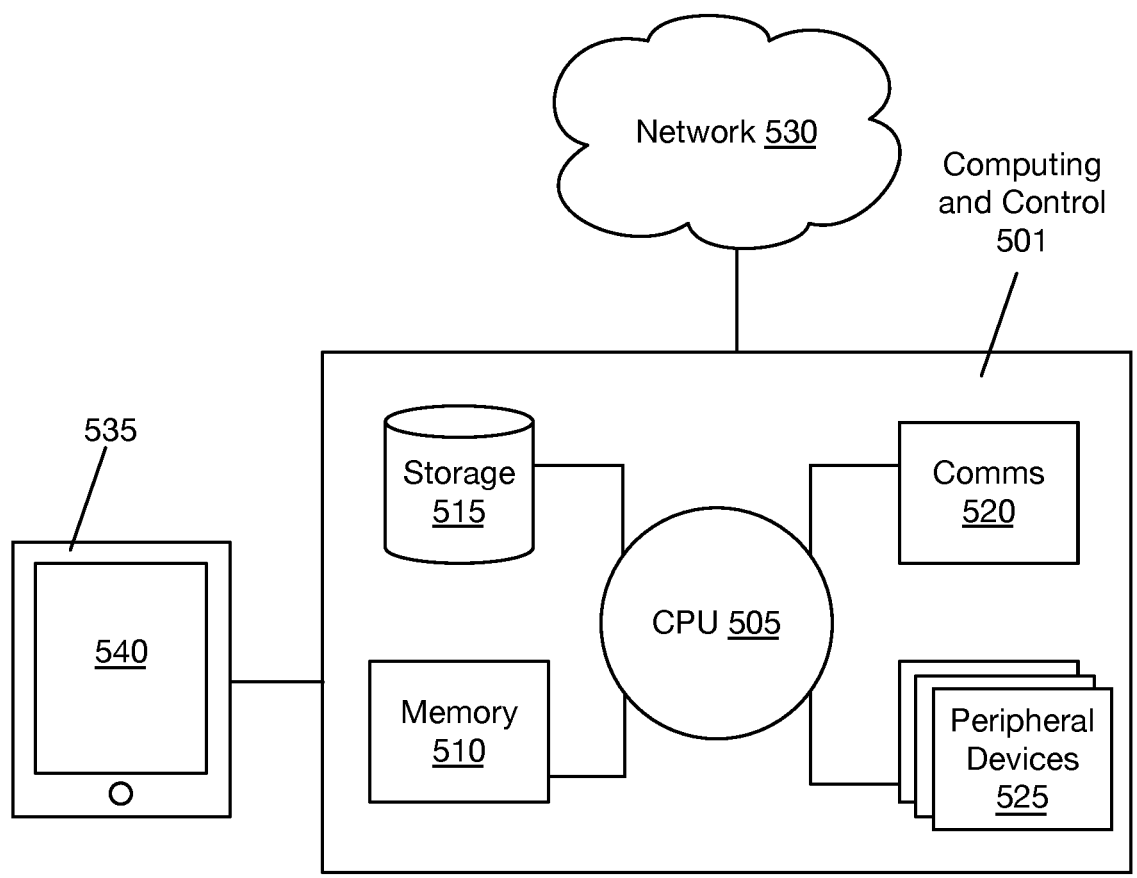
FIG. 7B depicts an embodiment of computing and control system elements for generating personalized care programs for subjects.

FIG. 7B depicts an embodiment of a computing and control system 501 configured to execute one or more portions of methods described. The computing and control subsystem 501 can be programmed or otherwise configured to, for example, extract, receive, and process input data with model architecture, and to return components of a personalized care program for a subject that can be delivered (e.g., as a prescription digital therapeutic).

The computing and control subsystem 501 includes architecture for regulating various aspects of sample/data processing, personalized care program generation, and other functionalities of the present disclosure. The computing and control subsystem 501 can be an electronic device of a user or a computer system that is remotely located with respect to the electronic device. The electronic device can be a mobile electronic device.

The computing and control subsystem 501 includes a central processing unit (CPU, also "processor" and "computer processor" herein) 505, which can be a single core or multi core processor, or a plurality of processors for parallel processing. The computing and control subsystem 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet.

In some embodiments, the network 530 is a telecommunication and/or data network. The network 530 can include one or more computer servers, which can enable distributed computing, such as cloud computing. For example, one or more computer servers may enable cloud computing over the network 530 ("the cloud") to perform various aspects of facilitating charging of an electric vehicle, with desired security, authentication, and locking functionalities associated with various types of charging sessions and/or different users. Such cloud computing may be provided by cloud computing platforms such as, for example, Amazon Web Services (AWS), Microsoft Azure, Google Cloud Platform, and IBM cloud. In some embodiments, the network 530, with the aid of the computer system 501, can implement a peer-to-peer network, which may enable devices coupled to the computer system 501 to behave as a client or a server.

The CPU 505 can include one or more computer processors and/or one or more graphics processing units (GPUs). The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback. The CPU 505 can be part of a circuit, such as an integrated circuit. One or more other components of the computing and control subsystem 501 can be included in the circuit. In some embodiments, the circuit is an application specific integrated circuit (ASIC).

The storage unit 515 can store files, such as drivers, libraries and saved programs. The storage unit 515 can store user data, e.g., user preferences and user programs. In some embodiments, the computer system 501 can include one or more additional data storage units that are external to the computer system 501, such as located on a remote server that is in communication with the computer system 501 through an intranet or the Internet.

The computing and control subsystem 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computing and control subsystem 501, such as, for example, on the memory 510 or electronic storage unit 515. The machine executable or machine-readable code can be provided in the form of software. During use, the code can be executed by the processor 505. In some embodiments, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Embodiments of the systems and methods provided herein, such as the computing and control subsystem 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as the main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computing and control subsystem 501 can include or be in communication with an electronic display 535 that comprises a user interface (UI) 540 for providing, for example, a visual display indicative of statuses associated with charging of an electric vehicle, security information, authentication information, and locking statuses associated with various types of charging sessions and/or different users. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, facilitate charging of an electric vehicle, with desired security, authentication, and locking functionalities associated with various types of charging sessions and/or different users.

In one set of embodiments, methods implemented by way of or as supported by the computing and control subsystem 501 can include methods for sample/data processing, personalized care program generation, and other functionalities. Communicated statuses can then be used by the system 100 to return notifications (e.g., to the electric vehicle operator, to a fleet manager, to another entity) and/or execute other actions for providing personalized care.

Additionally or alternatively, the computing and control subsystem 501 can include architecture with programming to execute other suitable methods.

4. CONCLUSIONS

Embodiments of the invention(s) can include every combination and permutation of the various system components and the various method processes, including any variants (e.g., embodiments, variations, examples, specific examples, figures, etc.), where portions of embodiments of the methods and/or processes described herein can be performed asynchronously (e.g., sequentially), concurrently (e.g., in parallel), or in any other suitable order by and/or using one or more instances, elements, components of, and/or other aspects of the system and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the methods and/or systems can be embodied and/or implemented at least in part as a machine configured to receive a computer-readable medium storing computer-readable instructions. The instructions can be executed by computer-executable components that can be integrated with embodiments of the system. The computer-readable medium can be stored on any suitable computer-readable media such as RAMs, ROMs, flash memory, EEPROMs, optical devices (CD or DVD), hard drives, floppy drives, systems for cloud computing, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the methods, systems, and/or variants without departing from the scope defined in the claims. Variants described herein are not meant to be restrictive. Certain features included in the drawings may be exaggerated in size, and other features may be omitted for clarity and should not be restrictive. The figures are not necessarily to scale. The absolute or relative dimensions or proportions may vary. Section titles herein are used for organizational convenience and are not meant to be restrictive. The description of any variant is not necessarily limited to any section of this specification.

What is claimed is:

1. A method for prevention and treatment of a cardiovascular condition, the method comprising:
   simultaneously reducing severity of a set of cardiovascular symptoms by at least 10%, producing greater than 2% weight loss, and reducing hemoglobin A1c levels by at least 0.5% compared to a baseline hemoglobin A1c level in a subject upon:
   receiving a set of samples from the subject;
   receiving a biometric dataset from the subject;
   receiving a lifestyle dataset from the subject;
   returning a genomic profile and one or more microbiome states including a baseline profile upon processing the set of samples, the biometric dataset, and the lifestyle dataset with a set of transformation operations;
   returning a set of genomic features from a multi-omic model comprising architecture that processes the genomic profile and the one or more microbiome states, wherein said architecture is configured to filter out amplicon sequence variants (ASVs) associated with *Elusimicrobiota, Nanoarchaeota,* and *Bdellovibrionota,* and wherein the set of genomic features returned from the multi-omic model comprises characterizations of risk allele detection for the subject, for a set of SNPs comprising: rs10246939, rs1042713, rs10741657, rs11076023, rs1260326, rs12611820, rs1501299, rs17700633, rs1799931, rs1800566, rs1800795, rs2112347, rs2185570, rs2241766, rs236918, rs2815752, rs29941, rs4654748, rs4680, rs526934, rs6318, rs660339, rs6968554, rs6994076, rs7138803, rs7385804, rs762551, rs838147, and rs9376026;
   generating a personalized intervention plan for the subject from the set of genomic features; and
   executing the personalized intervention plan for the subject.

2. The method of claim 1, wherein the set of cardiovascular symptoms comprises: blood pressure, fasting blood sugar, glycemic response, high density lipids, and low density lipids.

3. The method of claim 1, wherein the set of samples comprises a saliva sample and one or more gut samples, and wherein the set of transformation operations comprises nucleic acid extraction, purification, and genotyping for the saliva sample, and amplification of and generating a set of sequencing reads from the one or more gut samples.

4. The method of claim 3, wherein the set of transformation operations further comprises demultiplexing, generating amplicon sequence variants (ASVs), performing taxonomic and functional annotation of the set of sequencing reads based on at least one of local and global alignment methods, and graph-based methods, linear and nonlinear dimensionality reduction, and applications of supervised, semi-supervised and unsupervised machine or statistical inference methods to derive informative features from the microbiome profiles.

5. The method of claim 3, wherein the set of transformation operations further comprises imputing missing sites, determining genetic ancestry of the subject, estimating genetic parameters comprising genetic diversity and homozygosity, estimating scores representing inherited risk, and estimated values of qualitative, continuous and categorical traits which are normalized to biological gender, genetic ancestry, age, socioeconomic status, biometric measurements and life-style variables.

6. The method of claim 1, wherein receiving the biometric dataset comprises receiving a bodyweight value of the subject generated from a digital weighing scale, and wherein the biometric dataset comprises a body mass index (BMI) of the subject.

7. The method of claim 1, wherein receiving the biometric dataset comprises receiving a blood chemical and biochemical profile, and wherein the biometric dataset comprises one or more of: medication use, fasting blood sugar, glycemic response, high density lipids, and low density lipids.

8. The method of claim 1, wherein the lifestyle dataset comprises data derived from: a morning energy level, dietary behavior, sleep behavior, stress levels, cravings, exercise behavior, meditation behavior, state of symptoms of the subject, medication use, social determinants of health, familial determinants of health, and work determinants of health.

9. The method of claim 1, wherein the multi-omic model comprises a first subarchitecture that processes genomic input data, said first subarchitecture structured to infer non-genotyped alleles by means at least one of dimensionality reduction and statistical inferences methods for data imputations, with detection and encoding values of a set of risk alleles of the genomic profile for the subject.

10. The method of claim 1, wherein the multi-omic model comprises a second subarchitecture that processes microbiome-associated input data, said second subarchitecture structured to return microbial taxonomic abundances of the microbiome state, said second subarchitecture further structured to return microbial diversity indices of a whole microbial community or a subset of the whole microbial community, and functional data, and said second subarchitecture further structured to transform microbial taxonomic and functional abundances to compositionally transformed and arithmetically derived values.

11. The method of claim 1, further comprising: returning a set of microbiome features for the subject from the multi-omic model, and generating the personalized intervention plan from the set of genomic features and the set of microbiome features.

12. The method of claim 11, wherein the set of SNPs further comprises: rs17300539, rs2016520, rs4074995, and rs7903146.

13. The method of claim 11, wherein the set of microbiome features comprises features associated with: *Ruminococcus gauvreauii* group, Subdoligranulum, *Eubacterium brachy* group, *Eubacterium nodatum* group, *Blautia, Anaerostipes, Bacteroides, Prevotella, Phascolarctobacterium, Ruminococcus, Bifidobacterium*, and *Dialister.*

14. The method of claim 11, wherein generating the personalized intervention plan comprises returning a dietary recommendation configured to adjust taxonomic abundances and microbiome function present in the set of microbiome features, based upon risk alleles of the set of genomic features and the one or more microbiome states of the subject.

15. The method of claim 11, wherein the personalized intervention plan is delivered digitally through a mobile device application, and further comprises an application-interface between a coaching entity and the subject.

16. The method of claim 1, wherein at least one of generating the genomic profile, the baseline and subsequent microbiome states of the one or more microbiome states, the set of signatures, and the personalized intervention plan comprises refining the multi-omic model upon:
  collecting a set of training data streams derived from a population of subjects, the set of training data streams capturing genetic data, microbiome data, biometric data, and lifestyle data, paired with diagnostic and therapeutic information, from the population of subjects,
  applying a set of transformation operations to the set of training data streams,
  creating a training dataset derived from the set of training data streams and the set of transformation operations, and training the multi-omic model in one or more stages, based upon the training dataset.

* * * * *